United States Patent
Wischik et al.

(10) Patent No.: US 7,893,054 B2
(45) Date of Patent: *Feb. 22, 2011

(54) MATERIALS AND METHODS RELATING TO PROTEIN AGGREGATION IN NEURODEGENERATIVE DISEASE

(75) Inventors: Claude Michel Wischik, Aberdeen (GB); David Horsley, Aberdeen (GB); Janet Elizabeth Rickard, Aberdeen (GB); Charles Robert Harrington, Aberdeen (GB)

(73) Assignee: Wista Laboratories Ltd., Singapore (SG)

( * ) Notice: Subject to any disclaimer, the term of this patent is extended or adjusted under 35 U.S.C. 154(b) by 0 days.

This patent is subject to a terminal disclaimer.

(21) Appl. No.: 12/010,649

(22) Filed: Jan. 28, 2008

(65) Prior Publication Data

US 2009/0075984 A1 Mar. 19, 2009

Related U.S. Application Data

(63) Continuation of application No. 10/451,782, filed as application No. PCT/GB02/00153 on Jan. 15, 2002, now Pat. No. 7,335,505.

(30) Foreign Application Priority Data

Jan. 15, 2001 (GB) ................... 0101049.5

(51) Int. Cl.
*A61K 31/54* (2006.01)

(52) U.S. Cl. ............... 514/224.8; 514/212.01
(58) Field of Classification Search ............ None
See application file for complete search history.

(56) References Cited

U.S. PATENT DOCUMENTS

| | | | |
|---|---|---|---|
| 2,928,767 | A | 3/1960 | Gulesich et al. |
| 5,693,638 | A | 12/1997 | Myers |
| 5,827,644 | A | 10/1998 | Floyd et al. |
| 6,953,794 | B2 | 10/2005 | Wischik et al. |
| 2006/0014216 | A1 | 1/2006 | Wischik et al. |

FOREIGN PATENT DOCUMENTS

| | | |
|---|---|---|
| DE | 44 30 091 A1 | 8/1994 |
| EP | 0 457 295 | 11/1991 |
| EP | 0 618 968 B1 | 10/1994 |
| EP | 0 737 671 A2 | 10/1996 |
| EP | 0 909 814 A2 | 4/1999 |
| EP | 0 911 390 A2 | 4/1999 |
| EP | 0 911398 A2 | 4/1999 |
| EP | 1 067 386 A2 | 1/2001 |
| FR | 2 788 436 | 7/2000 |
| WO | WO 89 03993 | 5/1989 |
| WO | WO 93 01348 | 2/1993 |

(Continued)

OTHER PUBLICATIONS

U.S. Appl. No. 11/391,675, filed Mar. 29, 2006, Wischik, et al.

(Continued)

*Primary Examiner*—Olga N Chernyshev
(74) *Attorney, Agent, or Firm*—Foley & Lardner LLP

(57) ABSTRACT

The present invention is directed to methods for the treatment or prophylaxis of a tauopathy comprising administering to a patient in need thereof a medicament comprising a phenothiazine.

15 Claims, 50 Drawing Sheets

FOREIGN PATENT DOCUMENTS

| WO | WO 93 03177 | 2/1993 |
|---|---|---|
| WO | WO 93 03369 | 2/1993 |
| WO | WO 9311231 | 6/1993 |
| WO | WO 95 05466 | 2/1995 |
| WO | WO 95/05601 | 2/1995 |
| WO | WO 96 04915 | 2/1996 |
| WO | WO 96 05837 | 2/1996 |
| WO | WO 96/30766 | 10/1996 |
| WO | WO 96 30766 | 10/1996 |
| WO | WO 99/62548 | 12/1999 |
| WO | WO 01/53340 A2 | 7/2001 |
| WO | WO 02/03972 A2 | 1/2002 |
| WO | WO 02/04025 A1 | 1/2002 |
| WO | WO 02/059150 | 8/2002 |
| WO | WO 02/075318 A2 | 9/2002 |
| WO | WO 03/007933 A1 | 1/2003 |
| WO | WO 2005/030676 A1 | 4/2005 |
| WO | WO 2006/032879 A2 | 3/2006 |

OTHER PUBLICATIONS

A. Grover, et al., "5' splice site mutations in tau associated with the inherited dementia FTDP-17 affect a stem-loop structure that regulates alternative splicing of Exon 10*", The Journal of Biological Chemistry, May 21, 1999 issue, vol. 274, No. 21, pp. 15134-15143.

A. Ito, et al., "Enhancing effect of ascorbate on toluidine blue-photosensitization of yeast cells", Photochemistry and Photobiology, 1982, vol. 35, pp. 501-505.

A. Schneider, et al., "Phosphorylation that detaches tau protein from microtubules (Ser262, Ser214) also protects it against aggregation into Alzheimer paired helical filaments", Biochemistry, 1999, vol. 38, pp. 3549-3558.

A.M. Giannetti, et al., "Fibers of tau fragments, but not full length tau, exhibit a cross ~3-structure: implications for the formation of paired helical filaments", Protain Science, 2000, vol. 9, pp. 2427-2435.

A.M. Shojania, et al., "The effect of toluidine blue and methylene blue in immunochemical reactions in vitro", Clinical Immunology and Immunopathology, 1987, vol. 43, pp. 223-228.

A.S.N. Murphy, et al, "Cyclic-voltammetric studies of some phenothiazine dyes", J. Chem. Soc., Faraday Trans, 1984, vol. 80, pp. 2745-2750.

B. Lichtenberg-Kraag, et al., "Alzheimer-type phosphorylation of microtubule-associated protein tau in vitro", 1991/92.

B. Lichtenberg-Kraag, et al., "Phosphorylation-dependent epitopes of neurofilament antibodies on tau protein and relationship with Alzheimer tau", Proc. Natl. Acad. Sci. USA, 1992, vol. 89, pp. 5384-5388.

B. Pedrotti, et al., "Interactions of microtubule-associated protein MAP2 with unpolymerized and polymerized tubulin and actin using a 96-well microtiter plate solid-phase immunoassay", Biochemistry, 1994, vol. 33, pp. 8798-8806.

B.H. Anderton, et al., "Dendritic changes in Alzheimer's disease and factors that may underlie these changes", Prog. Neurobiol., Aug. 1998, 55(6), pp. 595-609.

C. Bancher, et al., "Accumulation of abnormally phosphorylated T precedes the formation of neurofibrillary tangles in Alzheimer's disease", Brain Research, 1989, vol. 477, pp. 90-99.

C. Smith, et al., "The molecular pathology of Alzheimer's disease: are we any closer to understanding the neurode enerative process?", Neuropathology and Applied Neurobiology, 1994, vol. 20, pp. 322-338.

C. Wischik, "Molecular neuropathology of Alzheimer's disease", 1989, pp. 44-70.

C. Wischik, "Molecular neuropathology of Alzheimer's disease", John Libbey & Co., 1991, pp. 239-250.

C.B. Caputo, et al., "Amyloid-like properties of a synthetic peptide corresponding to the carboxy terminus of 3-amyloid protein precursor", Archives of Biochemistry and Biophysics, 1992, vol. 292, pp. 199-205.

C.M. Wischik "Selective inhibition of Alzheimer Disease-like tau aggregation by phenothiazines", Proceedings of the National Academy of Sciences of USA, Washington, D.C., vol. 93, Oct. 10, 1996, pp. 11213-11218.

C.M. Wischik, "Cell biology of the Alzheimer tangle", Current Opinion in Cell Biology, 1989, vol. 1, pp. 115-122.

C.M. Wischik, et al., "Author's response to commentaries", Neurobiology of Aging, 1995, vol. 16, No. 3, pp. 423-431.

C.M. Wischik, et al., "Isolation of a fragment of tau derived from the core of the paired helical filament of Alzheimer disease", Proc. Natl. Acad. Sci. USA, 1988, vol. 85, pp. 4506-4510.

C.M. Wischik, et al., "Modelling prion-like processing of tau protein in Alzheimer's disease for pharmaceutical development", 1997, Harwood Acad. Publishers, pp. 185-241.

C.M. Wischik, et al., "Quantitative analysis of tau protein in paired helical filament preparations" Implications for the role of tau protein phosphorylation in PHF assembly in Alzheimer's disease, Neurobiology of Aging, 1995, vol. 16, No. 3, pp. 409-431.

C.M. Wischik, et al., Structural characterization of the core of the paired helical filament of Alzheimer disease, Proc. Natl. Acad. Sci. USA, 1988, vol. 85, pp. 4884-4888.

C.M. Wischik, et al., "Structure, biochemistry and molecular pathogenesis of paired helical filaments in Alzheimer's disease", Pathbiology of Alzheimer's Disease, 1995, pp. 10-39.

C.M. Wischik, et al., "Subunit structure of paired helical filaments in Alzheimer's disease", The Journal of Cell Biology, 1985, vol. 100, pp. 1905-1912.

C.R. Harrington, et al., "Competitive ELISA for the measurement of tau protein in Alzheimer's disease", Journal of Immunological Methods, 1990, vol. 134, pp. 261-271.

C.R. Harrington, et al., "Measurement of distinct immunochemical presentations of tau protein in Alzheimer's disease", Proc. Natl. Acad. Sci., Jul. 1991, vol. 88, pp. 5842-5846.

D. van Rossum, et al., "Cytoskeletal dynamics in dendritic spines: direct modulation by glutamate receptors", Trends Neurosci., 1992, vol. 22, pp. 290-295.

D.A. Lomas, et al., "The mechanism of Z a1-antitrypsin accumulation in the liver", Nature, 1992, vol. 357, pp. 605-607.

E. Braak, et al., "Alzheimer's disease: transiently developing dendritic changes in pyramidal cells of sector CAI of the amnion ' s horn" , Acta NeuroPathol,1997, vol. 93, pp. 323-325.

E. Montejo de Garcini, et al., "In vitro conditions for the self-polymerization of the microtubule-associated protein", J. Biochem., 1987, vol. 102, No. 6, pp. 1415-1421.

E. Montejo de Garcini, et al., "Self assembly of microtubule associated protein TAU into filaments resembling those found in Alzheimer disease", Biochemical and Biophysical Research Communications, 1986, pp. 790-797.

E. Montejo de Garcini, et al., "Tau factor polymers are similar to paired helical filaments of Alzheimer ' s disease" , Elsevier Science Publishers B.V., 1988, pp. 150-154.

E.B. Makaetova-Ladinska, et al., "Staging of cytoskeletal and beta-amyloid changes in human isocortex reveals biphasic synaptic protein response during progression of Alzheimer's disease", American Journal of Pathology, Aug. 2000, vol. 157, No. 2, pp. 623-636.

E.M. Link, "Targeting melanoma with 211At/1311-methylene blue: preclinical and clinical experience", Hybridoma, 1999, vol. 18, No. 1, pp. 77-82.

H. Aizawa, et al., "Microtubule-binding domain of tau proteins", Journal of Biological Chemistry, 1988, vol. 263, pp. 7703-7707.

H. Ksiezak-Reding and J.S. Wall, "Mass and physical dimensions of two distinct populations of paired helical filaments", Neurobiology of Aging, 1994, vol. 15, No. 1, pp. 11-18.

H. Ksiezak-Reding and S.H. Yen, "Structural stability of paired helical filaments requires microtubule-binding domains of tau: A model for self association", Neuron, 1991, vol. 6, pp. 717-728.

H. Ksiezak-Reding, "Assembled tau filaments differ from native paired helical filaments as determined by scanning transmission electron microscopy", STEM, 1998, pp. 86-98.

H. Wille, "Alzheimer-like paired helical filaments and antiparallel dimers formed from microtubule-associated protein tau in vitro", J. Cell Biol., 118, 1992, pp. 573-584.

H.J. Gertz, et al., "Examination of the validity of the hierarchical model of neuropathological staging in normal aging and Alzheimer's disease", Acta Neuropathol., 1998, vol. 95, pp. 154-158.

H.J. Gertz, et al., "The relationship between clinical dementia and neuropathological staging (Braak) in a very elderly community sample", Eur. Arch. Psychiatry Clin. Neurosci., 1996, vol. 246, pp. 132-136.

I. Grundke-Iqbal, et al., "Abnormal phosphorylation of microtubule-associated protein T (tau) in Alzheimer cytoskeletal pathology", Proc. Natl. Acad. Sci. USA, 1986, vol. 83, pp. 4913-4917.

J. Biernat, et al., "The switch of tau protein to an Alzheimer-like state includes the phosphorylation of two serine-proline motifs upstream of the microtubule binding region", EMBO Journal 11, 1992, pp. 1593-1597.

J. Garcia de Ancos, et al., "Differences in microtubule binding and self-association abilities of bovine brain tau isoforms", The Journal of Biological Chemistry, 1993, vol. 268, No. 11, pp. 7976-7982.

J. Perez-Tur, et al., "Neurodegenerative disease of Guam: Analysis of TAU", American Academy of Neurology, 1999, vol. 53, pp. 411-412.

J.B. Epstein, et al., "The utility of toluidine blue application as a diagnostic aid in patients previously treated for upper oropharyngeal carcinoma", Oral medicine, 1997, vol. 83, No. 5, pp. 537-547.

J.E. Holoubek, et al., "Toluidine blue in bleeding associated with thrombopenia", J.A.M.A., Jan. 22, 1949, vol. 139, No. 4, pp. 214-216.

J.L. Martinez, et al., "Methylene blue alters retention of inhibitory avoidance responses", Physiol. Psychol., 1978, vol. 6(3), pp. 387-390.

J.-P. Brion, et al., "Characterization of a partial cDNA specific for the high molecular weight microtubule-associated protein MAP2 that encodes epitopes shared with pared helical filaments of Alzheimer's disease", Dementia, 1990, vol. 1, pp. 304-315.

K. Ishiguro, et al., "A novel tubulin-dependent protein kinase forming a paired helical filament epitope on tau", J. Biochem, 1988, vol. 104, pp. 319-321.

K. Ishiguro, et al., "A serine/threonine proline kinase activity is included in the tau protein kinase fraction forming a paired helical filament epitope", Neuroscience Letters, 1991, vol. 128, pp. 195-198.

K. Ishiguro, et al., "Phosphorylation sites on tau by tau protein kinase I, a bovine derived kinase generating an epitope of paired helical filaments", Neuroscience Letters, 1992, vol. 148, pp. 202-206.

K. Ishiguro, et al., "Tau protein kinase I converts normal tau protein into A68-like component of paired helical filaments", Journal of Biological Chemistry, 1992, vol. 267, pp. 10897-10901.

L. Poulter, et al., "Locations and immunoreactivities of phosphorylation sites on bovine and porcine tau proteins and a PHF-tau fragment", The Journal of Biological Chemistry, 1993, vol. 268, No. 13, pp. 9636-9644.

L.A. Cudd, et al., "Pharmacokinetics and toxicity of tolonium chloride in sheep", Vet Human Toxicol, Oct. 1996, vol. 38, No. 5, pp. 329-334.

Luisa Fasulo, et al., "Overexpression of Alzheimer's PHF core tau fragments: implications for the tau truncation hypothesis", Alzheimer's Research 2, 1996, pp. 195-200.

M. Goedert, et al., "Cloning and sequencing of the cDNA encoding a core protein of the paired helical filament of Alzheimer disease: Identification as the microtubule-associated protein tau", Proc. Natl. Acad. Sci. USA, Jun. 1988, vol. 85, pp. 4051-4055.

M. Goedert, et al., "Tau proteins of Alzheimer paired helical filaments: Abnormal phosphorylation of all six brain isoforms", Neuron, Jan. 1992, vol. 8, pp. 159-168.

M. Hutton, et al. "Association of missense and 5'-splice-site mutations in tau with the inherited dementia FTDP-17", Nature, Jun. 18, 1998, vol. 393, pp. 702-705.

M. Kiese, et al., "Comparative studies on the effects of toluidine blue and methylene blue on the reduction of ferrihaemoglobin in man and dog", Europ. J. Clin. Pharmacol., 1972, vol. 4, pp. 115-118.

M. Novak, et al., Molecular characterization of the minimal protease resistant tau unit of the Alzheimer's disease paired helical filament:, The EMBO Journal, 1993, vol. 12, No. 1, pp. 365-370.

M. Perez, et al., "In vitro assembly of tau protein: Mapping the regions involved in filament formation", Biochemistry, 2001, vol. 40, 5983-5991.

M. von Bergen et al. "Assembly of Tau Protein into Alzheimer Paired Helical Filaments Depends on a Local Sequence Motif Forming Beta Structure", Proceedings of the National Academy of Science, USA, Washington, D.C., vol. 97, No. 10, May 9, 2000, pp. 5129-5134.

M.A. DeTure, L. DiNoto, and D.L. Purich, "In vitro assembly of Alzheimer-like filaments. How a small cluster of charged residues in tau and MAP2 controls filament morphology", Journal of Biological Chemistry, 2002, vol. 277, pp. 34755-34759.

M.D. Ledesma, et al., "Implication of brain cdc2 and MAP2 kinases in the phosphorylation of tau protein in Alzheimer's disease", FEBS, 1992, vol. 308, No. 2, pp. 218-224.

M.W. Klymkowsky, "Weaving a tangled web: the interconnected cytoskeleton", Nature Cell Biology, 1999, vo. 1, No. 5, p. E121.

N. L. Callaway, et al., "Methylene blue restores spatial memory retention impaired by an inhibitor of cytochrome oxidase in rats", Neuroscience Letters, 2002, vol. 332, pp. 83-86.

O. Condamines, et al., "New immunoassay for the mapping of neurofibrillary degeneration in Alzheimer's disease using two monoclonal antibodies against human paired helical filament tau proteins", Neuroscience Letters, Jun. 9, 1995, vol. 192, No. 2, pp. 81-84.

P. Friedhoff, et al., "A nucleated assembly mechanism of Alzheimer paired helical filaments", Proc. Natl. Acad. Sci., USA, Dec. 1998, vol. 95, pp. 15712-15717.

P. Friedhoff, et al., "Rapid Assembly of Alzheimer-like paired helical filaments from microtubule-associated protein tai monitored by fluorescence in solution", Biochemistry, 1998, vol. 37, pp. 10223-10230.

R. Brandt, "Cytoskeletal mechanisms of axon outgrowth and pathfinding", Cell Tissue Res., 1998, vol. 292, 181-189.

R. Jakes, et al. "Identification of 3- and 4-repeat tau isoforms within the PHF is Alzheimer's disease", The EMBO Journal, 1991, vol. 10, No. 10, pp. 2725-2729.

R. Lai, "The role of abnormal phosphorylation of tau protein in the development of neurofibrillary pathology in Alzheimer's disease", Christ's College, 1994, pp. 1-243.

R. Mena, et al., "A progressive deposition of paired helical filaments (PHF) in the brain characterizes the evolution of dementia in Alzheimer's disease", Journal of Neuropathology and Experimental Neurology, 1991, pp. 474-490.

R. Mena, et al., "Monitoring pathological assembly of tau and 13-amyloid proteins in Alzheimer's diesease", Acta Neuropathol, 1994, pp. 50-56.

R. Mena, et al., "Staging and pathological assembly of truncated tau protein into paired helical filaments in Alzheimer's disease", Acta Neuropathol, 1995, pp. 633-641.

R. Sato-Harada, et al., "Microtubule-associated Proteins Regulate Microtubule Function as the Track for Intracellular Membrane Organelle Transports", Cell Structure Function 21, 1996, pp. 283-295.

R.Y.K. Laiet al., "Examination of phosphorylated tau protein as a PHF-precursor at early state Alzheimer's diseases", Neurobiology of Aging, 1995, vol. 16, No. 3, pp. 433-445.

S. Janciauskiene, et al., "In vitro amyloid fibril formulation from al-antitrypsin", Bio Chem, 1995, vol. 375, pp. 103-109.

S.A. Lewis, et al., "Microtubule-associated protein MAP2 shares a microtubule binding motif with tau protein", Science, 1988, vol. 242, pp. 936-939.

S.-H. Yens, et al., "Alzheimer's neurofibrillary tangles contain unique epitopes in common with the heat- stable microtubule-associated proteins tau and MAP2", American Journal of Pathology, 1987, vol. 126, pp. 81-91.

T. Hagestedt, et al., "Tau protein becomes long and stiff upon phosphorylation: correlation between paracrystalline structure and degree of phosphorylation", The Journal of cell biology, 1989, vol. 109, pp. 1643-1651.

T. Muller, "Light-microscopic demonstration of methylene blue accumulation sites in mouse brain after supravital staining", Acta Anat., 1992, vol. 144, pp. 39-44.

V.M.-Y. Lee et al., "A68: A major subunit of paired helical filaments and derivatized forms of normal tau", Science, 1991, vol. 251, pp. 675-678.

W. Bondareff, et al., "Immunohistochemical staging of neurofibrillary degeneration in Alzheimer's disease", Journal of Neuropathology and Experimental Neurology, Mar. 1994, vol. 53, No. 2, pp. 158-164.

W.L. Rumbolz, et al., "Use of protamine sulfate and toluidine blue for abnormal uterine bleeding", Am. J. Obst. & Gynec., May 1952, vol. 63, No. 5, pp. 1029-1037.

"Toluidinblau", Drug Information, Kohler & Co., Alsbach, Germany 1997.

A. Mashberg, "Tolonium (Toluidine blue) rinse—a screening method for recognition of squanous carcinoma—continuing study of oral-cancer 4", Journal of the American Medical Association, Jun. 245 (23): 2408-2410 (1981).

C.B. Caputo, et al., "The amyloid proteins of Alzheimer's disease as potential targets for drug therapy", Neurobiol. Aging, 10: 451-461 (1989).

C.M. Wischik, F. Theuring and C.R. Harrington, "The molecular basis of tau protein pathology in Alzheimer's disease and related neurodegenerative dementias", In Neurobiology of Alzheimer's Disease (Eds. D. Dawbarn & S.J. Allen) Oxford University Press, Oxford, pp. 103-206 (2001).

C.M. Wischik, Thesis "The structure and biochemistry of paired helical filaments in Alzheimer's disease", Part I and II, pp. 1-455. Cambridge University, 1989.

Allen JG, Grossman BJ, Elghammer, RM, Moulder PV, McKeen CL, Sanderson M, and Egner W. (1949) Abnormal bleeding II; further clinical experience with toluidine blue and protamine sulfate. Surgery, Gynecology and Obstetrics, 89(6): 692-703.

Lai et al., "Examination of phosphorylated tau protein as a PHF-precursor at early state Alzheimer's diseases", Neurobiol Aging, May-Jun. 16(3) 443-445 (1995).

Proto-assembly of tau

Truncation of N- and C-terminal domains

Minimal core tau unit dimer

Further binding of tau

Further truncation

Building up of core PHF

Diseases of protein aggregation.

| Protein | Disease | Aggregating domain and/or mutations | Fibril subunit size (kDa) | Reference |
|---|---|---|---|---|
| *Neurodegenerative disorders* | | | | |
| Prion protein | Prion diseases (CJD, nvCJD, Fatal familial insomnia, Gerstmann-Sträussler-Scheinker syndrome, Kuru) | *Inherited and sporadic forms* PrP-27-30; many mutations Fibrillogenic domains: 113-120, 178-191, 202-218 | 27 | Prusiner (1998) Gasset et al. (1992) |
| Tau protein | Alzheimer's disease, Down's syndrome, FTDP-17, CBD, post-encephalitic parkinsonism, Pick's disease, parkinsonism with dementia complex of Guam | *Inherited and sporadic forms* Truncated tau (tubulin-binding domain) 297-391 Mutations in tau in FTDP-17 Many mutations in presenilin proteins | 10-12 | Wischik et al. (1988) Hutton et al. (1998) Czech et al. (2000) |
| Amyloid β-protein | Alzheimer's disease, Down's syndrome | *Inherited and sporadic forms* Amyloid β-protein; 1-42(3); 11 mutations in APP in rare families | 4 | Glenner & Wong (1984) Goate et al. (1991) |
| Huntingtin Ataxins (1, 2, 3, 7) Atrophin Androgen receptor | Huntington's disease Spinocerebellar ataxias (SCA1, 2, 3, 7) Dentatorubropallidoluysian atrophy (DRPLA) Spinal and bulbar muscular atrophy | N-terminal of protein with expanded glutamine repeats Proteins with expanded glutamine repeats Proteins with expanded glutamine repeats Proteins with expanded glutamine repeats | 40 | DiFiglia et al. (1997) Paulson et al. (2000) Paulson et al. (2000) Paulson et al. (2000) |
| Neuroserpin | Familial encephalopathy with neuronal inclusion bodies (FENIB) | Neuroserpin: S49P, S92R | 57 | Davis et al. (1999) |
| α-Synuclein | Parkinson's disease, dementia with Lewy bodies, multiple system atrophy | *Inherited and sporadic forms* A53T, A30P in rare autosomal-dominant PD families | 19 | Spillantini et al. (1998) Polymeropoulos et al. (1997) |
| Cystatin C | Hereditary cerebral angiopathy (Icelandic) | Cystatin C less 10 residues; L68Q | 12-13 | Abrahamson et al. (1992) |
| Superoxide dismutase 1 | Amyotrophic lateral sclerosis | SOD1 mutations | | Shibata et al. (1996) |
| *Non-neurodegenerative disorders* | | | | |
| Haemoglobin | Sickle cell anaemia Inclusion body haemolysis | Haemoglobin beta chain (S) Many mutations | | Carrell & Gooptu (1998) |
| Serpins | α1-Antitrypsin deficiency (emphysema, cirrhosis) Antithrombin deficiency (thromboembolic disease) C1-inhibitor deficiency (angioedema) | Mutations Mutations Mutations | | Lomas et al. (1992) Carrell & Gooptu (1998) Carrell & Gooptu (1998) |
| Immunoglobulin light chain | Plasma cell dyscrasias (primary systemic AL amyloidosis) | Light chain or fragments | 0.5-25 | Westermark et al. (1995) |
| Serum amyloid A | Reactive, secondary systemic AA amyloidosis Chronic inflammatory disease | Variable N-terminal fragments of SAA | 4.5-10 | Westermark et al. (1995) |

| Protein | Disease | Form | Size (kDa) | Reference |
|---|---|---|---|---|
| Transthyretin | Familial amyloid polyneuropathy (systemic; FAP I) | Tetramer dissociated to conformational monomer variant. Many mutations (some not associated with amyloid; several different types of disease) | 10-14 | Gustavsson et al. (1991) |
| | Senile cardiac amyloidosis | Normal transthyretin | 10-14 | Gustavsson et al. (1991) |
| Gelsolin | Familial amyloidosis - Finnish type (FAP IV) | D187Q leads to truncated 173-225/243 (critical residues 182-192) | 9.5 | Maury & Baumann (1990) |
| β2-Microglobulin | Haemodialysis amyloidosis<br>Prostatic amyloid | β2-Microglobulin | 12-25 | Gorevic et al. (1985) |
| Apolipoprotein AI | Familial amyloid polyneuropathy (systemic; FAP III) | N-terminal 83-93 residues; G26R, W50R, L60R | 9 | Booth et al. (1995) |
| Lysozyme | Familial visceral amyloidosis | Lysozyme or fragments (with or without I56T, D67H) | 14 | Pepys et al. (1993) |
| Amylin (Islet amyloid polypeptide) | Type II diabetes (NIDDM) | Fragments (critical core of 20-29); no mutations | 3.9 | Westermark (1990) |
| Fibrinogen α-chain | Hereditary renal amyloidosis | Fibrinogen fragments | 7-10 | Uemichi et al. (1994) |
| Procalcitonin | Medullary carcinoma of thyroid | Calcitonin fragments | 3.4 | Sletten et al. (1976) |
| Atrial natriuretic factor | Cardiac amyloidosis | ANF, no mutants | 3.5 | Johansson et al. (1987) |
| Insulin | Injection localised amyloidosis | Insulin | | Dische et al. (1988) |
| Other proteins forming amyloid | (in vitro) | Other proteins | | Chiti et al. (1999) |

Figure 5B

```
ATG GCT GAG CCC CGC CAG GAG TTC GAA GTG ATG GAA GAT CAC GCT GGG
Met Ala Glu Pro Arg Gln Glu Phe Glu Val Met Glu Asp His Ala Gly
 1           5                       10                      15
ACG TAC GGG TTG GGG GAC AGG AAA GAT CAG GGG GGC TAC ACC ATG CAC
Thr Tyr Gly Leu Gly Asp Arg Lys Asp Gln Gly Gly Tyr Thr Met His
                20                  25                      30
CAA GAC CAA GAG GGT GAC ACG GAC GCT GGC CTG AAA GAA TCT CCC CTG
Gln Asp Gln Glu Gly Asp Thr Asp Ala Gly Leu Lys Glu Ser Pro Leu
            35                      40                  45
CAG ACC CCC ACT GAG GAC GGA TCT GAG GAA CCG GGC TCT GAA ACC TCT
Gln Thr Pro Thr Glu Asp Gly Ser Glu Glu Pro Gly Ser Glu Thr Ser
        50                      55                  60
GAT GCT AAG AGC ACT CCA ACA GCG GAA GAT GTG ACA GCA CCC TTA GTG
Asp Ala Lys Ser Thr Pro Thr Ala Glu Asp Val Thr Ala Pro Leu Val
65                  70                      75                  80
GAT GAG GGA GCT CCC GGC AAG CAG GCT GCC GCG CAG CCC CAC ACG GAG
Asp Glu Gly Ala Pro Gly Lys Gln Ala Ala Ala Gln Pro His Thr Glu
                85                      90                  95
ATC CCA GAA GGA ACC ACA GCT GAA GAA GCA GGC ATT GGA GAC ACC CCC
Ile Pro Glu Gly Thr Thr Ala Glu Glu Ala Gly Ile Gly Asp Thr Pro
            100                     105                 110
AGC CTG GAA GAC GAA GCT GCT GGT CAC GTG ACC CAA GCT CGC ATG GTC
Ser Leu Glu Asp Glu Ala Ala Gly His Val Thr Gln Ala Arg Met Val
        115                     120                 125
AGT AAA AGC AAA GAC GGG ACT GGA AGC GAT GAC AAA AAA GCC AAG GGG
Ser Lys Ser Lys Asp Gly Thr Gly Ser Asp Asp Lys Lys Ala Lys Gly
    130                     135                 140
GCT GAT GGT AAA ACG AAG ATC GCC ACA CCG CGG GGA GCA GCC CCT CCA
Ala Asp Gly Lys Thr Lys Ile Ala Thr Pro Arg Gly Ala Ala Pro Pro
145                 150                 155                 160
GGC CAG AAG GGC CAG GCC AAC GCC ACC AGG ATT CCA GCA AAA ACC CCG
Gly Gln Lys Gly Gln Ala Asn Ala Thr Arg Ile Pro Ala Lys Thr Pro
                165                 170                 175
CCC GCT CCA AAG ACA CCA CCC AGC TCT GGT GAA CCT CCA AAA TCA GGG
Pro Ala Pro Lys Thr Pro Pro Ser Ser Gly Glu Pro Pro Lys Ser Gly
            180                 185                 190
GAT CGC AGC GGC TAC AGC AGC CCC GGC TCC CCA GGC ACT CCC GGC AGC
Asp Arg Ser Gly Tyr Ser Ser Pro Gly Ser Pro Gly Thr Pro Gly Ser
        195                 200                 205
CGC TCC CGC ACC CCG TCC CTT CCA ACC CCA CCC ACC CGG GAG CCC AAG
Arg Ser Arg Thr Pro Ser Leu Pro Thr Pro Pro Thr Arg Glu Pro Lys
    210                 215                 220
```

Figure 7A

```
AAG GTG GCA GTG GTC CGT ACT CCA CCC AAG TCG CCG TCT TCC GCC AAG
Lys Val Ala Val Val Arg Thr Pro Pro Lys Ser Pro Ser Ser Ala Lys
225             230             235             240
AGC CGC CTG CAG ACA GCC CCC GTG CCC ATG CCA GAC CTG AAG AAT GTC
Ser Arg Leu Gln Thr Ala Pro Val Pro Met Pro Asp Leu Lys Asn Val
            245             250             255
AAG TCC AAG ATC GGC TCC ACT GAG AAC CTG AAG CAC CAG CCG GGA GGC
Lys Ser Lys Ile Gly Ser Thr Glu Asn Leu Lys His Gln Pro Gly Gly
            260             265             270
GGG AAG GTG CAG ATA ATT AAT AAG AAG CTG GAT CTT AGC AAC GTC CAG
Gly Lys Val Gln Ile Ile Asn Lys Lys Leu Asp Leu Ser Asn Val Gln
        275             280             285
TCC AAG TGT GGC TCA AAG GAT AAT ATC AAA CAC GTC CCG GGA GGC GGC
Ser Lys Cys Gly Ser Lys Asp Asn Ile Lys His Val Pro Gly Gly Gly
        290             295             300
AGT GTG CAA ATA GTC TAC AAA CCA GTT GAC CTG AGC AAG GTG ACC TCC
Ser Val Gln Ile Val Tyr Lys Pro Val Asp Leu Ser Lys Val Thr Ser
305             310             315             320
AAG TGT GGC TCA TTA GGC AAC ATC CAT CAT AAA CCA GGA GGT GGC CAG
Lys Cys Gly Ser Leu Gly Asn Ile His His Lys Pro Gly Gly Gly Gln
            325             330             335
GTG GAA GTA AAA TCT GAG AAG CTT GAC TTC AAG GAC AGA GTC CAG TCG
Val Glu Val Lys Ser Glu Lys Leu Asp Phe Lys Asp Arg Val Gln Ser
            340             345             350
AAG ATT GGG TCC CTG GAC AAT ACC ATC CAC GTC CCT GGC GGA GGA AAT
Lys Ile Gly Ser Leu Asp Asn Thr Ile His Val Pro Gly Gly Gly Asn
            355             306             365
AAA AAG ATT GAA ACC CAC AAG CTG ACC TTC CGC GAG AAC GCC AAA GCC
Lys Lys Ile Glu Thr His Lys Leu Thr Phe Arg Glu Asn Ala Lys Ala
370             375             380
AAG ACA GAC CAC GGG GCG GAG ATC GTG TAC AAG TCG CCA GTG GTG TCT
Lys Thr Asp His Gly Ala Glu Ile Val Tyr Lys Ser Pro Val Val Ser
385             390             395             400
GGG GAC ACG TCT CCA CGG CAT CTC AGC AAT GTC TCC TCC ACC GGC AGC
Gly Asp Thr Ser Pro Arg His Leu Ser Asn Val Ser Ser Thr Gly Ser
            405             410             415
ATC GAC ATG GTA GAC TCG CCC CAG CTC GCC ACG CTA GCT GAC GAG GTG
Ile Asp Met Val Asp Ser Pro Gln Leu Ala Thr Leu Ala Asp Glu Val
            420             425             430
TCT GCC TCC CTG GCC AAG CAG GGT TTG TGA
Ser Ala Ser Leu Ala Lys Gln Gly Leu ***
            435             440
```

Figure 7B

Compounds tested in cell-based assays
Thionine
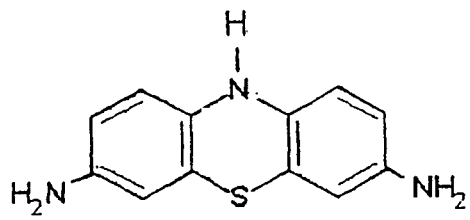
Tolonium Chloride
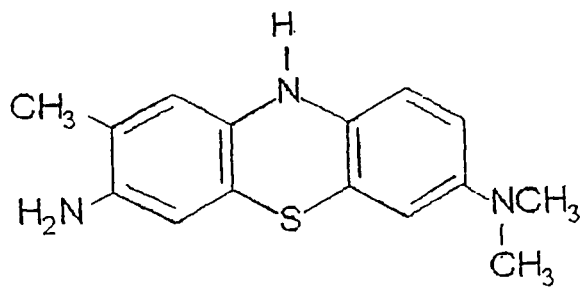
Tacrine
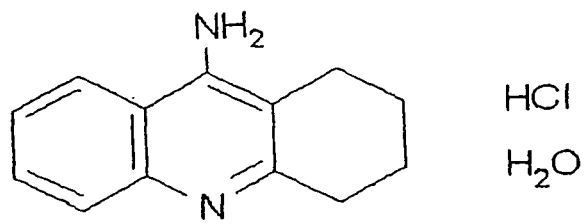
Chlorpromazine
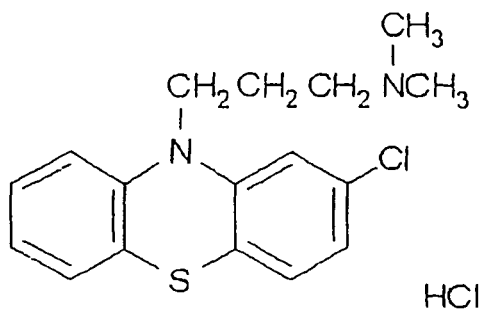
Figure 8

| | KI (nM) | B$_{50}$ (μM) |
|---|---|---|
| I Reduced Thionine | 100 | 2.17 |
| Oxidised Thionine | 1200 | 26.07 |
| Reduced Tolonium Chloride | 105 | 2.28 |
| Reduced Methylene Blue | 123 | 2.67 |
| DH12 | — | — |

Figure 9

| | |
|---|---|
| Observed vs predicted activity | r = 0.986 |
| Intracellular tau concentration | 500 nM |
| Tau-tau binding affinity | 22 nM |
| Thionine KI | 100 nM |

| Observed vs predicted activity | r = 0.784 |
| --- | --- |
| Intracellular tau concentration | 500 nM |
| Tau-tau binding affinity | 22 nM |
| Oxidised Thionine KI | 1200 nm |

| Observed vs predicted activity | r = 0.962 |
| --- | --- |
| Intracellular tau concentration | 500 nM |
| Tau-tau binding affinity | 22 nM |
| Methylene Blue KI | 123 nM |

| Observed vs predicted activity | r = 0.913 |
| --- | --- |
| Intracellular tau concentration | 500 nM |
| Tau-tau binding affinity | 22 nM |
| Tolonium Chloride KI | 105 nM |

| | |
|---|---|
| Observed vs predicted activity | r = 0.937 |
| Intracellular tau concentration | 415 nM |
| Tau-tau binding affinity | 22 nM |
| Chlorpromazine KI | 2117 nm |

| Observed vs predicted activity | r = 0.976 |
| --- | --- |
| Intracellular tau concentration | 415 nM |
| Tau-tau binding affinity | 22 nM |
| Tacrine KI | 802 nm |

Tissue levels vs IV dose of MB
DiSanto and Wagner (1972)

| Length of tau | Apparent Mr (kDa) | Expression in: | |
|---|---|---|---|
| | | 3T3 | COS-7 |
| 1) 1-391 | 55 | ++ | ++++ |
| 2) m186-391 | 26 | ++ | ++++ |
| 3) m297-391 | 12 | +/- | + |
| 4) m186-441 | 32 | ++ | +++ |
| 5) m297-441 | 18 | + | + |
| 6) 1-441 | 67 | ++ | ++++ |
| 7) [kozak]m295-391 | 12 | + | +++ |
| 8) [kozak]m297-391 | 12 | +/- | ++ |

Figure 20

RANK ORDER OF POTENCY (KI)

REDUCED FORMS

| Compound | Structure | KI |
|---|---|---|
| Tolonium Chloride | 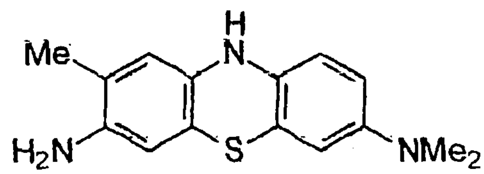 | 76.05 |
| Thionine | 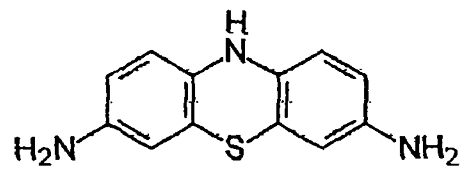 | 108.34 |
| Azure A | 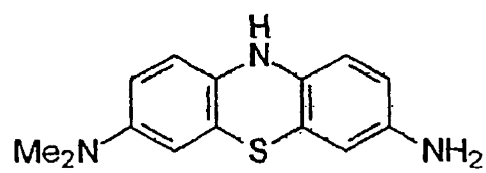 | 119.01 |
| Azure B | 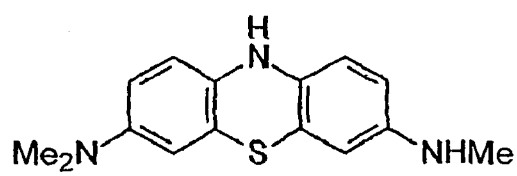 | 123.91 |
| 1,9-Dimethyl-methylene blue | 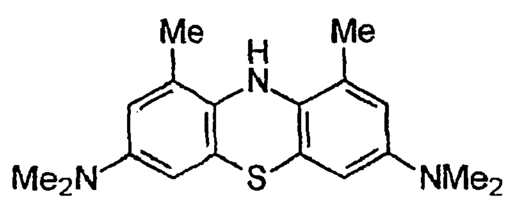 | 325.41 |
| Methylene Blue | 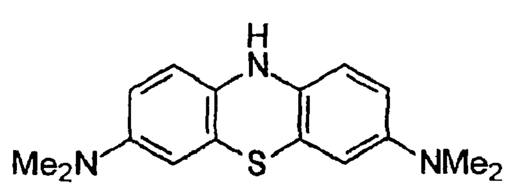 | 3731.26 |

Figure 25

STB = mean binding for 1 & 10 µg/ml of compound

LB50 = log10 molar ratio of compound:tau producing 50% binding

Relationship between STB and B50 values (molar ratio of compound:tau at which tau-tau binding is reduced by 50%)

| Compound | STB | B50 |
| --- | --- | --- |
| Tolonium Chloride | 0.190 | 2.86 |
| Thionine | 0.201 | 4.06 |
| Azure A | 0.227 | 4.49 |
| Azure B | 0.269 | 4.46 |
| Dimethyl MB | 0.372 | 12 |
| Vitamin K | 0.674 | 48 |
| Neutral red | 0.787 | 56 |
| Pyronin Y | 0.783 | 104 |
| Primulin | 0.788 | 109 |
| Acraflavin | 0.583 | 132 |
| Methylene blue (MB) | 0.992 | 150 |
| Phenothiazine | 1.040 | 508 |
| Gallocyanin | 0.997 | 608 |
| Thiazin red | 0.929 | 1419 |

Figure 30

The LB50 value is an alternative representation of the KI value where this can be determined for the diaminophenothiazines LB50 = ( 1.019 * Log( KI) ) - 1.471

Number of methyl groups vs Reduction potential and Diffusion coefficient

R = 0.947

Inhibitory potency is not determined by Reduction Potential

Potency appears to be associated with the aggregation efficiency of the reduced form Approximation of LB50 values as function of reduction potential and diffusion coefficient DERIVATION OF OBSERVED FRAGMENTS FROM PROTEOLYTIC PROCESSING OF HEPTAMERIC AGGREGATE

| | AA | KD | 342 | T46 |
|---|---|---|---|---|
| 164 — 441 | 277 | 44 | + | + |
| 164 — 424 | 260 | 42 | + | - |
| 164 — 407 | 243 | 38 | + | - |
| 198 — 441 | 243 | 38 | + | + |
| 232 — 441 | 209 | 32 | - | + |
| 266 — 441 | 175 | 27 | - | + |
| 181 — 441 | 260 | 42 | + | + |
| 181 — 424 | 243 | 38 | + | - |
| 181 — 407 | 226 | 36 | + | - |
| 215 — 441 | 226 | 36 | +/- | + |
| 249 — 441 | 192 | 30 | - | + |
| 283 — 441 | 158 | 25 | - | + |
| 198 — 441 | 243 | 38 | + | + |
| 198 — 424 | 226 | 36 | + | - |
| 198 — 407 | 209 | 32 | + | - |
| 232 — 441 | 209 | 32 | - | + |
| 266 — 441 | 175 | 27 | - | + |
| 441 — 249 | 192 | 30 | - | + |
| 441 — 266 | 175 | 27 | - | + |
| 441 — 283 | 158 | 25 | - | + |
| 441 — 215 | 226 | 36 | +/- | + |
| 441 — 232 | 209 | 32 | - | + |
| 441 — 249 | 192 | 30 | - | + |
| 441 — 181 | 260 | 42 | + | + |
| 424 — 181 | 243 | 38 | + | - |
| 441 — 198 | 243 | 38 | + | + |
| 424 — 198 | 226 | 36 | + | - |
| 441 — 215 | 226 | 36 | +/- | + |
| 424 — 215 | 209 | 32 | +/- | - |

Figure 44

FRAGMENTS DERIVED FROM PROTEOLYTIC PROCESSING OF HEPTAMERIC AGGREGATE

| Fragment | AA | KD | 342 | T46 |
|---|---|---|---|---|
| 164–441 | 277 | 44 | + | + |
| 164–424 | 260 | 42 | + | − |
| 181–441 | 260 | 42 | + | + |
| 164–407 | 243 | 38 | + | − |
| 181–424 | 243 | 38 | + | − |
| 198–441 | 243 | 38 | + | + |
| 181–407 | 226 | 36 | + | − |
| 215–441 | 226 | 36 | +/− | + |
| 198–424 | 226 | 36 | + | − |
| 198–407 | 209 | 32 | + | − |
| 232–441 | 209 | 32 | − | + |
| 424–215 | 209 | 32 | +/− | − |
| 249–441 | 192 | 30 | − | + |
| 266–441 | 175 | 27 | − | + |
| 283–441 | 158 | 25 | − | + |

| Observed vs predicted activity | r = 1.00 |
|---|---|
| Intracellular tau concentration | 500 nM |
| Tau-tau binding affinity | 22 nM |
| DMMB KI | 4.4 nM |
| DMMB B50 | 100 nM |

SEQUENCE LISTING

```
<160> NUMBER OF SEQ ID NOS: 8

<210> SEQ ID NO 1
<211> LENGTH: 1326
<212> TYPE: DNA
<213> ORGANISM: Homo sapiens
<220> FEATURE:
<221> NAME/KEY: CDS
<222> LOCATION: (1)..(1326)

<400> SEQUENCE: 1
```

-continued

| | |
|---|---|
| atg gct gag ccc cgc cag gag ttc gaa gtg atg gaa gat cac gct ggg<br>Met Ala Glu Pro Arg Gln Glu Phe Glu Val Met Glu Asp His Ala Gly<br>1                5                      10                 15 | 48 |
| acg tac ggg ttg ggg gac agg aaa gat cag ggg ggc tac acc atg cac<br>Thr Tyr Gly Leu Gly Asp Arg Lys Asp Gln Gly Gly Tyr Thr Met His<br>                20                    25                  30 | 96 |
| caa gac caa gag ggt gac acg gac gct ggc ctg aaa gaa tct ccc ctg<br>Gln Asp Gln Glu Gly Asp Thr Asp Ala Gly Leu Lys Glu Ser Pro Leu<br>        35                    40                  45 | 144 |
| cag acc ccc act gag gac gga tct gag gaa ccg ggc tct gaa acc tct<br>Gln Thr Pro Thr Glu Asp Gly Ser Glu Glu Pro Gly Ser Glu Thr Ser<br>50                      55                  60 | 192 |
| gat gct aag agc act cca aca gcg gaa gat gtg aca gca ccc tta gtg<br>Asp Ala Lys Ser Thr Pro Thr Ala Glu Asp Val Thr Ala Pro Leu Val<br>65                 70                 75                 80 | 240 |
| gat gag gga gct ccc ggc aag cag gct gcc gcg cag ccc cac acg gag<br>Asp Glu Gly Ala Pro Gly Lys Gln Ala Ala Ala Gln Pro His Thr Glu<br>                85                    90                  95 | 288 |
| atc cca gaa gga acc aca gct gaa gaa gca ggc att gga gac acc ccc<br>Ile Pro Glu Gly Thr Thr Ala Glu Glu Ala Gly Ile Gly Asp Thr Pro<br>                100                  105                110 | 336 |
| agc ctg gaa gac gaa gct gct ggt cac gtg acc caa gct cgc atg gtc<br>Ser Leu Glu Asp Glu Ala Ala Gly His Val Thr Gln Ala Arg Met Val<br>            115                  120                125 | 384 |
| agt aaa agc aaa gac ggg act gga agc gat gac aaa aaa gcc aag ggg<br>Ser Lys Ser Lys Asp Gly Thr Gly Ser Asp Asp Lys Lys Ala Lys Gly<br>            130                  135                140 | 432 |
| gct gat ggt aaa acg aag atc gcc aca ccg cgg gga gca gcc cct cca<br>Ala Asp Gly Lys Thr Lys Ile Ala Thr Pro Arg Gly Ala Ala Pro Pro<br>145                   150                  155                160 | 480 |
| ggc cag aag ggc cag gcc aac gcc acc agg att cca gca aaa acc ccg<br>Gly Gln Lys Gly Gln Ala Asn Ala Thr Arg Ile Pro Ala Lys Thr Pro<br>                  165                  170                175 | 528 |
| ccc gct cca aag aca cca ccc agc tct ggt gaa cct cca aaa tca ggg<br>Pro Ala Pro Lys Thr Pro Pro Ser Ser Gly Glu Pro Pro Lys Ser Gly<br>            180                  185                190 | 576 |
| gat cgc agc ggc tac agc agc ccc ggc tcc cca ggc act ccc ggc agc<br>Asp Arg Ser Gly Tyr Ser Ser Pro Gly Ser Pro Gly Thr Pro Gly Ser<br>                195                  200                205 | 624 |
| cgc tcc cgc acc ccg tcc ctt cca acc cca ccc acc cgg gag ccc aag<br>Arg Ser Arg Thr Pro Ser Leu Pro Thr Pro Pro Thr Arg Glu Pro Lys<br>            210                  215                220 | 672 |
| aag gtg gca gtg gtc cgt act cca ccc aag tcg ccg tct tcc gcc aag<br>Lys Val Ala Val Val Arg Thr Pro Pro Lys Ser Pro Ser Ser Ala Lys<br>225                   230                  235                240 | 720 |
| agc cgc ctg cag aca gcc ccc gtg ccc atg cca gac ctg aag aat gtc<br>Ser Arg Leu Gln Thr Ala Pro Val Pro Met Pro Asp Leu Lys Asn Val<br>                245                  250                255 | 768 |
| aag tcc aag atc ggc tcc act gag aac ctg aag cac cag ccg gga ggc<br>Lys Ser Lys Ile Gly Ser Thr Glu Asn Leu Lys His Gln Pro Gly Gly<br>            260                  265                270 | 816 |
| ggg aag gtg cag ata att aat aag aag ctg gat ctt agc aac gtc cag<br>Gly Lys Val Gln Ile Ile Asn Lys Lys Leu Asp Leu Ser Asn Val Gln<br>            275                  280                285 | 864 |
| tcc aag tgt ggc tca aag gat aat atc aaa cac gtc ccg gga ggc ggc<br>Ser Lys Cys Gly Ser Lys Asp Asn Ile Lys His Val Pro Gly Gly Gly<br>        290                  295                300 | 912 |
| agt gtg caa ata gtc tac aaa cca gtt gac ctg agc aag gtg acc tcc<br>Ser Val Gln Ile Val Tyr Lys Pro Val Asp Leu Ser Lys Val Thr Ser | 960 |

```
                305                 310                 315                 320
aag tgt ggc tca tta ggc aac atc cat cat aaa cca gga ggt ggc cag        1008
Lys Cys Gly Ser Leu Gly Asn Ile His His Lys Pro Gly Gly Gly Gln
                325                 330                 335 gtg gaa gta aaa tct gag aag ctt gac ttc aag gac aga gtc cag tcg        1056
Val Glu Val Lys Ser Glu Lys Leu Asp Phe Lys Asp Arg Val Gln Ser
                340                 345                 350 aag att ggg tcc ctg gac aat atc acc cac gtc cct ggc gga gga aat        1104
Lys Ile Gly Ser Leu Asp Asn Ile Thr His Val Pro Gly Gly Gly Asn
                355                 360                 365 aaa aag att gaa acc cac aag ctg acc ttc cgc gag aac gcc aaa gcc        1152
Lys Lys Ile Glu Thr His Lys Leu Thr Phe Arg Glu Asn Ala Lys Ala
                370                 375                 380 aag aca gac cac ggg gcg gag atc gtg tac aag tcg cca gtg gtg tct        1200
Lys Thr Asp His Gly Ala Glu Ile Val Tyr Lys Ser Pro Val Val Ser
385                 390                 395                 400 ggg gac acg tct cca cgg cat ctc agc aat gtc tcc tcc acc ggc agc        1248
Gly Asp Thr Ser Pro Arg His Leu Ser Asn Val Ser Ser Thr Gly Ser
                405                 410                 415 atc gac atg gta gac tcg ccc cag ctc gcc acg cta gct gac gag gtg        1296
Ile Asp Met Val Asp Ser Pro Gln Leu Ala Thr Leu Ala Asp Glu Val
                420                 425                 430 tct gcc tcc ctg gcc aag cag ggt ttg tga                                1326
Ser Ala Ser Leu Ala Lys Gln Gly Leu
                435                 440

<210> SEQ ID NO 2
<211> LENGTH: 441
<212> TYPE: PRT
<213> ORGANISM: Homo sapiens

<400> SEQUENCE: 2

Met Ala Glu Pro Arg Gln Glu Phe Glu Val Met Glu Asp His Ala Gly
 1               5                  10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Pro Lys Ser Gly
            180                 185                 190

Asp Arg Ser Gly Tyr Ser Ser Pro Gly Ser Pro Gly Thr Pro Gly Ser
```

```
                195                 200                 205
Arg Ser Arg Thr Pro Ser Leu Pro Thr Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
            245                 250                 255

Lys Ser Lys Ile Gly Ser Thr Glu Asn Leu Lys His Gln Pro Gly Gly
        260                 265                 270

Gly Lys Val Gln Ile Ile Asn Lys Lys Leu Asp Leu Ser Asn Val Gln
    275                 280                 285

Ser Lys Cys Gly Ser Lys Asp Asn Ile Lys His Val Pro Gly Gly Gly
290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
            325                 330                 335

Val Glu Val Lys Ser Glu Lys Leu Asp Phe Lys Asp Arg Val Gln Ser
        340                 345                 350

Lys Ile Gly Ser Leu Asp Asn Ile Thr His Val Pro Gly Gly Gly Asn
    355                 360                 365

Lys Lys Ile Glu Thr His Lys Leu Thr Phe Arg Glu Asn Ala Lys Ala
370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
            405                 410                 415

Ile Asp Met Val Asp Ser Pro Gln Leu Ala Thr Leu Ala Asp Glu Val
        420                 425                 430

Ser Ala Ser Leu Ala Lys Gln Gly Leu
    435                 440

<210> SEQ ID NO 3
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 3
gtcgactcta gaggcggccg catggctgag ccccggcagg ag                      42

<210> SEQ ID NO 4
<211> LENGTH: 45
<212> TYPE: DNA
<213> ORGANISM: Artificial Sequence
<220> FEATURE:
<223> OTHER INFORMATION: Description of Artificial Sequence: Primer

<400> SEQUENCE: 4
actcttaagg gtcgcggccg ctcacaacaa accctgcttg gccag                   45

<210> SEQ ID NO 5
<211> LENGTH: 291
<212> TYPE: DNA
<213> ORGANISM: Homo sapiens

<400> SEQUENCE: 5
```

```
gataatatca aacacgtccc gggaggcggc agtgtgcaaa tagtctacaa accagttgac    60
ctgagcaagg tgacctccaa gtgtggctca ttaggcaaca tccatcataa accaggaggt   120
ggccaggtgg aagtaaaatc tgagaagctt gacttcaagg acagagtcca gtcgaagatt   180
gggtccctgg acaatatcac ccacgtccct ggcggaggaa ataaaaagat tgaaacccac   240
aagctgacct ccgcgagaa cgccaaagcc aagacagacc acggggcgga g            291

<210> SEQ ID NO 6
<211> LENGTH: 97
<212> TYPE: PRT
<213> ORGANISM: Homo sapiens

<400> SEQUENCE: 6

Asp Asn Ile Lys His Val Pro Gly Gly Gly Ser Val Gln Ile Val Tyr
  1               5                  10                  15

Lys Pro Val Asp Leu Ser Lys Val Thr Ser Lys Cys Gly Ser Leu Gly
             20                  25                  30

Asn Ile His His Lys Pro Gly Gly Gly Gln Val Glu Val Lys Ser Glu
         35                  40                  45

Lys Leu Asp Phe Lys Asp Arg Val Gln Ser Lys Ile Gly Ser Leu Asp
     50                  55                  60

Asn Ile Thr His Val Pro Gly Gly Gly Asn Lys Lys Ile Glu Thr His
 65                  70                  75                  80

Lys Leu Thr Phe Arg Glu Asn Ala Lys Ala Lys Thr Asp His Gly Ala
                 85                  90                  95

Glu

<210> SEQ ID NO 7
<211> LENGTH: 36
<212> TYPE: DNA
<213> ORGANISM: Artificial Sequence
<220> FEATURE:
<223> OTHER INFORMATION: Description of Artificial Sequence: Primer

<400> SEQUENCE: 7
cggaattcca ccatggataa tatcaaacac gtcccg                              36

<210> SEQ ID NO 8
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 8
cgcgggatcc tcactccgcc ccgtggtctg tcttggc                             37
```

MATERIALS AND METHODS RELATING TO PROTEIN AGGREGATION IN NEURODEGENERATIVE DISEASE

CROSS-REFERENCE TO RELATED APPLICATION

This application is a continuation of U.S. patent application Ser. No. 10/451,782, filed on Dec. 8, 2003, which issued as U.S. Pat. No. 7,335,505, on Feb. 26, 2008; which is the National Phase Application of International Application PCT/GB02/00153 filed on Jan. 15, 2002, which published in English as WO 02/055720 on Jul. 18, 2002; and claims the benefit of the filing date of Great Britain Provisional Application No. GB 0101049, filed Jan. 15, 2001.

TECHNICAL FIELD

The present invention concerns cell-based models and other test systems for modelling the aggregation of proteins associated with neurodegenerative disease. It further relates to compounds capable of modulating such aggregation.

BACKGROUND ART

Conditions of dementia such as Alzheimer's disease (AD) are frequently characterised by a progressive accumulation of intracellular and/or extracellular deposits of proteinaceous structures such as β-amyloid plaques and neurofibrillary tangles in the brains of affected patients. The appearance of these lesions largely correlates with pathological neurofibrillary degeneration and brain atrophy, as well as with cognitive impairment (Mukaetova-Ladinska, E. B. et al. (2000) Am. J. Pathol. Vol. 157, No. 2, 623-636).

Both neuritic plaques and neurofibrillary tangles contain paired helical filaments (PHFs), of which a major constituent is the microtubule-associated protein tau (Wischik et al. (1988) PNAS USA 85, 4506). Plaques also contain extracellular β-amyloid fibrils derived from the abnormal processing of amyloid precursor protein (APP; Kang et al. (1987) Nature 325, 733). An article by Wischik et al. (in 'Neurobiology of Alzheimer's Disease', 2nd Edition (2000) Eds. Dawbarn, D. and Allen, S. J., The Molecular and Cellular Neurobiology Series, Bios Scientific Publishers, Oxford) discusses in detail the putative role of tau protein in the pathogenesis of neurodegenerative dementias.

Studies of Alzheimer's disease indicate that the loss of the normal form of tau (Mukaetova-Ladinska et al. (1993) Am. J. Pathol., 143, 565; Wischik et al. (1995a) Neurobiol. Ageing, 16: 409; Lai et al. (1995b) Neurobiol. Ageing, 16: 433), accumulation of pathological PHFs (Mukaetova-Ladinska et al. (1993), loc. cit.; Harrington et al. (1994a) Dementia, 5, 215; Harrington et al. (1994b) Am. J. Pathol., 145, 1472; Wischik et al., (1995a), loc. cit.) and loss of synapses in the mid-frontal cortex (Terry et al. (1991) Ann. Neurol., 30, 572) correlate with associated cognitive impairment. Furthermore, loss of synapses (Terry et al., loc. cit.) and loss of pyramidal cells (Bondareff et al. (1993) Arch. Gen. Psychiatry, 50: 350) both correlate with morphometric measures of tau-reactive neurofibrillary pathology, which parallels, at a molecular level, an almost total redistribution of the tau protein pool from a soluble to a polymerised form (PHFs) in Alzheimer's disease (Mukaetova-Ladinska et al. (1993), loc. cit.; Lai et al. (1995), loc. cit.).

Tau exists in alternatively-spliced isoforms, which contain three or four copies of a repeat sequence corresponding to the microtubule-binding domain (Goedert, M., et al. (1989) EMBO J. 8, 393-399; Goedert, M., et al. (1989) Neuron 3, 519-526). Tau in PHFs is proteolytically processed to a core domain (Wischik, C. M., et al. (1988) Proc. Natl. Acad. Sci. USA 85, 4884-4888; Wischik et al. PNAS USA 1988, 85:4506-4510); Novak, M., et al. (1993) EMBO J. 12, 365-370) which is composed of a phase-shifted version of the repeat domain; only three repeats are involved in the stable tau-tau interaction (Jakes, R., et al. (1991) EMBO J. 10, 2725-2729). Once formed, PHF-like tau aggregates act as seeds for the further capture and provide a template for proteolytic processing of full-length tau protein (Wischik et al. 1996 Proc Natl Acad Sci USA 93, 11213-11218).

In the course of their formation and accumulation, paired helical filaments (PHFs) first assemble to form amorphous aggregates within the cytoplasm, probably from early tau oligomers which become truncated prior to, or in the course of, PHF assembly (Mena, R., et al. (1995) Acta Neuropathol. 89, 50-56; Mena, R., et al. (1996) Acta Neuropathol. 91, 633-641). These filaments then go on to form classical intracellular neurofibrillary tangles. In this state, the PHFs consist of a core of truncated tau and a fuzzy outer coat containing full-length tau (Wischik, C. M., et al, (1996) loc. cit.). The assembly process is exponential, consuming the cellular pool of normal functional tau and inducing new tau synthesis to make up the deficit (Lai, R. Y. K., et al., (1995), Neurobiology of Ageing, Vol. 16, No. 3, 433-445). Eventually, functional impairment of the neurone progresses to the point of cell death, leaving behind an extracellular tangle. Cell death is highly correlated with the number of extracellular tangles (Wischik et al. 2000, loc.cit). As tangles are extruded into the extracellular space, there is progressive loss of the fuzzy outer coat of the neurone-PHF with corresponding loss of N-terminal tau immunoreactivity, but preservation of tau immunoreactivity associated with the PHF core (FIG. 1; also Bondareff, W. et al., (1994) J. Neuropath. Exper. Neurol., Vol. 53, No. 2, 158-164).

The phase shift which is observed in the repeat domain of tau incorporated into PHFs suggests that the repeat domain undergoes an induced conformational change during incorporation into the filament. During the onset of Alzheimer's disease, it is envisaged that this conformational change could be initiated by the binding of tau to a pathological substrate, such as damaged or mutated membrane proteins (see FIG. 2—also Wischik, C. M., et al. (1997) in "*Microtubule-associated proteins: modifications in disease*", eds. Avila, J., Brandt, R. and Kosik, K. S. (Harwood Academic Publishers, Amsterdam) pp. 185-241).

In the case of Alzheimer's disease, current pharmaceutical therapies are focused on symptomatic treatment of the loss of cholinergic transmission which results from neurodegeneration (Mayeux, R., et al. (1999) New Eng. J. Med. 341, 1670-1679). However, although the available treatments delay progression of the disease for up to six to twelve months, they do not prevent it. The discovery of drugs that could prevent the aggregation of tau which leads to neurodegeneration would provide a more effective strategy for prophylaxis or for inhibiting the progression of the disease, which would not require an immediate knowledge of the diverse upstream events that initiate the aggregation (see FIG. 3).

Models and Assays

WO 96/30766 describes an in vitro assay for tau aggregation in which a fragment of tau corresponding to the core repeat domain, which has been adsorbed to a solid phase substrate, is able to capture soluble full-length tau and bind tau with high affinity (see FIG. 4). This association confers stability against digestion of proteases on the tau molecules on the repeat domains of tau molecules which have aggregated. The process is self-propagating, and can be blocked selectively by prototype pharmaceutical agents ((Wischik et al. 1996 Proc Natl Acad Sci USA 93, 11213-11218).

Although the in vitro assay described in WO 96/30766 enables the identification of inhibitors or modulators of tau-tau association, the present inventors have also recognized that cell-based models of Alzheimer's disease-like protein aggregation would be useful. Such cellular models could be used both in the primary screening of candidate modulators of tau-tau aggregation, and in the secondary screening of compounds already identified in the in vitro assay of WO 96/30766. Furthermore, the demonstration of tau aggregation in cells could also aid in the identification of normal cellular substrates which are involved in the initiation of pathological tau aggregation, which substrates could themselves be targets for pharmaceutical intervention.

However, numerous papers reporting the expression of various tau constructs in tissue culture models have failed to demonstrate aggregation (see e.g. Baum, L. et al., (1995) Mol. Brain. Res. 34:1-17). For instance, 3T3 mouse fibroblasts do not possess tau protein and thus present a cellular environment in which recombinant tau can be expressed independent of endogenous mouse tau. Transfection of various cell lines has been reported previously (Kanai et al., 1989; Goedert and Jakes, 1990; Knops et al, 1991; Lee and Rook, 1992; Gallo et al., 1992; Lo et al., 1993; Montejo de Garcini et al., 1994; Fasulo et al., 1996). However the stable long term expression of truncated tau in such cell lines was not achieved. For example, tau constructs for residues 164 or 173 to 338 or 352 did not express protein (Lee and Rook, 1992).

Although Fasulo et al. (Alzheimer's Research 1996, 2, 195-200) reported transient expression of truncated tau in COS cells, data for stable long term expression of this tau was not shown. These workers concluded from the use of the transient transfection system that expression of truncated tau by itself was not sufficient to induce tau aggregation in a manner suitable for testing drugs.

Thus far, the aggregation of soluble tau in vitro has only been achieved under non-physiological conditions and at high concentrations (reviewed in Wischik (2000), loc. cit).

WO 96/30766 describes two approaches for studying tau aggregation in a cellular environment. In the first approach, full-length tau or fragments of tau were stably expressed in cells. In the second approach, aggregated tau was transiently transfected into cells by use of lipofectin.

Although both of these approaches are useful for the study of tau-tau aggregation, they have some limitations. Transfection of aggregated tau into cells using lipofection is of variable efficiency, as is the production in vitro of aggregated tau itself. Moreover, the core tau fragment, which is the most efficient seed for tau aggregation, is found to be toxic when stably expressed in cells, leading to low expression levels. Thus, constitutive expression of the truncated tau fragment of the PHF core in eukaryotic cells is difficult to achieve. Transient expression systems permit the optimization of expression of tau, but the inherent toxicity of the fragments renders even these systems unreliable. Longer fragments of tau are less toxic, but these do not reliably aggregate when expressed in cells.

Thus it would be desirable for an alternative model system to be developed, in which the interaction between e.g. tau molecules and the like could be investigated under physiological conditions, in a stable and controllable cell line, and which could be used to screen for potential diagnostic, prognostic or therapeutic agents of conditions such as Alzheimer's disease.

DISCLOSURE OF THE INVENTION

The present inventors have devised a stable cellular test system which can be used to model the template-driven proteolytic processing of a protein, the aggregation of which is associated with neurodegenerative disease. In one test system, exemplified with the tau protein, very low level constitutive expression of a fragment of the tau protein was combined with inducible expression of full-length tau. Induction of the full-length tau lead to its proteolytic conversion to a processed fragment, confirming that "templated proteolytic processing" of the tau was occurring. The system readily permits the demonstration of the effects of tau aggregation inhibitors through their inhibition of production of the processed, 12 kD, fragment from induced full-length tau.

That such a stable system can be achieved notwithstanding the inherent toxic properties of the 12 kD fragment is particularly surprising. For instance, as demonstrated in the Examples below, although partial truncation at either N- or C-termini of full-length tau results in cell lines in which stable expression can be maintained, these longer constructs show only a weak propensity to aggregate, rather than binding to the microtubular network. Stable expression of combinations of tau fragments generates aggregates within the cytoplasm of cells, but this system cannot be maintained reproducibly. Systems based on the inducible expression of the 12 kD fragment lead to toxicity as a result of unpredictable intracellular aggregation of the fragment.

Thus there would appear to be a trade-off in stable expression cell systems between inducing aggregation and hence toxicity on the one hand, which produces cell lines which are either variable or non-viable, and maintaining viable cell lines in which tau has a low propensity to aggregate. Notwithstanding this, the inducible tau expression system of the present invention is both stable, and yet able to provide controlled aggregation of protein for use in screens and the like.

Additionally, use of the assay has provided evidence that the mechanism of action of certain inhibitors (e.g. phenothiazines) of protein aggregation is primarily steric in nature, rather than essentially redox, as may have been suspected on the basis of the prior art. This discovery has unexpected implications for the choice, assessment, formulation and use of such compounds in the context of the diseases discussed herein. In particular, it shows that assessment of diffusion coefficients can provide a valuable screen for identifying putative inhibitors, or optimising the structure or state of known ones, because the parameters inherently assessed by measuring the diffusion coefficient may be highly relevant to the inhibitors' potency.

The assay further shows that use of phenothiazines in their reduced form can be advantageous for enhancing their inhibitory properties. These observations form the basis of further aspects of the present invention.

In general the present invention provides a method for converting, through proteolytic processing, a precursor protein to a product fragment of the precursor protein, in a stable cell line, which method comprises the steps of: (a) providing a stable cell line transfected with nucleic acid encoding (i) a template fragment of the precursor protein such that the template fragment is constitutively expressed in the cell at a level which is not toxic to the cell; and (ii) the precursor protein, which protein is inducibly expressed in the cell in response to a stimulus, whereby interaction of the template fragment with the precursor protein causes a conformational change in the precursor protein such as to cause aggregation and proteolytic processing of the precursor protein to the product fragment.

The method may include subjecting the cell to the stimulus such that the precursor protein is expressed in the cell. However in embodiments where an inducible promoter is used which causes low, but detectable levels of expression even in the absence of the stimulus, then the stimulus step may be omitted.

Generally speaking, the precursor protein will be one which, in vivo, is capable of undergoing an induced conformational polymerisation interaction (in a self-propagating manner) leading ultimately to the formation of aggregates comprised of the product fragment, and associated with the disease state. The product fragment obtained in the method provided herein is a measure of the pathological aggregation and proteolysis process which in vivo leads to the production of one or more toxic products and the disease state. The product fragment (or one or more of the fragments) of the present method may be toxic, or may simply be used as an indicator of the pathological aggregation process.

The proteins and interactions upon which the method is based are discussed in more detail below.

The present inventors have demonstrated that it is unexpectedly possible to constitutively express the template fragment at a (first) concentration which is not toxic to the cell line i.e. the cell line is viable. Nor does it show cellular abnormalities of the sort shown e.g. in WO 96/30766 at FIG. 29.

Nevertheless (e.g. at a time predetermined by addition of the stimulus) it is possible to seed the processing of the precursor protein to a product fragment (which may be the same, broadly equivalent, or quite different to the template fragment) which can thus accumulate to a (second, higher) concentration which is toxic to the cell and which corresponds to the disease state. This in turn provides convenient methods for modeling the disease state associated with the effects of the product fragment, and assessing the effect of modulators on the generation of the product fragment.

In various other, discrete, embodiments the invention provides corresponding methods for any of initiating, seeding, or controlling the proteolytic processing and optionally aggregation of the precursor protein to the product fragment.

In each case the method may involve monitoring (directly or indirectly) the level of proteolytic processing of the precursor protein.

In one embodiment of the present invention fibroblast cells (3T6) express full-length tau ("T40") under the control of an inducible promotor and low constitutive levels of the PHF-core tau fragment (12 kD fragment). When T40 expression is induced in this system, it undergoes aggregation-dependent truncation within the cell, N-terminally at ~a.a.295 and C-terminally at ~a.a.390, thereby producing higher levels of the 12 kD PHF-core domain fragment. Production of the 12 kD fragment can be blocked in a dose-dependent manner by tau-aggregation inhibitors. Indeed the quantitation of inhibitory activity of compounds with respect to proteolytic generation of the 12 kD fragment within cells can be described entirely in terms of the same parameters which describe inhibition of tau-tau binding in vitro. That is, extent of proteolytic generation of the 12 kD fragment within cells is determined entirely by the extent to tau-tau binding through the repeat domain. The availability of the relevant proteases within the cell is non-limiting.

Precursor Proteins and Diseases (Including Tauopathies)

As stated above, the invention may be based around the use of any protein which is associated with a disease in which the protein undergoes an induced conformational polymerisation interaction i.e. one in which a conformational change of the protein, or in a fragment thereof, gives rise to templated binding and aggregation of further (precursor) protein molecules in a self-propagating manner.

Once nucleation is initiated, an aggregation cascade may ensue which involves the induced conformational polymerisation of further protein molecules, leading to the formation of toxic product fragments in aggregates which are substantially resistant to further proteolysis. The protein aggregates thus formed are thought to be a proximal cause of neurodegeneration, clinical dementia, and other pathological symptoms of this group of diseases.

Preferred embodiments of the invention are based on tau protein. Where used herein, the term "tau protein" refers generally to any protein of the tau protein family. Tau proteins are characterised as being one among a larger number of protein families which co-purify with microtubules during repeated cycles of assembly and disassembly (Shelanski et al. (1973) Proc. Natl. Acad. Sci. USA, 70, 765-768), and are known as microtubule-associated-proteins (MAPs). Members of the tau family share the common features of having a characteristic N-terminal segment, sequences of approximately 50 amino acids inserted in the N-terminal segment, which are developmentally regulated in the brain, a characteristic tandem repeat region consisting of 3 or 4 tandem repeats of 31-32 amino acids, and a C-terminal tail.

MAP2 is the predominant microtubule-associated protein in the somatodendritic compartment (Matus, A., in "*Microtubules*" [Hyams and Lloyd, eds.] pp 155-166, John Wiley and Sons, NY). MAP2 isoforms are almost identical to tau protein in the tandem repeat region, but differ substantially both in the sequence and extent of the N-terminal domain (Kindler and Garner (1994) Mol. Brain Res. 26, 218-224). Nevertheless, aggregation in the tandem-repeat region is not selective for the tau repeat domain. Thus it will be appreciated that any discussion herein in relation to tau protein or tau-tau aggregation should be taken as relating also to tau-MAP2 aggregation, MAP2-MAP2 aggregation and so on.

FIG. 5 shows a Table listing various other disease-associated aggregating proteins which may be used in the present invention. In each case the disease or diseases in which the initiation of aggregation and\or mutation of the protein(s) may play a role is also listed. The domain or mutation responsible for the disease activity is listed, and at least all or part of this minimal portion of the protein would preferably be encompassed by the template fragment used in the present invention.

As can be seen from the table, example diseases which are characterised by pathological protein aggregation include motor neurone disease and Lewy body disease.

Notably it is not only Alzheimer's Disease in which tau protein (and aberrant function or processing thereof) may play a role. The pathogenesis of neurodegenerative disorders such as Pick's disease and Progressive Supranuclear Palsy (PSP) appears to correlate with an accumulation of pathological truncated tau aggregates in the dentate gyrus and stellate pyramidal cells of the neocortex, respectively. Other dementias include fronto-temporal dementia (FTD); parkinsonism linked to chromosome 17 (FTDP-17); disinhibition-dementia-parkinsonism-amyotrophy complex (DDPAC); pallido-ponto-nigral degeneration (PPND); Guam-ALS syndrome; pallido-nigro-luysian degeneration (PNLD); cortico-basal degeneration (CBD) and others (see Wischik et al. 2000, loc. cit, for detailed discussion—especially Table 5.1). All of these diseases, which are characterized primarily or partially by abnormal tau aggregation, are referred to herein as "tauopathies".

Thus it will be appreciated, in the light of the above discussion, (and except where context requires otherwise) where the embodiments of the invention are described with respect to tau protein or tau-like proteins (e.g. MAP2) the description should be taken as applying equally to the other proteins discussed above (e.g. β-amyloid, synuclein, prion etc.) or other proteins which may initiate or undergo a similar pathological aggregation by virtue of conformational change in a domain critical for propagation of the aggregation, or which imparts proteolytic stability to the aggregate this formed (article by Wischik et al. (in "Neurobiology of Alzheimer's Disease", 2nd Edition (2000) Eds. Dawbarn, D. and Allen, S. J., The Molecular and Cellular Neurobiology Series, Bios Scientific Publishers, Oxford). All such proteins may be referred to herein as "aggregating disease proteins."

Likewise, where mention is made herein of "tau-tau aggregation", or the like, this may also be taken to be applicable to other "aggregating-protein aggregation", such as β-amyloid aggregation, prion aggregation and synuclein aggregation etc. Likewise "tau proteolytic degradation" and so on.

Template Fragments

In preferred embodiments of the present invention, the template fragment, comprises, consists essentially of, or consists of a "core fragment" of the precursor protein, which term refers to that part of the protein that is able to bind to the precursor protein to initiate or propagate proteolysis and aggregation as described above.

In the case of disease proteins which aggregate, such core fragments are also likely to be those which contribute to the proteolytic stability of the aggregate.

Thus, for example, a "tau core fragment" is a tau fragment comprising a truncated tau protein sequence derived from the tandem repeat region and, which, in the appropriate conditions, is capable of binding to the tandem repeat region of a further tau protein or a MAP2 protein with high affinity. In the case of tau, the preferred fragment is thus exemplified by, but not limited to, the tau fragments present in PHFs (and, ultimately, neurofibrillary tangles) in Alzheimer's disease brains.

A preferred tau fragment may thus be from about (say) between 295-297 extending to about 390-391 (see 'dGAE' in FIG. 6) although variants of such fragments may also be used, as discussed below.

In the case of APP (amyloid precursor protein), for instance, expression of a fragment of the APP that encompasses the Aβ domain of 1-40 or 1-42 amino acids as a fusion protein, may be preferred.

Other core fragments may be based e.g. on the domains discussed with reference to FIG. 5. Template fragments may include domains from two, or more than two, of these proteins (e.g. as fusions).

The total length of the template fragment may be any which is appropriate to the assay and aggregation disease protein core fragment being used, but will generally be greater than or equal to about 20, 30, 40, 50, 60, 70, 80, 90, or so amino acids in length. However in some embodiments it may be greater than 100, 200 or even 500, if this is desired.

Derivatives

In all instances herein where a named protein (e.g. precursor protein, template or core fragment) or a recited nucleic acid sequence is discussed, a derivative or other variant of the corresponding reference protein (or nucleic acid) may be used as appropriate, provided that it retains appropriate characteristics of the reference sequence. Such derivatives will also share sequence identity with the reference sequence.

For instance the protein used may include an extended N- or C-terminus, which extension may be heterologous to the protein sequence. Equally, the derivative will be one by way of amino acid insertion, deletion, or addition of the reference sequence. For example, a tau protein, or tau core fragment, derivative will comprise at least a partial amino acid sequence resembling the tandem repeat region of the tau proteins, but in which one or more of the amino acids of the natural tau or its fragments have been replaced or deleted, or into which other amino acids have been inserted.

Such changes may be made to enhance or ablate binding activity (the latter case being useful for control experiments). Controls may contain deletions of sequences or domains to see what effect on aggregation these may have.

Preferred derivatives may be those which incorporate mutations corresponding to those known or suspected to be associated with the disease state. These may include changes corresponding to P301S within the tau sequence (see FIG. 7). Other mutations include G272V, G389R, P301L, N279K, S305N, V337M, G272V, K280Δ, R406W (see also Wischik et al, 2000, supra).

Other preferred derivatives may include tandem repeats of the core-fragments discussed above, or binding domains within those fragments.

Yet further derivatives may be based on chimeric products based on multiple, related, disease proteins in which their sequences are mixed or combined. For example restriction enzyme fragments of tau could be ligated together with fragments of MAP2 or even of an unrelated gene to generate recombinant derivatives. An alternative strategy for modifying the core fragments would employ PCR as described by Ho et al., 1989, Gene 77, 51-59 or DNA shuffling (Crameri et al., 1998 Nature 391).

Use of Nucleic Acid Constructs

Nucleic acids of, or for use in, the present invention may be provided isolated and/or purified from their natural environment, in substantially pure or homogeneous form, or free or substantially free of other nucleic acids of the species of origin. Where used herein, the term "isolated" encompasses all of these possibilities. Nucleic acids e.g. encoding the template fragment, will be at least partially synthetic in that it will comprise nucleic acid sequences which are not found together in nature (do not run contiguously) but which have been ligated or otherwise combined artificially.

Nucleic acid according to the present invention may be in the form of, or derived from, cDNA, RNA, genomic DNA and modified nucleic acids or nucleic acid analogs. Where a DNA sequence is specified, e.g. with reference to a figure, unless context requires otherwise the RNA equivalent, with U substituted for T where it occurs, is encompassed.

As described above, the nucleic acids may encode derivatives or other variants sharing homology with the reference sequences in question. Preferably, the nucleic acid and/or amino acid sequence in question would share about 50%, or 60%, or 70%, or 80% identity, most preferably at least about 90%, 95%, 96%, 97%, 98% or 99% of the sequence upon which the variant is based. Similarity or homology may be as defined and determined by the TBLASTN program, of Altschul et al. (1990) J. Mol. Biol. 215: 403-10, which is in standard use in the art, or, and this may be preferred, the standard program BestFit, which is part of the Wisconsin Package, Version 8, September 1994, (Genetics Computer Group, 575 Science Drive, Madison, Wis., USA, Wisconsin 53711) using the default parameters. One common formula for calculating the stringency conditions required to achieve hybridization between nucleic acid molecules of a specified sequence homology is: $T_m=81.5°\text{C}.+16.6 \text{ Log }[\text{Na}+]+0.41$ (% G+C)−0.63 (% formamide)−600/#bp in duplex.

Nucleic acid sequences which encode the appropriate proteins or polypeptides can be readily prepared by the skilled person using the information and references contained herein and techniques known in the art (for example, see Sambrook, Fritsch and Maniatis, "Molecular Cloning, A Laboratory Manual", Cold Spring Harbor Laboratory Press, 1989, and Ausubel et al., Short Protocols in Molecular Biology, John Wiley and Sons, 1992). These techniques include (i) the use of the polymerase chain reaction (PCR) to amplify samples of the relevant nucleic acid, e.g. from genomic sources, (ii) chemical synthesis, or (iii) preparation of cDNA sequences.

DNA encoding e.g. tau core fragments may be generated and used in any suitable way known to those of skilled in the art, including by taking encoding DNA, identifying suitable restriction enzyme recognition sites either side of the portion to be expressed, and cutting out said portion from the DNA. Modifications to the protein (e.g. tau)-encoding sequences can be made, e.g. using site directed mutagenesis.

Constructs

Thus the invention also relates, in a further aspect, to nucleic acid molecules encoding the appropriate precursor and template fragment proteins. As discussed below, these may be present on the same or different constructs, and in the latter case, compositions comprising two or more types of construct are also provided.

Nucleic acid sequences which enable a vector to replicate in one or more selected host cells are well known for a variety of bacteria, yeast, and viruses. For Example, various viral origins (SV40, polyoma, adenovirus, VSV or BPV) are useful for cloning vectors in mammalian cells. Expression vectors comprising a nucleic acid as described herein may, for example, be in the form of a plasmid, cosmid, viral particle, phage, or any other suitable vector or construct which can be taken up by a cell and expressed appropriately.

Expression vectors will contain a promoter which is operably linked to the protein-encoding nucleic acid sequence of interest, so as to direct mRNA synthesis. Promoters recognized by a variety of potential host cells are well known. "Operably linked" means joined as part of the same nucleic acid molecule, suitably positioned and oriented for transcription to be initiated from the promoter. DNA operably linked to a promoter is "under transcriptional control" of the promoter. Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g. the actin promoter or an immunoglobulin promoter, and from heat-shock promoters, provided such promoters are compatible with the host cell systems. Expression vectors used in eukaryotic host cells (yeast, fungi, insect, plant, animal, human, or nucleated cells from other multicellular organisms) will also contain sequences necessary for the termination of transcription and for stabilizing the mRNA.

The promoter used for the template fragment will be "constitutive". This promoter may be sufficiently weak that the level of template fragment expressed in the cell is not itself (directly) detectable using conventional techniques, other than (indirectly) by its affect on precursor protein, leading to aggregation and proteolytic processing thereof (i.e. effectively undetectable when said aggregation is inhibited). Such promoters may be selected by those skilled in the art in the light of the present disclosure without undue burden such as those listed above.

In the case of the precursor protein, the promoter is "inducible"—which is to say, and as is well understood by those skilled in the art, expression is "switched on" or increased in response to an applied stimulus. The nature of the stimulus varies between promoters. Some inducible promoters cause little or undetectable levels of expression (or no expression) in the absence of the appropriate stimulus. Other inducible promoters cause detectable constitutive expression in the absence of the stimulus. Whatever the level of expression is in the absence of the stimulus, expression from any inducible promoter is increased in the presence of the correct stimulus. In experiments below, a Lac inducible promoter has been used.

Expression vectors of the invention may also contain one or more selection genes. Typical selection genes encode proteins that (a) confer resistance to antibiotics or other toxins e.g. ampicillin, neomycin, methotrexate, or tetracycline, (b) complement auxotrophic deficiencies, or (c) supply critical nutrients not available from complex media, e.g., the gene encoding D-alanine racemase for Bacilli. An example of suitable selectable markers for mammalian cells are those that enable the identification of cells competent to take up the desired protein-encoding nucleic acid, such as DHFR or thymidine kinase. An appropriate host cell, when wild-type DHFR is employed, is the CHO cell line deficient in DHFR activity, prepared and propagated as described by Urlaub et al., *Proc. Natl. Acad Sci USA* 77:4216 (1980). A suitable selection gene for use in yeast is the trp1 gene present in the yeast plasmid Rp7 [Stinchcomb et al., Nature, 282:39 (1979); Kingsman et al., Gene, 7:141 (1979); Tschemper et al., Gene, 10:157 (1980)]. The trp1 gene provides a selection marker for a mutant strain of yeast which lacks the ability to grow in tryptophan, for example, ATCC: No. 44076 or PEP4-1 [Jones, Genetics, 85:12 (1977)].

Thus a typical vector for use in the present invention may include an origin of replication, one or more protein sequence(s) operably linked to a constitutive or inducible promoter as appropriate, a transcription termination sequence, an enhancer element, a marker gene. Construction of suitable vectors containing various of these components employs standard ligation techniques which are known to the skilled artisan.

Transformation

Also provided by the present invention is a process for producing a stable cell for use in a method as described above, which process comprises the steps of: (a) introducing into a cell nucleic acid encoding (i) a template fragment of the precursor protein such that the template fragment is constitutively expressed in the cell at a level which is not toxic to the cell; and (ii) the precursor protein such that the disease protein is inducibly expressed in the cell in response to a stimulus.

The introduction, which may be generally referred to without limitation as "transformation", may employ any available technique. For eukaryotic cells, suitable techniques may include calcium phosphate transfection, DEAE-Dextran, electroporation, liposome-mediated transfection and transduction using retrovirus or other virus, e.g. vaccinia or, for insect cells, baculovirus. The calcium treatment employing calcium chloride, as described in Sambrook et al., supra, or electroporation is generally used for prokaryotes or other cells that contain substantial cell-wall barriers. Infection with *Agrobacterium tumefaciens* is used for transformation of certain plant cells, as described by Shaw et al., Gene, 23:315 (1983) and WO 89/05859 published 29 Jun. 1989.

For mammalian cells without such cell walls, the calcium phosphate precipitation method of Graham and van der Eb, Virology 52:456-457 (1978) can be employed. General aspects of mammalian cell host system transformations have been described in U.S. Pat. No. 4,399,216. Transformations into yeast are typically carried out according to the method of Van Solingen et al., J. Bact., 130:946 (1977) and Hsiao et al., Proc. Natl. Acad. Sci. (USA), 76:3829 (1979). However, other methods for introducing DNA into cells, such as by nuclear microinjection, electroporation, bacterial protoplast fusion with intact cells, or polycations, e.g, polybrene, polyornithine, may also be used. For various techniques for transforming mammalian cells, see Keown et al., Methods in Enzymology, 185:527 537 (1990) and Mansour et al., Nature 336:348-352 (1988).

Host Cells

Suitable host cells for use in the invention may include bacteria, eukaryotic cells such as mammalian and yeast cells, and baculovirus systems.

Mammalian cell lines available in the art for expression of a heterologous polypeptide include fibroblast 3T6 cells, HeLa cells, baby hamster kidney cells, COS cells, monkey kidney CV1 line transformed by SV40 (COS-7, ATCC CRL 1651), Chinese hamster ovary cells/–DHFR (CHO, Urlaub and Chasin, Proc. Natl. Acad. Sci. USA 77:4216 (1980)); mouse sertoli cells (TM4, Mather, Biol. Reprod. 23:243-251 (1980)); human lung cells (W138, ATCC CCL 75); human liver cells (Hep G2, HB 8065); mouse mammary tumour cells (MMT 060562, ATCC CCL51); and many others.

Suitable prokaryotic hosts include but are not limited to eubacteria, such as Gram-negative or Gram-positive organisms, for example, Enterobacteriaceae such as E. coli. Various E. coli strains are publicly available, such as E. coli K12 strain MM294 (ATCC 31,446); E. coli X1776 (ATCC 31,537); E. coli strain W3110 (ATCC 27,325) and K5 772 (ATCC 53,635). Eukaryotic microbes such as filamentous fungi or yeast are also suitable cloning or expression hosts for vectors. Saccharomyces cerevisiae is a commonly used lower eukaryotic host microorganism. The selection of the appropriate host cell is deemed to be within the skill in the art.

In a further aspect, the present invention provides a host cell containing heterologous nucleic acid of the invention as described above. The nucleic acid of the invention may be integrated into the genome (e.g. chromosome) of the host cell. Integration may be promoted by inclusion of sequences which promote recombination with the genome, in accordance with standard techniques. Alternatively, the nucleic acid may be on an extrachromosomal vector within the cell, or otherwise identifiably heterologous or foreign to the cell.

The cell may be produced by a method described above (introduction of nucleic acid construct) or be the ancestor of such a cell. Corresponding cell-lines are also provided. Preferred cell-lines may be based on the fibroblast cell line, e.g. 3T6.

Host cells transfected or transformed with expression or cloning vectors described herein may be cultured in conventional nutrient media modified as appropriate for inducing promoters, selecting transformants, or amplifying the genes encoding the desired sequences. The culture conditions, such as media, temperature, pH and the like, can be selected by the skilled artisan without undue experimentation. In general, principles, protocols, and practical techniques for maximizing the productivity of cell cultures can be found in "Mammalian Cell Biotechnology: a Practical Approach", M. Butler, ed. JRL Press, (1991) and Sambrook et al, supra.

Gene expression can be confirmed in a sample directly, for example, by conventional Southern blotting, Northern blotting to quantitate the transcription of mRNA [Thomas, Proc. Natl. Acad. Sci. USA, 77:5201-5205 (1980)], dot blotting (DNA analysis), or in situ hybridization, using an appropriately labeled probe, based on the sequence of the aggregating disease protein. Alternatively, antibodies may be employed that can recognize specific duplexes, including DNA duplexes, RNA duplexes, and DNA-RNA hybrid duplexes or DNA-protein duplexes.

Gene expression, alternatively, may be measured by immunological methods such as immunohistochemical staining of cells or tissue sections, and assay of cell culture, to quantitate directly the expression of gene product. Antibodies useful for immunohistochemical staining and/or assay of sample fluids may be either monoclonal or polyclonal, and may be prepared in any mammal. Conveniently, the antibodies may be prepared against a native sequence of the aggregating disease polypeptide.

Thus one aspect of the present invention entails causing or allowing expression from the nucleic acids discussed herein, e.g. by culturing host cells under conditions for expression of the gene (presence of stimulus) so that the product fragment is produced. The present invention also encompasses a method of producing the product fragment, the method including expression from nucleic acid as described above.

Another aspect of the present invention is a kit comprising a transformed cell or cell line as described herein, plus at least one further component e.g. an agent for stimulating production of the precursor protein, or an agent for detecting the interaction of the precursor protein with the template fragment, as described in the following section.

Detection of Aggregation and\or Proteolytic Processing and\or Toxic Fragment

In various embodiments, the progress of proteolytic processing or aggregation (or modulation thereof—see below) may be detected directly or indirectly by monitoring the concentration or level any one or more of the following species: the precursor protein; the product fragment; any by-product fragments formed during the process; an aggregate of any of these (e.g. based on sedimentation coefficients).

Thus, as exemplified with particular tau proteins and fragments (based on 297-351 fragment and T40), aggregation can be monitored on the basis of increasing levels of a 12 kDa processed species, derived primarily from the precursor protein.

Some protein detection methods are discussed in relation to gene expression above. Where antibodies or fragments thereof are used in embodiments of the method of the present invention may be produced by conventional techniques. Polyclonal antibodies may raised e.g. by injecting the corresponding tau antigen into an animal, preferably a rabbit, and recovering the antiserum by immunoaffinity purification, in which the polyclonal antibody is passed over a column to which the antigen is bound and is then eluted in a conventional manner. Preferably the invention will use monoclonal antibodies which are selective to tau epitopes may be prepared by the method of Kohler and Milstein. Suitable monoclonal antibodies to tau epitopes can be modified by known methods to provide Fab fragments or (Fab')2 fragments, chimeric, humanised or single chain antibody embodiments.

Antibodies according to the present invention may be modified in a number of ways. Indeed the term "antibody" should be construed as covering any binding substance having a binding domain with the required specificity. Thus the invention covers antibody fragments, derivatives, functional equivalents and homologues of antibodies, including synthetic molecules and molecules whose shape mimics that of an antibody enabling it to bind an antigen or epitope.

Generally speaking, where antibodies are employed for detection, the antibody may carry a reporter molecule. Alternatively, detection of binding may be performed by use of a second antibody capable of binding to a first unlabelled, tau-specific antibody. In this case, the second antibody is linked to a reporter molecule.

Antibodies may be used in any immunoassay system known in the art, including, but not limited to: radioimmunoassays, "sandwich" assays, enzyme-linked immunosorbent assays (ELISA); fluorescent immuno-assays, protein A immunoassays, etc. Typically, an immunoblot method is used. Preferably the immunoassay is performed in the solid phase, as would be well known to the skilled person. For instance, an antibody may be adsorbed to e.g. an assay column, and the cellular sample may then be washed through the column under conditions suitable for enabling binding to the solid-phase antibody of any aggregate of the protein of interest, e.g. a tau-tau aggregate. Excess reagent is washed away, and the binding of aggregated protein to the column can then be detected by any suitable means, e.g. as exemplified above and below.

Preferred monoclonal antibodies are as follows:

Those which recognise the N-terminal or C-terminal of the tau epitope permit measuring of binding between truncated and full-length tau species. Especially useful are antibodies recognising human-specific epitopes. One such monoclonal antibody (designated 27/499) recognises a human-specific epitope located in the region between Gly-16 and Gln-26 of tau, and thereby permits measurement of binding between full-length tau species, provided one is derived from a non-human source (Lai (1995); "The role of abnormal phosphorylation of tau protein in the development of neurofibrillary pathology in Alzheimer's disease", PhD Thesis, University of Cambridge).

Those which recognise the core tau fragment truncated at Glu-391. An example is mAb 423 (Novak et al. (1993), loc. cit.). This antibody enables detection of the binding of a truncated core tau fragment terminating at Glu-391 to a similar fragment terminating at Ala-390, which is not recognised by mAb 423. This truncation occurs naturally in the course of PHF assembly in Alzheimer's disease (Mena et al. (1995), (1996), loc. cit.; Novak et al. (1993), loc. cit.; Mena et al. (1991), loc. cit.). Additionally, when tau is bound via the repeat domain in vitro, digestion with a protease (e.g. pronase) generates a fragment detectable by mAb 423 (see Wischik et al, 1996, loc cit). In the preferred aspects of the present invention, as it relates to tau protein, this antibody may be used to distinguish the generation of proteolytically cleaved product fragment (Glu-391 termination) from constitutive expression of template fragment (Ala-390).

Those which recognise a generic tau epitope in the repeat domain. A preferred embodiment utilises an antibody (e.g. MAb 7.51). Where tau-MAP2 or MAP2-MAP2 aggregation is to be detected, an antibody which detects a generic MAP2 epitope could be used. Antibody 7.51 recognises a generic tau epitope located in the antepenultimate repeat of tau (Novak et al. (1991) Proc. Natl. Acad. Sci. USA, 88, 5837-5841), which is occluded when tau is bound in a PHF-like immunochemical configuration but can be exposed after formic acid treatment (Harrington et al. (1990), (1991), loc. cit.; Wischik et al. (1995a), loc. cit.). Normal soluble tau, or tau bound to microtubules, can be detected using mAb 7.51 without formic acid treatment (Harrington et al. (1991), loc. cit.; Wischik et al. (1995a), loc. cit.). Binding of full-length tau in the tau-tau binding assay is associated with partial occlusion of the mAb 7.51 epitope.

Antibody 27/342 recognises a non-species specific generic tau epitope located between Ser-208 and Ser-238 which is partially occluded in the course of the tau-tau interaction (Lai, loc. cit.).

The binding sites of some monoclonal antibodies are shown in FIG. 6.

Screening for Modulators and Inhibitors

As described above, the invention is preferably concerned with use of a system as provided herein, in a method of modeling, and identifying therapeutic agents for treatment of, the diseases discussed herein.

A typical method for assessing the ability of an agent to modulate the aggregation and\or proteolytic processing of a precursor protein to a product in response to interaction with a template fragment, may comprise:

(a) providing a stable cell or cell line as discussed above,
(b) subjecting the cell to the stimulus such that the precursor protein is expressed in the cell and whereby interaction of the template fragment with the precursor protein causes a conformational change in the protein such as to cause aggregation and proteolytic processing of the precursor protein to a product fragment,
(c) monitoring the production of the product fragment in the presence of the agent,
(d) optionally comparing the value obtained in step (c) with a reference value.

The reference value may be based on historical observation, or may be based on control experiments carried out in parallel e.g. in which one integer of the assay (template fragment, precursor protein, stimulus, agent) is modified or absent.

The various methods described above may comprise the further step of correlating the result of step (d) with the modulatory activity of the agent(s).

Thus a method of identifying a modulator of aggregation of a protein associated with a disease in which the protein undergoes an induced conformational interaction, may comprise performing a method for inducing aggregation as described above in the presence of one or more agents suspected of being capable of modulating (e.g. inhibiting or reversing) the aggregation. The degree of aggregation (and optionally proteolytic processing) may be observed in the presence or absence of the agent, and the relative values correlated with its activity as a modulator.

For example, a test substance may be added to a cellular system as described above, and the cells incubated for a period of time sufficient to allow binding and to demonstrate inhibition of binding. The bound tau complex can then be detected, e.g. using a suitably-labeled antibody such as MAb 7.51 in an immunoblot of total cell extract, or any other suitable detection method.

Where a screening method is employed for this purpose, i.e. for the identification of modulatory/inhibitory compounds, a non-competitive or competitive assay may be used. For instance, in a competitive assay of the type well known in the art, the effect of a known inhibitor or modulator can be compared in the presence or absence of further test substances or agents, to determine the ability of the test substance to compete with the known inhibitor/modulator for binding to the protein of interest.

Also provided are methods of producing modulators (e.g. inhibitors) which are as described above, but which further comprise the step of producing the modulator this identified.

Specificity of Inhibition

Screening methods according to this aspect of the present invention may be used to screen for compounds which demonstrate the properties of selective competitive inhibition of disease-related protein aggregation (e.g. tau-tau, tau-MAP2, or other protein, binding), without interference with any 'normal' binding in which the precursor protein participates (e.g. tau or MAP2 to tubulin, or by analogy, other precursor proteins with their binding partners insofar as these are known).

Specifically in the case of tau, a method for determining any possible interference of the binding of tau, MAP2 or a derivative thereof to tubulin by potential inhibitors/modulators, comprises contacting a preparation of depolymerised tubulin or taxol-stabilised microtubules with the agent, followed by detection of the tau-tubulin or MAP2-tubulin binding. Tau-tubulin binding could also, for example, be demonstrated by a normal cytoskeletal distribution, as described in e.g. WO 96/30766. Methods for the preparation of tubulin proteins or fragments thereof, possibly in combination with binding partners, are known in the art and are described e.g. by Slobada et al. (1976, in: Cell Mobility (R. Goldman, T. Pollard and J. Rosenbaum, eds.), Cold Spring Laboratory, Cold Spring Harbor, N.Y., pp 1171-1212).

Analogous methods for other proteins having 'disease' and 'normal' functions will occur to those skilled in the art in the light of the present disclosure.

Cell Viability

Where desired, methods of the present invention may further include the step of testing the viability of the cells expressing the template protein and optionally precursor protein e.g. by use of a lactate dehydrogenase assay kit (Sigma).

In the case where tau-tau, tau-MAP2 or MAP2-MAP2 aggregation is being investigated (see above, under 'specificity'), this step may also provide an indication of any interference by the test agent of the binding of tau or MAP2 to tubulin, since inhibition or interference of tau-tubulin or MAP2-tubulin binding will correlate to some extent with a decreased ability of the cells to divide, and thus with decreased cell viability.

Cell viability may be used to derive an LD50 value for the agent.

Preferred inhibitors will have a therapeutic index (LD50/B50—see discussion of FIG. 9) of at least 2, 5, 10, or 20.

Choice of Test Agent

Compounds which are tested may be any which it is desired to assess for the relevant activity.

The methods can serve either as primary screens, in order to identify new inhibitors/modulators, or as secondary screens in order to study known inhibitors/modulators in further detail.

Agents may be natural or synthetic chemical compounds. Antibodies which recognise an Alzheimer's disease-like protein aggregate and/or which modulate Alzheimer's disease-like protein aggregation form one class of putative inhibitory or modulatory compounds with respect to the aggregation process. More usually, relatively small chemical compounds, preferably which are capable of crossing the blood-brain barrier, will be tested. Other qualities which it may be desirable to establish in conjunction with (before, simulataneously with, or after) use of the present invention, include: non-toxic to bone marrow, minimal deleterious cardiovascular activity; minimal liver and renal toxicity; good oral absorption; non-metabolised to inactive form, and so on. As those skilled in the art are aware, these tests can be performed on a commercial basis by well established methods for compounds which it is desired to test in this way.

For a typical test substance and putative modulator, where possible, the solubility will first be determined e.g. from The Merck Index. Where the substance is soluble in aqueous solution, a concentrated stock solution may be prepared e.g. at 5-20 mM in PBS. Immediately prior to use this can be diluted with tissue culture medium to give a working stock solution e.g. at 100 µM and introduced to cells to give a final concentration of between 0-10 µM for most compounds. Naturally, if it is desired to test compounds at a concentration greater than 10 µM, the concentration of the working stock solution may be increased appropriately.

Where the substance is not soluble in aqueous solution, stock solutions may be made in an appropriate solvent (determined from The Merck Index or experimentally) e.g. ethanol at 5-29 nM. This can again be diluted with tissue culture medium immediately prior to use to give a working solution e.g. at 100 µM concentration, and added to cells to yield a final concentration of e.g. 0-10 µM for most test compounds. As above, if compounds are to be tested at a concentration greater than 10 µM the concentration of the working solution will be increased as appropriate.

The skilled person will appreciate that the amount of test substance or compound which is added in a screening assay according to this aspect of the invention, and indeed the manner in which it is introduced, can be determined by those skilled in the art, if necessary by use of a series of trials. Where the administered compound and the cell line have conflicting optimal conditions (e.g. in terms of pH, or ionic strength etc.) a variety of conditions should be tried to find an optimal, compromise, level. Initial concentrations may be selected to be a level which could realistically be used in therapeutic context i.e. would be non-lethal to a patient (see comments on dosages below). In the light of the present disclosure, such an approach will not present any undue burden to one skilled in the art.

Screening Phenothiazines

The present invention extends, in further aspects, to compounds identified by a screening method as provided herein, and to compositions comprising such inhibitors/modulators of induced conformational polymerisation of a protein.

As described in e.g. WO 96/30766, amongst the agents found to be able to inhibit pathological induced conformational polymerisation of proteins such as tau are certain diaminophenothiazines. Examples include such as thionine, methylene blue (MB), tolonium chloride, and dimethyl-methylene blue (DMMB) which are of particular interest as potential therapeutic agents for use in the prevention of tau-tau aggregation in diseases such as Alzheimer's Disease.

Interestingly, as described in more detail in the Examples, the present inventors have used the methods described herein to demonstrate that the mechanism of action of compounds such as MB on induced conformational polymerisation such as tau-tau aggregation is primarily steric in nature. Additionally, it has been shown that the potent steric inhibitory effect, e.g. of the diaminophenothiazines on tau-tau binding, is dependent on the diffusion coefficient of the compound. The various implications of these observations in terms of screening and formulating compounds are discussed in more detail below.

This finding is particularly unexpected when considering the description of the use of the such compounds in the prior art. Thus, for example, such compounds were previously known to be useful in the treatment of methaemoglobinaemia, where their action has been shown to be mediated by the catalytic reduction of oxidised haemoglobin by transfer of electrons from the cell's intrinsic supply of reduced pyridine nucleotides (see, e.g. Hauschild, F. (1936) *Arch. Exp. Pathol. Pharmacol.* 182:118; *"Pharmacological Basis of Therapeutics"*, First Edition (1941), Goodman and Gilman; Hrgovic, Z.

(1990) Anästh. Intensivther. Notfallmed. 25: 172; and Cudd, L. et al. (1996) Vet Human Toxicol. 38(5): 329) and in the prophylaxis of manic depressive psychosis (Narsapur, S. L. (1983) Journal of Affective Disorders 5:155; Naylor, G. J. (1986) Biol. Psychiatry 21:915). Notwithstanding this, MB, thionine and tolonium chloride are actually intrinsically weak oxidising agents and, in the absence of a supply of reduced pyridine nucleotides, they oxidise proteins such as haemoglobin (Morse, E. (1988) Annals of Clin. Lab. Sci. 18(1):13). This toxic effect can be used to inactivate viruses, and MB has consequently been exploited therapeutically in a process for removing HIV and hepatitis virus from blood products (Chapman, J. (1994), Transfusion Today 20:2; Wagner, S. J. (1995) Transfusion 35(5):407). The mechanism of action of this effect is thought to involve intercalation of MB into DNA. The compound is boosted to a higher redox state by photoactivation and, when it drops back down to its ground state, produces singlet oxygen which oxidises the DNA and inactivates it (Ben-Hur, E. et al. (1996) Transfusion Medicine Reviews, Vol. X, No. 1: 15; Margolis-Nunno, H. et al. (1994), Transfusion 34(9): 802). Exploitation of the toxic effect of photoactivated diaminophenothiazines has also been suggested for the treatment of cancer. Within cells, compounds which have been photoactivated to the oxidised form can damage mitochondria (Darzynkiewicz, Z. et al. (1988), Cancer Research 48: 1295) and/or microtubules (Stockert, J. et al. (1996) Cancer Chemother. Pharmacol. 39: 167).

Thus, on reviewing the prior art, it is apparent that two possible mechanisms have been proposed to account for the action of compounds such as MB and thionine on entities such as DNA or proteins. The first is the catalytic reduction of e.g. oxidised proteins by means of transfer of electrons from reduced pyridine nucleotides in the cell. The second proposed mechanism is the oxidation, and consequent inactivation of e.g. DNA by a photoactivated, oxidised form of compounds such as MB. In the light of these two mechanisms, it could therefore reasonably have been assumed that the inhibitory effect on tau-tau association of compounds such as MB was also attributable to a redox activity.

That is, it might be assumed that such compounds inhibit induced conformational polymerisation such as tau-tau association by acting as weak oxidising agents or as catalytic reducing agents.

Thus the work of the present inventors, in demonstrating that the mechanism of action is primarily steric in nature, has unexpected implications for the choice, assessment, formulation and use of such compounds in the context of the diseases discussed herein.

In particular, certain compounds have been identified as feasible therapeutics which would have been dismissed based on the result of prior art assays. Specifically, Wischik et al. 1996 (loc cit) reported on page 1217 that the concentration of MB required for inhibition was higher than could be achieved clinically. However the results herein show that the reduction of MB modifies its stacking ability in such a way as to enhance its inhibitory potential to a level at which it becomes clinically relevant for the treatment of e.g. tau aggregation associated disease. This is discussed in more detail below in relation to the embodiments of the invention concerned with measurement of diffusion coefficients (which are also determined, in part, by the compound's ability to 'stack').

FIG. 8 shows the structure of only some of the compounds which have been tested in the cell based assay. FIGS. 9-16 demonstrate the increased potency of certain compounds in the reduced form, plus some control compounds.

Thus in one aspect of the present invention there is disclosed use, in the treatment of a disease disclosed herein, of a reduced ('leuco') phenothiazine of the formula:

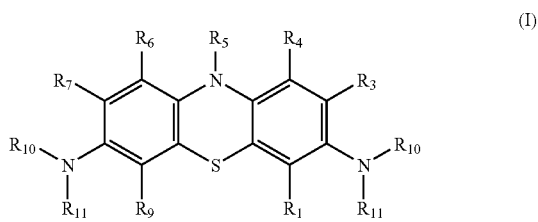

wherein $R_1$, $R_3$, $R_4$, $R_6$, $R_7$ and $R_9$ are independently selected from hydrogen, halogen, hydroxy, carboxy, substituted or unsubstituted alkyl, haloalkyl or alkoxy;

$R_5$ is selected from hydrogen, hydroxy, carboxy, substituted or unsubstituted alkyl, haloalkyl or alkoxy; and each $R_{10}$ and $R_{11}$ are independently selected from hydrogen, hydroxy, carboxy, substituted or unsubstituted alkyl, haloalkyl or alkoxy;

or a pharmaceutically acceptable salt thereof.

Preferably, $R_1$, $R_3$, $R_4$, $R_6$, $R_7$ and $R_9$ are independently selected from -hydrogen, —$CH_3$, —$C_2H_5$ or —$C_3H_7$;

each $R_{10}$ and $R_{11}$ are independently selected from hydrogen, —$CH_3$, —$C_2H_5$ or —$C_3H_7$; and $R_5$ is hydrogen, —$CH_3$, —$C_2H_5$ or —$C_3H_7$.

Preferably, the compound is a diaminophenothiazine which has 0, 2, 3 or 4 methyl groups around the diaminophenothiazine nucleus. Preferably, the diaminophenothiazine is asymmetrically methylated (e.g., tolonium chloride, azure A, azure B and thionine).

Preferably the compound is selected from Methylene Blue, Tolonium chloride, Thionine, Azure A, Azure B or 1,9-Dimethylmethylene Blue.

Phenothiazines for use in the present invention may be manufactured by the processes referred to in standard texts (e.g. Merck Manual, Houben-Weyl, Beilstein, E. III/IV 27, 1214 ff, J. Heterocycl. Chem. 21, 613 (1984)).

Instead of administering these compounds directly, they could be administered in a precursor form, for conversion to the active form by an activating agent produced in, or targeted to, the cells to be treated. For instance, methylene blue may be administered in a precursor form, or it may itself serve as a precursor of the compound Azure A.

Stabilisation of Reduced Form

Some of these compounds of interest are known to circulate in the body predominantly in the reduced form. For example, for a discussion of the pharmacokinetics of MB, see e.g. DiSanto, A. et al. (1972) Journal Pharm. Sci. 61(7):1086 and DiSanto, A. et al. (1972) Journal Pharm. Sci 61(7):1090. Thirdly, only the reduced form of compounds such as MB is found to cross the blood-brain barrier (Chapman, D. M. (1982) Tissue and Cell 14(3):475; Müller, T. (1992) Acta Anat. 144:39; Müller, T. (1994) J. Anat. 184:419; Becker, H. et al. (1952) Zeitschrift für Naturforschung 7:493; Müller, T. (1995) It. J. Anat. Embryol. 100(3):179; Müller, T. (1998) Histol. Histopathol. 13:1019).

Such references as these illustrate that the reduced form of compounds such as MB represents a feasible and pharmaceutically-acceptable formulation for administration to subjects. MB has previously been used clinically in an oral preparation. Further toxicological tests are, however, required before its clinical acceptability is achieved. The half live of MB and related compounds (e.g. tolonium chloride) in blood is approximately 100 minutes. It is evident that slow release formulations of compounds with such, relatively short, half lives can substantially improve compound availability and hence therapeutic efficacy.

FIG. 17 shows that compounds such as those discussed herein differ greatly in their extent of reduction in the conditions of the assay (approx. 500:1 DTT excess, at 120 minutes). As this figure shows, thionine is completely reduced under these conditions, tolonium chloride is reduced at an intermediate level, and MB and DMMB are relatively little reduced. The amounts of commonly used reductant required to achieve, say, 90% reduction of the oxidized form in 10 minutes, prior to administration\absorption may not be feasible (e.g. 2000:1 ratio of DTT to MB).

As FIG. 18 illustrates, the extent of reduction of MB under physiological conditions can be greatly accelerated by allowing reduction over night and then lyophilising the reduced form. The lyophilisate becomes reduced by 90% in 10 minutes, after solubilisation in conditions mimicking gastric acidity (5 mM HCl). Capsules containing a form of the diaminophenothiazine pre-reduced with ascorbic acid at a mg ratio of 1.5-2 represent a suitable, if not optimal, formulation for therapeutic use.

The same considerations apply to other compounds, such as thionine and tolonium chloride, which are more readily reduced than MB, but the extent of reduction of which can be accelerated in a manner such as that described above.

Thus in preferred forms the phenothiazine agents of the present invention are provided as pre-reduced compounds e.g. in lyophilised preparations, optionally in the presence of a stabilising agent.

An agent for stabilising the preferred form of the active compound (i.e. a form of the compound having a low diffusion coefficient, e.g. the fully-reduced form of the compound) may be a reducing agent or antioxidant. The agent may serve both to convert one form of the inhibitory compound (e.g. the oxidised form) to the preferred form thereof (e.g. the reduced form), and to stabilise that preferred (e.g. reduced) form. Alternatively, the inhibitory compound may be added to the composition in its preferred (e.g. already-reduced) form, so that the agent merely serves to maintain the compound in this form.

Particularly suitable for use in converting to, and/or stabilising, the reduced form of the active agent (e.g. the diaminophenothiazine) comprised in the formulations of the present invention is the antioxidant ascorbate. Ascorbate has previously been used to minimise oxidative damage of proteins (Parkkinen J. (1996), "Thrombosis and Haemostasis" 75(2): 292). A formulation as provided herein could thus advantageously comprise a diaminophenothiazine, especially MB, tolonium chloride, DMMB or thionine, in combination with ascorbate, in suitable proportions, concentrations and dosages.

In other embodiments the reduced (leuko) form may be favoured by the addition or selection of appropriate constituent groups.

Thus aspects of the invention further include a method of preparing a medicament for use in the treatment or prophylaxis of a disease as described above, which method comprises the step of reducing the compound (such that it is, say, at least 50, 60, 70, preferably 80, 90, 95, or 99% reduced) and stabilizing it in a lyophilized composition in the reduced form, prior to administration of an appropriate dose to a patient in need of the same.

Dosage of Therapeutics

Administration is preferably in a "prophylactically effective amount" or a "therapeutically effective amount" (as the case may be, although prophylaxis may be considered therapy), this being sufficient to show benefit to the individual. The actual amount administered, and rate and time-course of administration, will depend on the nature and severity of the disease being treated. Prescription of treatment, e.g. decisions on dosage etc., is within the responsibility of general practitioners and other medical doctors, and typically takes account of the disorder to be treated, the condition of the individual patient, the site of delivery, the method of administration and other factors known to practitioners.

CNS penetration of MB following systemic administration has been described by Müller (1992; *Acta Anat.* 144:39). Azure A and B are known to occur as normal metabolic degradation products of MB (Disanto and Wagner (1972a) *J. Pharm. Sci.* 61: 598; Disanto and Wagner (1972b) *J. Pharm. Sci.* 61: 1086). The pharmacokinetics and toxicity of tolonium chloride in sheep is discussed by Cudd et al (1996) Vet Human Toxic 38 (5) 329-332.

For thionine, which is specifically exemplified herein, a daily dosage of between 1 and 1000 mg may be suitable, preferably divided into 1 to 8 unit doses, which can, for example, be of the same amount. It will, however, be appreciated that these limits given above can be departed from when required, as may be appropriate with the compounds of the invention other than thionine, which have higher or lower activity or bioavailability.

FIG. 19 shows the variation of tissue levels of MB vs IV dose.

The pharmacokinetics of methylene blue have been studied in humans, dogs and rats by DiSanto and Wagner, J Pharm Sci 1972, 61:1086-1090 and 1972, 61:1090-1094. Further data on urinary excretion in humans is also available from Moody et al., Biol Psych 1989, 26: 847-858. Combining data on urinary excretion of MB in humans, it is possible to derive an overall model for distribution of MB following single 100 mg dose in a 70 kg subject, assuming instantaneous absorbtion (FIG. 19B). Urinary excretion accounts for 54-98% of the ingested dose. This variability is most likely due to variability in absorbtion, although variability in metabolism cannot be excluded. From urinary excretion data, it is possible to calculate that whole body clearance is 56 mg/kg/hr. Therefore, the dosage required to achieve an effective target tissue concentration of 4 µM is 1.73 mg/kg/day (0.58 mg/kg tds) if there were complete absorbtion. However, from Moody et al., it is clear that total urinary excretion, and hence effective bioavailability, is itself a function of dose. The oral dose required to deliver 1.73 mg/kg/day is approximately 2x the dosage calculated on the basis of whole-body clearance. Therefore the actual required dosage is on the order of 3.2 mg/kg/day. This is close to the minimum routine oral dosage used clinically in humans, eg in the treatment of chronic urinary tract infection (390 mg/day). The maintenance oral dosage in humans is therefore approximately 225 mg/day, or 75 mg tds. Peak tissue levels are reached at approximately 1 hr and the tissue half-life is about 12 hours.

Methylene blue exists in the charged blue oxidised form, and the uncharged colourless reduced leukomethylene blue form. We have shown experimentally in cells that the target tissue concentration in cells required to prevent tau aggregation by 50% (ie the EC50) is 4 µM for reduced methylene blue, and that it is the leuko-form which is preferentially active. It is shown by DiSanto and Wagner (1972) that approximately 78% of the methylene blue recovered in urine is in the reduced form, and from anatomical studies following iv administration, the only form which is bound to tissues is the colourless reduced form, which becomes oxidised to the blue colour on exposure to air after post-mortem dissection. The only form of methylene blue which crosses the blood-brain barrier after iv administration is the reduced form (Muller, Acta Anat 1992, 144:39-44 and Becker and Quadbeck, 1952). Therefore, orally absorbed methylene blue is very rapidly reduced in the body, and remains so until excretion, possibly undergoing further chemical modification which stabilises it in a reduced form.

It is highly likely that variability in oral absorbtion is determined largely by the efficiency of initial reduction in the GI tract. One way to achieve more reliable absorbtion is therefore be to pre-reduce methylene blue with ascorbic acid. We have shown from in vitro studies that this conversion is rather slow, so that it takes 3 hours to achieve 90% reduction of methylene blue in water in the presence of 2× mg ratio of ascorbic acid. Therefore, the dosage of methylene blue which is most likely to ensure reliable absorbtion will be 3.5 mg/kg/day of methylene blue pre-reduced for at least 3 hours in the presence of 7 mg/kg/day of ascorbic acid.

It is also possible that MB may be active at lower concentrations in man, and that a range of clinically feasible doses would be therefore 20 mg tds, 50 mg tds or 100 mg tds, combined with 2×mg ratio of ascorbic acid in such a manner as to achieve more than 90% reduction prior to ingestion.

Formulation and Administration of Therapeutics

Suitable compounds, such as those with a formula as shown above or their pharmaceutically-acceptable salts, may be incorporated into compositions of this aspect of the present invention after further testing for toxicity. The compositions may include, in addition to the above constituents, pharmaceutically-acceptable excipients, carriers, buffers, stabilisers or other materials well known to those skilled in the art. Such materials should be non-toxic and should not interfere with the efficacy of the active ingredient. The precise nature of the carrier or other material may depend on the route of administration.

Where the composition is formulated into a pharmaceutical composition, the administration thereof can be effected parentally such as orally, in the form of powders, tablets, coated tablets, dragees, hard and soft gelatine capsules, solutions, emulsions or suspensions, nasally (e.g. in the form of nasal sprays) or rectally (e.g. in the form of suppositories). However, the administration can also be effected parentally such as intramuscularly, intravenously, cutaneously, subcutaneously, or intraperitoneally (e.g. in the form of injection solutions).

Where the pharmaceutical composition is in the form of a tablet, it may include a solid carrier such as gelatine or an adjuvant. For the manufacture of tablets, coated tablets, dragees and hard gelatine capsules, the active compounds and their pharmaceutically-acceptable acid addition salts can be processed with pharmaceutically inert, inorganic or organic excipients. Lactose, maize, starch or derivatives thereof, talc, stearic acid or its salts etc. can be used, for example, as such excipients for tablets, dragees and hard gelatine capsules. Suitable excipients for soft gelatine capsules are, for example, vegetable oils, waxes, fats, semi-solid and liquid polyols etc.

Where the composition is in the form of a liquid pharmaceutical formulation, it will generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may also be included. Other suitable excipients for the manufacture of solutions and syrups are, for example, water, polyols, saccharose, invert sugar, glucose, trihalose, etc. Suitable excipients for injection solutions are, for example, water, alcohols, polyols, glycerol, vegetable oils, etc.

Suitable excipients for suppositories are, for example, natural or hardened oils, waxes, fats, semi-liquid or liquid polyols etc.

Moreover, the pharmaceutical preparations may contain preserving agents, solubilizers, viscosity-increasing substances, stabilising agents, wetting agents, emulsifying agents, sweetening agents, colouring agents, flavouring agents, salts for varying the osmotic pressure, buffers, or coating agents.

For intravenous, cutaneous or subcutaneous injection, or intracatheter infusion into the brain, the active ingredient will be in the form of a parenterally-acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilisers, buffers and/or other additives may be included, as required.

A composition according to the present invention may be administered alone, or in combination with other treatments, either simultaneously or sequentially, dependent upon the condition or disease to be treated.

In accordance with the present invention, the formulations provided herein may be used for the prophylaxis or treatment of Alzheimer's disease, motor neuron disease, Lewy body disease, Pick's disease or Progressive Supranuclear Palsy, or any other condition or disease in which induced conformational polymerisation of a protein is implicated (see FIG. 5). In particular, as described in detail below, the formulation may be used for the blocking, modulation and inhibition of pathological tau-tau association.

Examples of the techniques and protocols mentioned above can be found in "*Remington's Pharmaceutical Sciences*", $16^{th}$ edition, Osol, A. (ed.), 1980.

In a further aspect, the present invention relates to the use of a composition of the preceding aspect, in the diagnosis, prognosis or treatment of a condition in which induced conformational polymerisation of a protein is implicated. The condition may be a disease such as Alzheimer's disease, or any other condition of the type described herein.

Use of Diffusion Constant as a Screen

As stated above, by converting a compound into, and/or stabilising its reduced form, the inhibitory potency of the compound can be optimised.

However, as described in more detail in the examples hereinafter, surprisingly, the redox potential of a compound does not directly determine its inhibitory activity with respect to induced conformational polymerisation of proteins, and that, therefore, neither the oxidation model nor a catalytic reduction model are relevant to an understanding of the activity of compounds as tau-tau aggregation inhibitors.

The inventors have found that there is a strong inverse correlation between the inhibitory potential of a compound towards tau-tau binding and the square or third power of its diffusion coefficient.

The diffusion coefficient is determined by the amount of stacking of discharged molecules at a cathode. Experimentally, this can be evaluated by measuring the current flow in a redox cell at the reduction potential. The diffusion coefficient is inversely correlated with the degree of aggregation of the discharged (i.e. reduced) species within the Helmholtz layer forming at the cathode. These aggregates form by pi-bonded stacking interactions across the phenol ring systems.

In one model, the lower the diffusion coefficient, the higher the tendency to stack, and the more potent the compound is in inhibiting induced conformational polymerisation of proteins such as tau-tau binding, as reflected by a low $K_i$.

The stacking of diaminophenothiazines may be less favoured when the molecule is in the oxidised form, since this form is charged, and so can be envisaged to repel other, like molecules. This phenomenon may thus explain the greater efficacy of the reduced form of diaminophenothiazines in the inhibition of tau aggregation (see e.g. FIG. 9).

Thus an assessment of the diffusion coefficient (dependent on 'stackability', which is in turn dependent on shape and charge) can be a useful step in the development of effective modulators. One such sterically-relevant parameter is diffusion coefficient which can be diminished by providing diaminophenothiazines in their reduced form.

Thus, the present inventors teach herein that the efficacy of a compound in the blocking, modulation or inhibition of induced conformational polymerisation of a protein (hereinafter referred to as "inhibitory potency" can be tested in an assay method which includes the step of measuring the diffusion coefficient of the compound.

Hence, in its most general form, the present invention provides a method of screening for an agent that blocks, modulates or inhibits induced conformational polymerisation of a protein, which method includes the step of measuring the diffusion coefficient of the agent. The use of the diffusion coefficient value, and in particular the square or third power of its diffusion coefficient, in assessing the inhibitory potency of a phenothiazine (e.g. as described above) for the treatment of a disease as described herein forms a further aspect of the present invention.

The step of measuring the diffusion coefficient of the test agent may be incorporated at any stage of a larger screening programme for identifying or optimising putative or established modulators. The larger method will typically further include assay steps as described herein, or in the prior art (e.g. WO 96/30766). Thus, in the latter case for instance, when one wishes to screen for agents which block, modulate or inhibit tau-tau aggregation, the method may include the steps of contacting:

(a) a tau protein or a derivative thereof containing the tau core fragment, with;
(b) a substance to be tested for its ability to block, modulate or inhibit tau-tau aggregation; and
(c) a labelled tau protein or a labelled derivative thereof which is capable of binding to the tau protein of step (a) or a tau protein or a derivative thereof which is distinct from the tau protein of step (a) and also capable of binding to the tau protein of step (a).

The diffusion coefficient may be measured by any suitable means, for instance according to the method of Murthy and Reddy (J Chem. Soc., Faraday Trans J 1984, 80. 2745-2750). This publication also included some determined values of diffusion coefficients for phenothiazine dyes and its content is specifically incorporated herein by reference.

Thus, the diffusion coefficient may suitably be measured by cyclic voltammetry in an aqueous acidic medium, whereby the magnitude of current flow in a redox cell is tested at the reduction potential of the compound.

The method may include the step of performing further tests on the agent, e.g. to ascertain its specificity as an inhibitor or modulator of induced conformational polymerisation of a particular protein (e.g. tau), or to determine its pharmaceutical acceptability or suitability as an agent for administration to an animal.

The surprising teaching as provided herein, that the efficacy of an agent in blocking, modulating or inhibiting induced conformational polymerisation of a protein is dependent, at least in part, on the diffusion coefficient of the agent, can be utilised in the optimisation of an agent's efficacy. The present inventors have established that an agent's inhibitory potency towards induced conformational polymerisation of a protein is inversely related to the square or third power of its diffusion coefficient. In other words, the inhibitory potency of an agent can be optimised by providing the agent in a form in which its diffusion coefficient is minimised.

Thus, in a further aspect, the present invention concerns a method of optimising the efficacy of an agent in blocking, modulating or inhibiting induced conformational polymerisation of a protein, which method includes the step of minimising the diffusion coefficient of the agent.

In a further aspect, the present invention provides a pharmaceutical composition for the prophylaxis or treatment of a condition in which induced conformational polymerisation of a protein occurs, the composition comprising a compound which is provided in, or converted into, a form in which its diffusion coefficient is minimised.

This, and further, aspects of the invention will be better understood by reference to the following figures and experimental data, given only by way of example.

FIGURES

Figure 1:
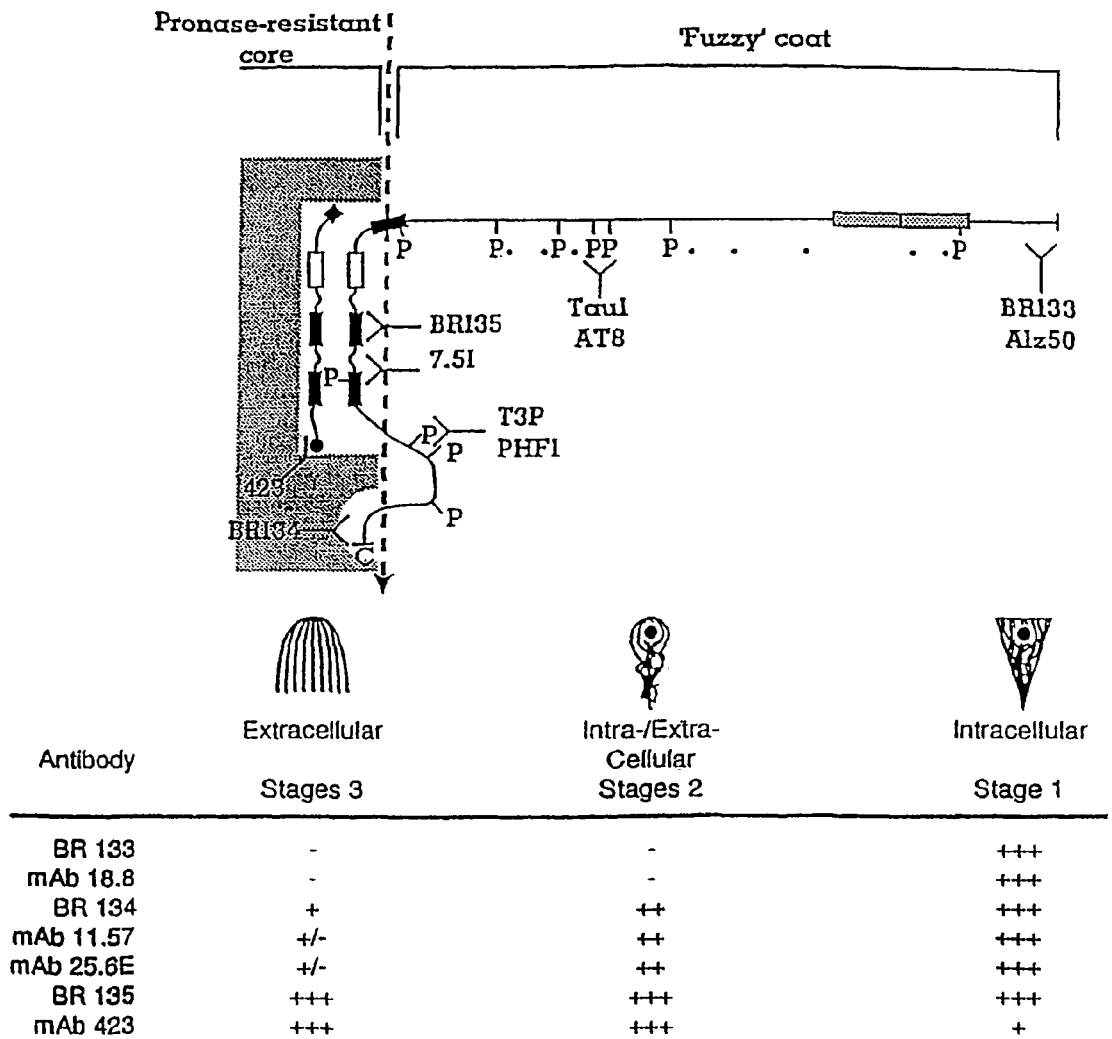
FIG. 1 shows a schematic illustration of the structure of a paired helical filament (top) and the immunochemistry of neurofibrillary tangles during progression of Alzheimer's disease (bottom).
Figure 2:
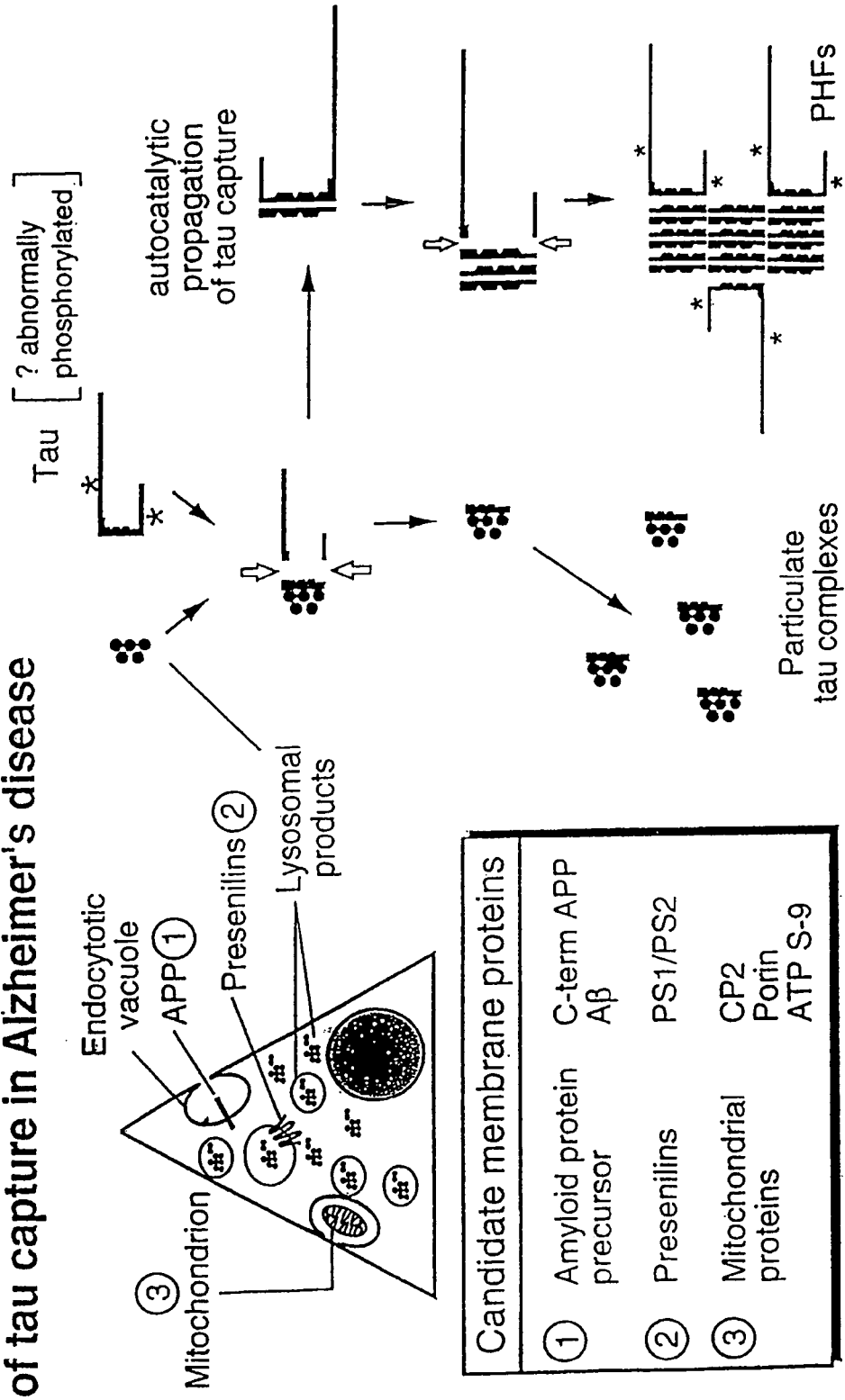
FIG. 2 shows a conceptual scheme wherein critical nucleating factors provide a 'seed' which initiates tau capture, which then becomes autocatalytic.
Figure 3:
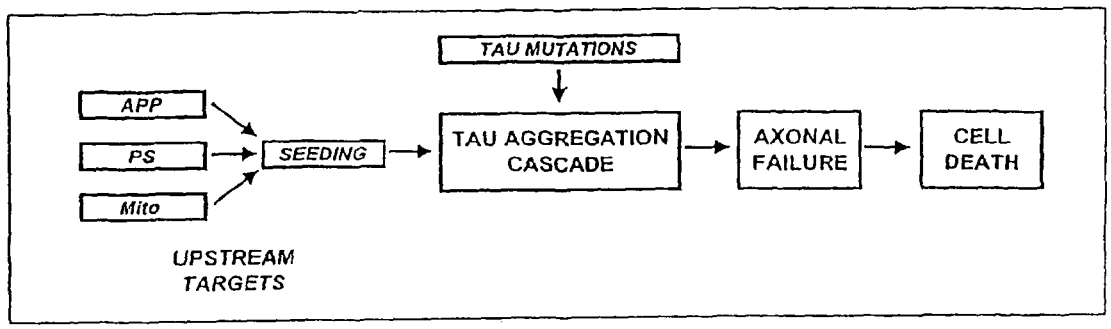

FIG. 3 shows a putative pathogenic model of Alzheimer's disease. Tau aggregation is a proximal process prior to failure of axonal transport and consequent neuronal death. The tau aggregation cascade can be triggered either by a seeding/ nucleation event arising from upstream changes or from primary mutations in the tau gene.

Figure 4:
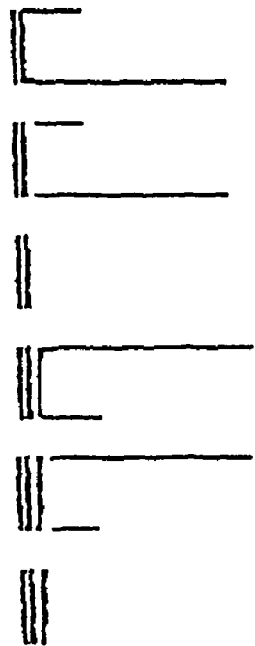

FIG. 4 shows how induction of full-length tau can lead to its conversion into the 12 kD fragment, provided there is some preexisting 12 kD tau in the cell.

FIG. 5a-b shows a table listing proteins which play a role in diseases of protein aggregation. Also listed are the diseases themselves, the aggregating domain and/or mutation believed to be involved, and the putative (maximum) fibril subunit size. One or more literature references for each protein is given.

Figure 6:
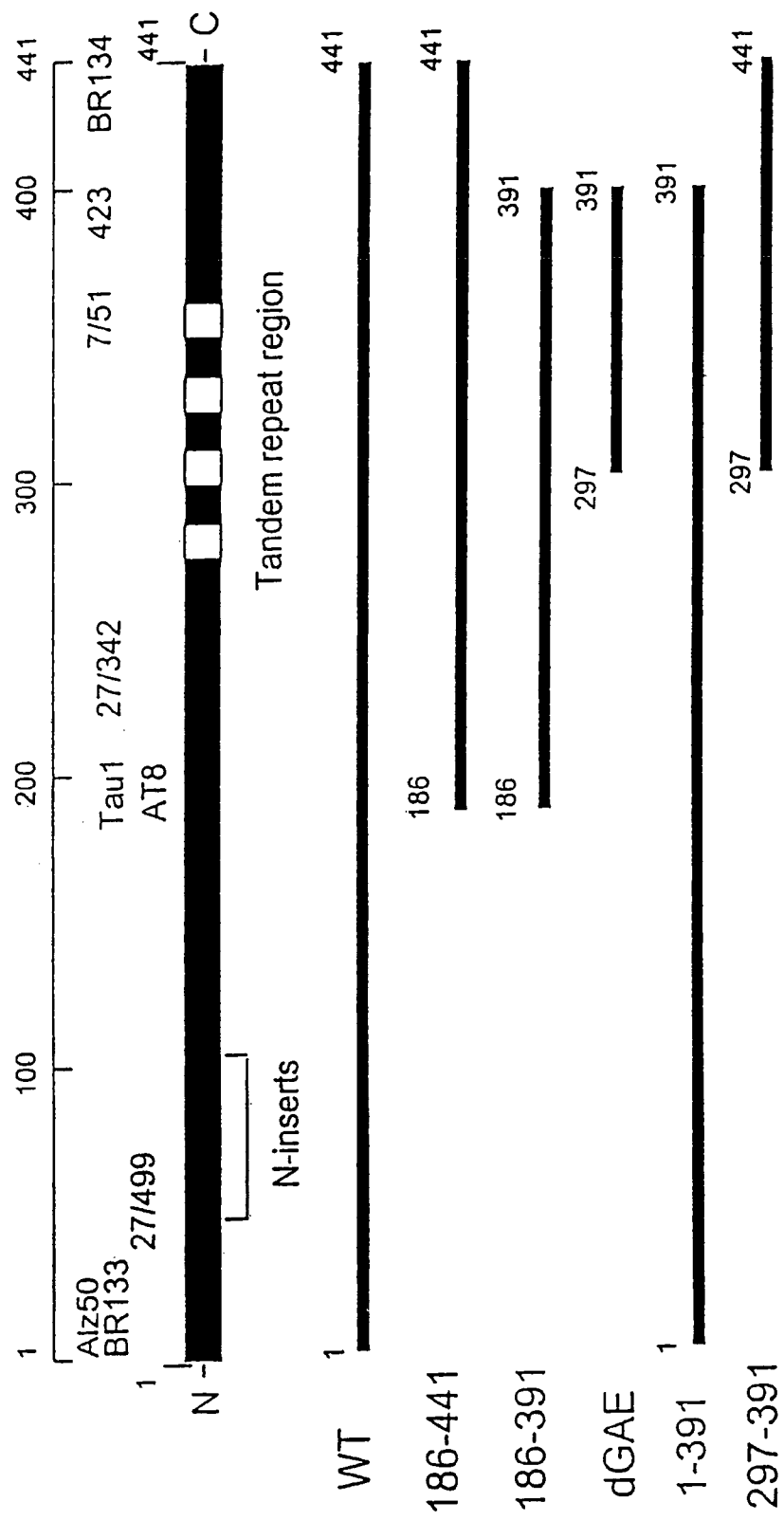

FIG. 6 shows a schematic illustration of the binding sites of various monoclonal antibodies to different forms of N- and C-truncated tau.

FIG. 7A and FIG. 7B show the nucleotide (SEQ ID NO: 1) and predicted amino acid sequences (SEQ ID NO: 2) of a human tau protein isoform. The sequence was deduced from cDNA clone htau40.

FIG. 8 shows the structures of thionine, tolonium chloride, chlorpromazine and tacrine.

FIG. 9 gives cellular assay data for diaminophenothiazines, and a structurally related anthroquinone along with apparent KI values, determined as described herein. In the Figures and Examples herein, a further parameter, B50, has been calculated to express activity in a manner directly related to the conditions of the cell-based assay, and therefore providing an indication of the tissue concentration which would be required to achieve the corresponding activity in vivo. The B50 value is the concentration of test compound used in the cell assay at which relative production of the 12 kD band from full-length tau was reduced to 50% of that observed in the absence of the compound. There is a simple linear relationship between apparent KI value and B50 value as follows: RECTIFIED SHEET (RULE 91)

$$\text{Cellular } B50 = 0.0217 \times KI$$

In order to compare the relative usefulness of compounds as therapeutics, it may be desired to calculate an LD50 value. Where inhibitory properties are similar, preferred compounds for clinical use may be those which have the highest LD50 value. A therapeutic index (RxIndx) may be calculated for each of compounds tested in the cell assays as follows:

$$RxIndx = LD50/B50$$

Toxicity of the compounds may be measured by cell numbers after 24 hrs exposure to the compound using a lactate dehydrogenase assay kit TOX-7 (Sigma Biosciences) according to the manufacturer's instructions after lysis of remaining cells. Alternatively a kit from Promega UK (CytoTox 96) may be used, again according to the manufacturer's instructions.

Figure 10:
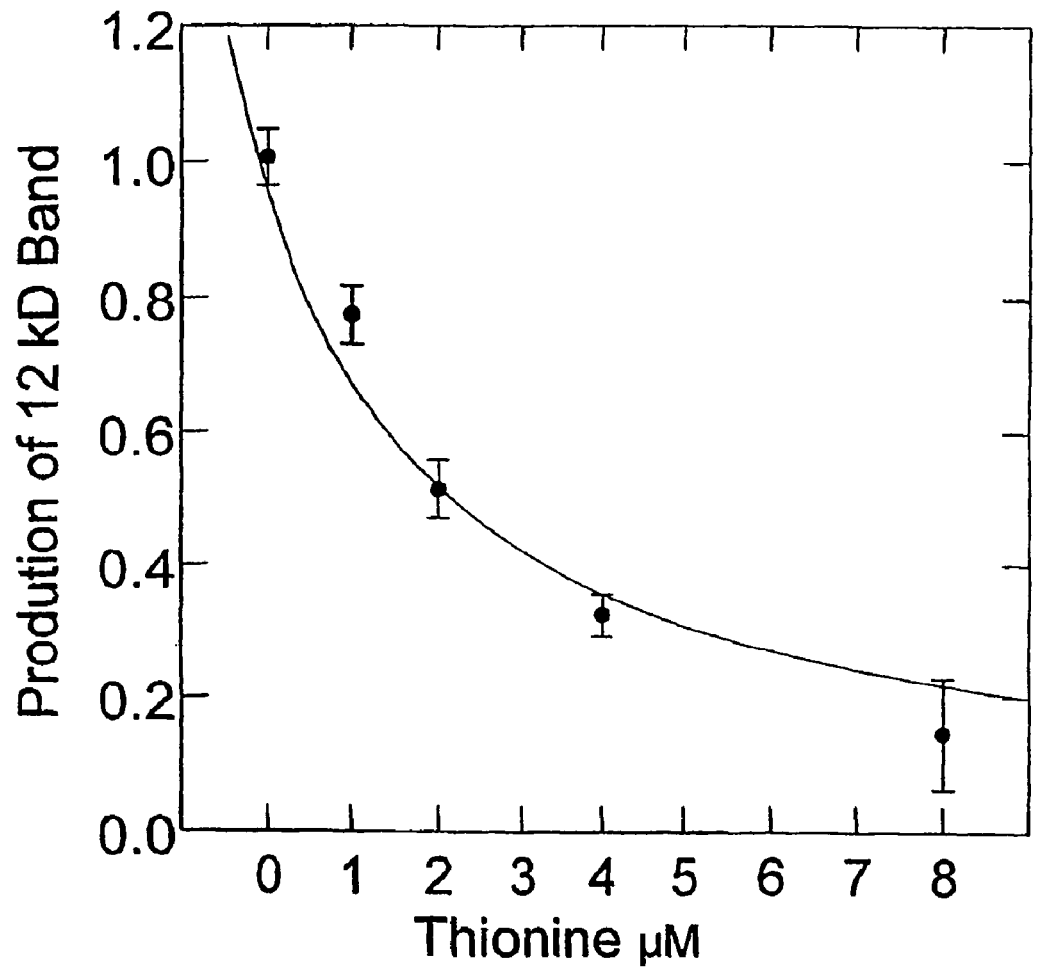

FIG. 10 shows the results of using reduced thionine in the present invention, based on a data set of 7 experiments. The observed cell data for production of the 12 kD band can be fitted closely (ie observed vs predicted correlation coefficient >0.9), to a standard function describing inhibition of tau-tau binding in vitro. To obtain this fit, two assumptions need to be made, which are consistent with results from other cell-based and in vitro studies:
1) the intracellular concentration of tau is approximately 500 nM;
2) the tau-tau binding affinity is 22 nM.

using these assumptions, the function for cellular activity predicted via standard inhibition model is:

$$\text{Activity} = [\text{tau}]/([\text{tau}]Kd^*(1+[\text{thionine}]/KI))$$

can be solved by standard numerical methods to derive a value for apparent KI. As indicated, the value for the reduced form of thionine is 100 nM. which is essentially the same as that observed for tau-tau binding in vitro at a tau concentration of 500 nM, where the Kd value for tau-tau binding is known to be 22 nM. Therefore, the activity of thionine, where the read-out is production of the 12 kD truncation product from full-length tau, can be explained quantitatively on the basis of extent of inhibition of the tau-tau binding occurring through the repeat domain within the cell. This confirms that the extent of tau-tau binding determines production of the proteolytically stable core tau unit of the PHF within the cell.

All subsequent cellular analyses of activities of other compounds are reported in the same standardised format, with the same assumptions regarding intracellular tau concentration (500 nM) and tau-tau binding affinity (22 nM) through the repeat domain.

Figure 11:
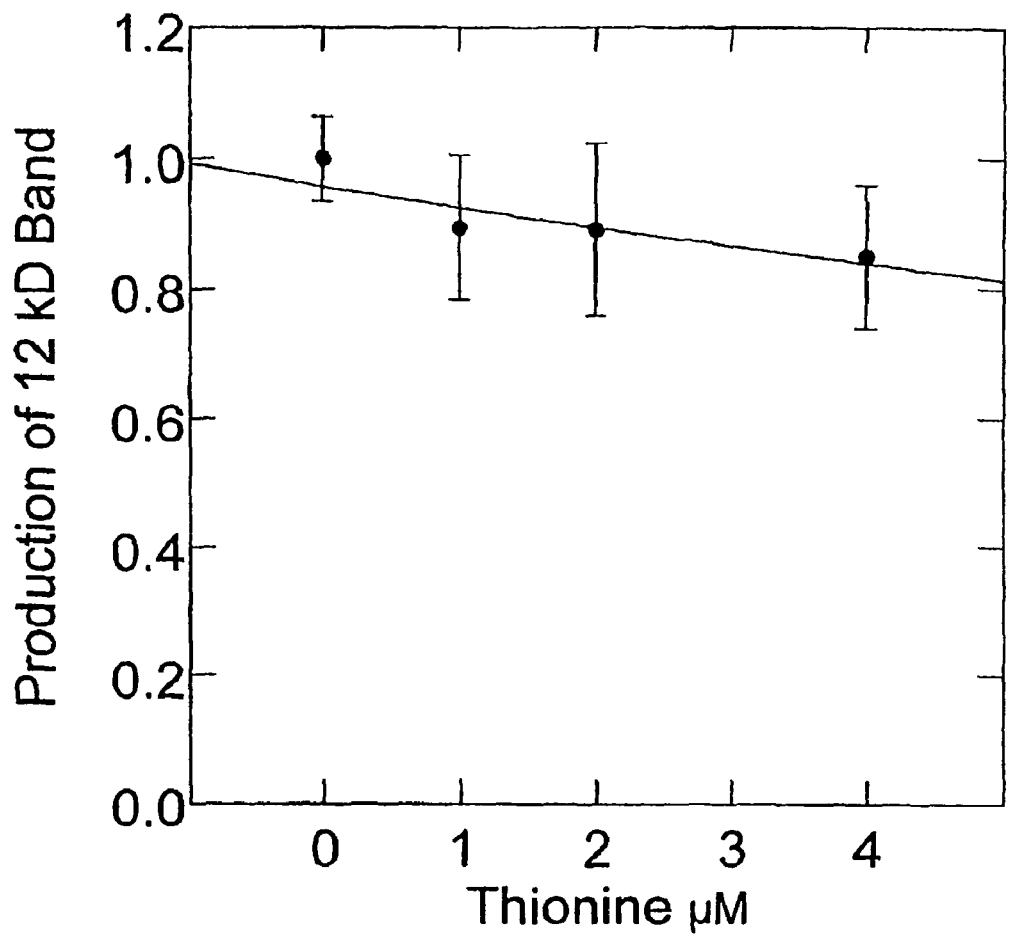

FIG. 11 shows the results for conditions in which the reducing agents have been omitted (i.e. oxidised thionine cf. FIG. 10).

Again cellular activity is predicted via standard inhibition model:

$$\text{Activity} = [\text{tau}]/([\text{tau}]Kd^*(1+[\text{Ox. Thio.}]/KI))$$

In this case, thionine now has an apparent KI value of 1200 nM. This confirms that the diaminophenothiazines require to be in the reduced form for activity. A similar conclusion was derived from analysis of in vitro binding data (results not shown).

Figure 12:
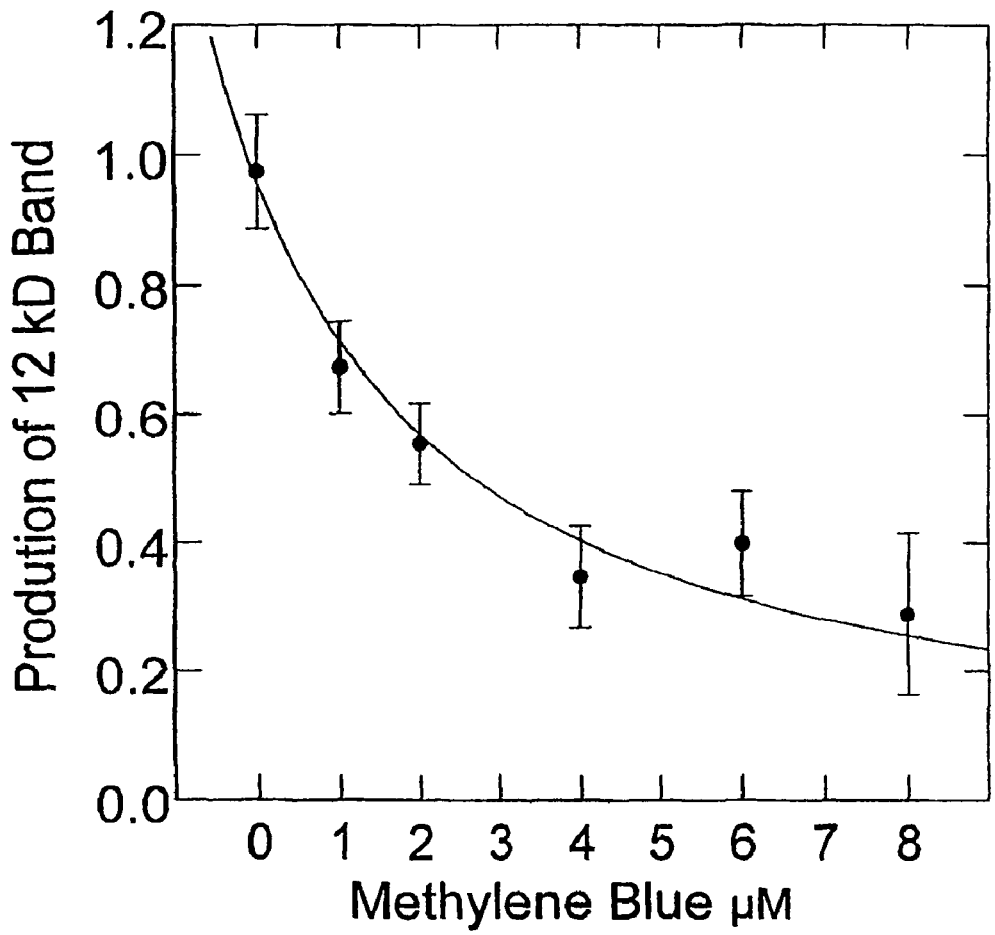

FIG. 12 shows that by using reducing or partially reducing conditions methylene blue appears much more active in the cell-based assay than predicted from in vitro studies in which the time course of the assay (1-2 hours) had not been sufficient to achieve reduction.

Cellular activity is again predicted via standard inhibition model:

$$\text{Activity} = [\text{tau}]/([\text{tau}]Kd^*(1+[\text{MB}]/KI))$$

In the cell assay, the apparent KI value for methylene blue is 123 nM, which is within the same range as thionine and tolonium chloride. As indicated in FIG. 9, the corresponding brain tissue concentration (i.e. B50 value) required to inhibit tau aggregation would be 2-3 μM.

Figure 13:
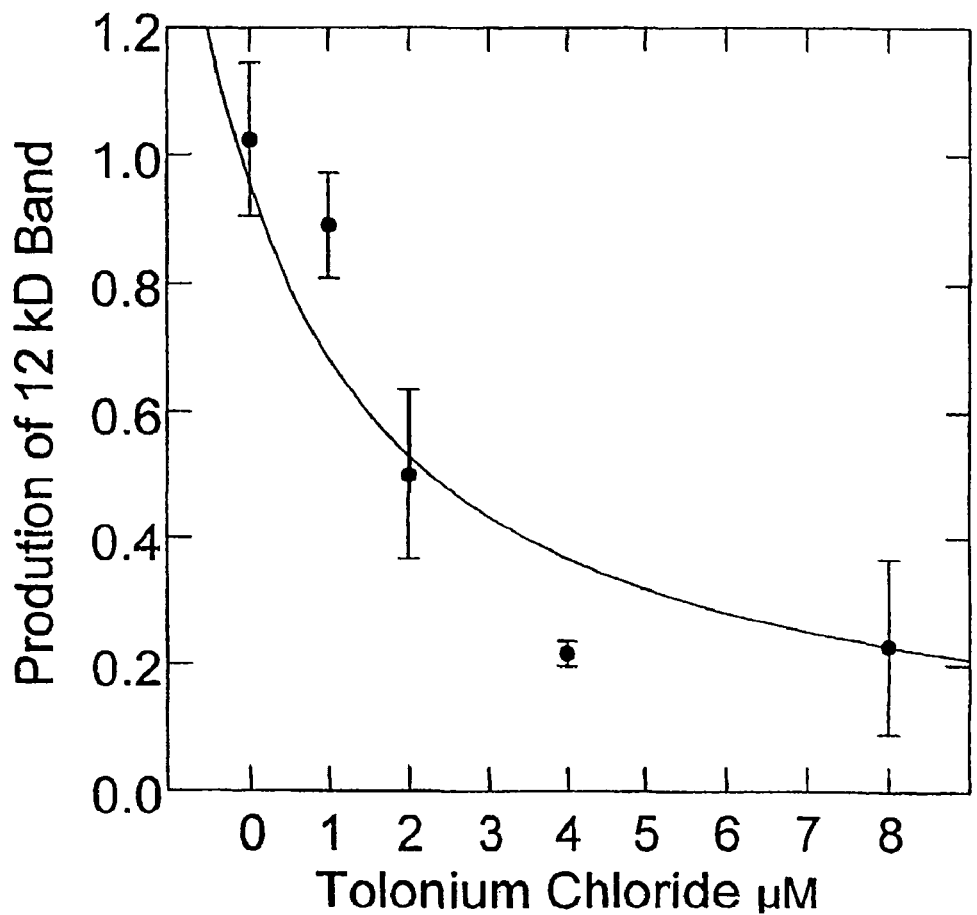

FIG. 13 shows corresponding cell-based activity data for reduced tolonium chloride, indicating again that the predicted KI value derived from in vitro studies can be used to describe production of the 12 kD fragment from full-length tau in cells.

Cellular activity is predicted via standard inhibition model:

$$\text{Activity} = [\text{tau}]/([\text{tau}]Kd^*(1+[TC]/KI))$$

This provides further confirmation of the validity of the mathematical analysis procedure used.

Figure 14:
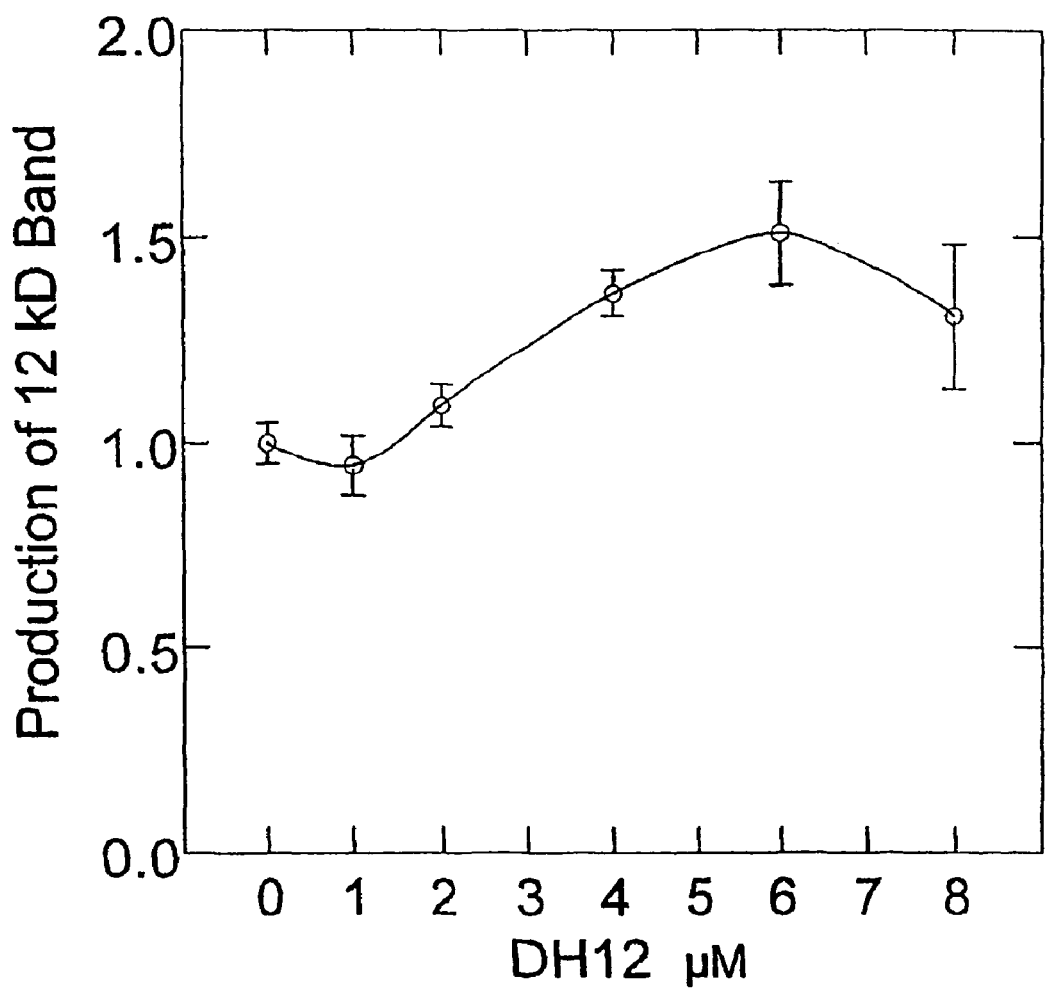

FIG. 14 shows that DH12 (anthroquinone) which is structurally related to the diaminophenothiazines is inactive in the conditions of the assay.

Figure 15:
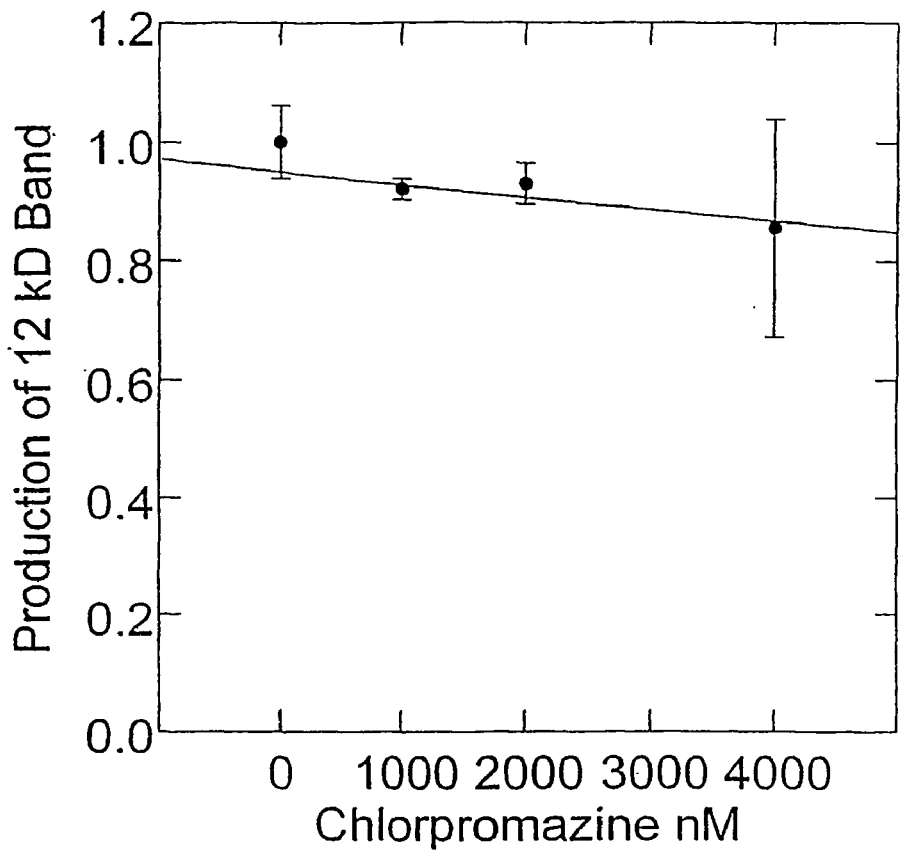
Figure 16:
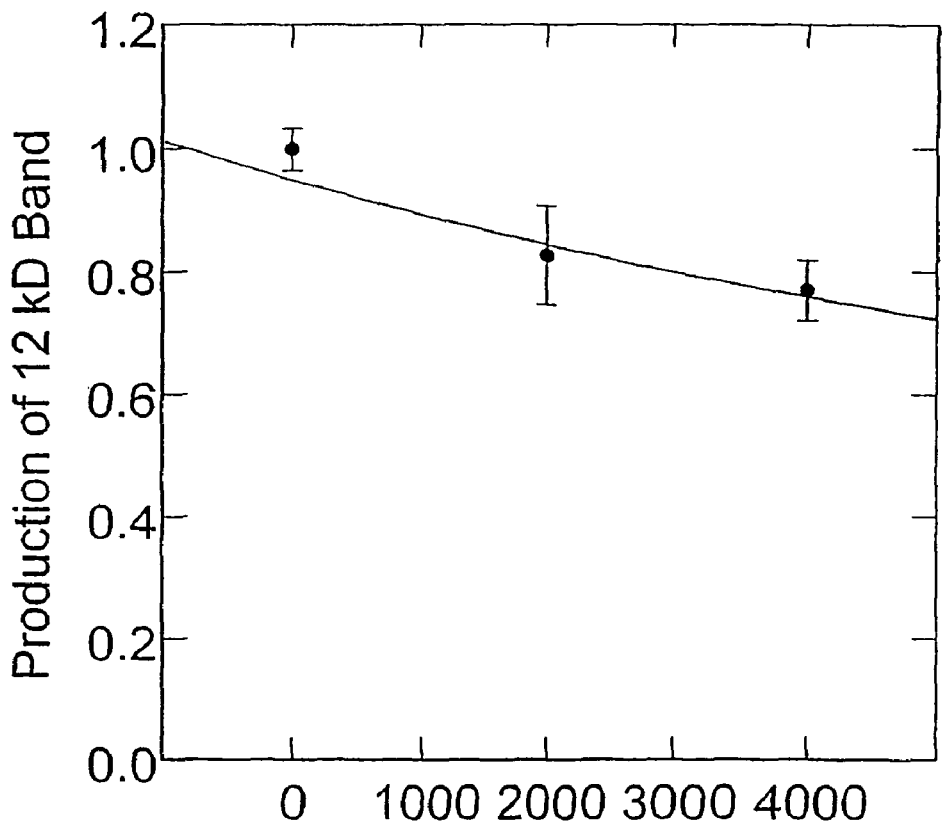

FIGS. 15 & 16 show similar analyses to those given above in FIGS. 9-14, but for chlorpromazine and tacrine respectively. Using the same assumptions (tau concentration 415 nM, and tau-tau binding Kd 22 nM), and cellular activity predicted via standard inhibition model:

$$\text{Activity} = [\text{tau}]/([\text{tau}]Kd^*(1+[\text{cpz}]/KI))$$

the apparent KI values for chlorpromazine and tacrine (2117 nM and 802 nM respectively) are greater than anticipated from the in vitro studies.

Figure 17:
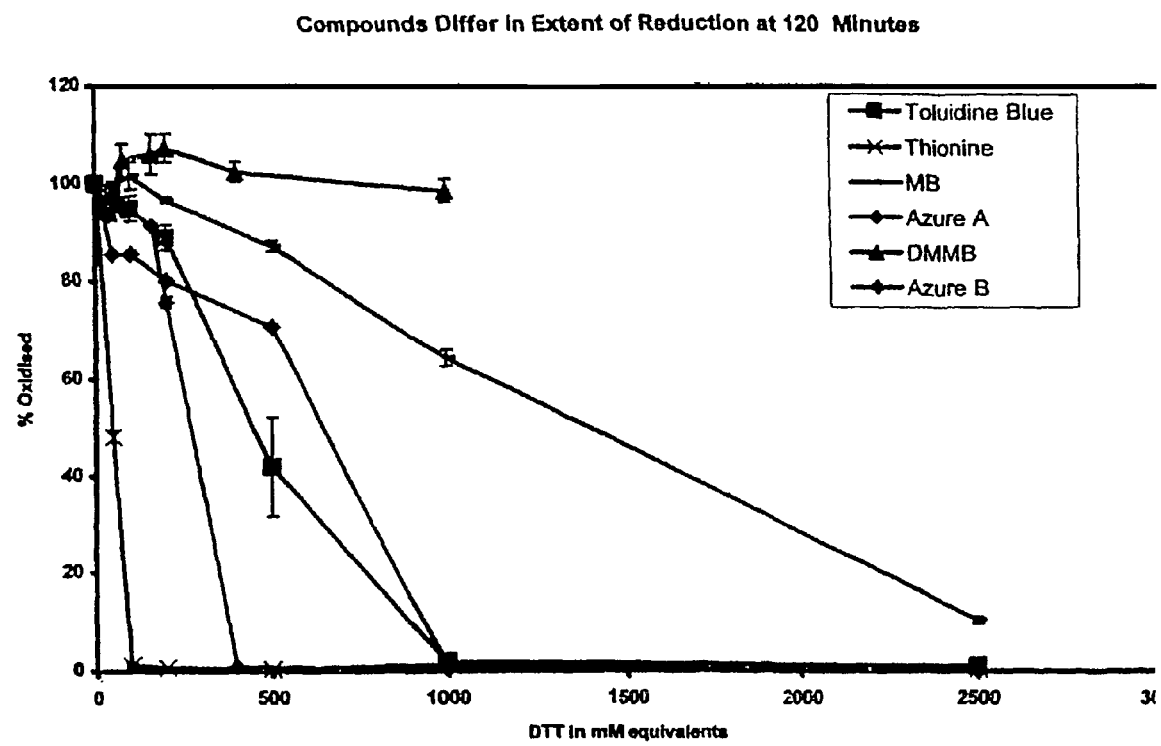

FIG. 17 shows the extent of reduction of various compounds in the presence of DTT.

Figure 18:
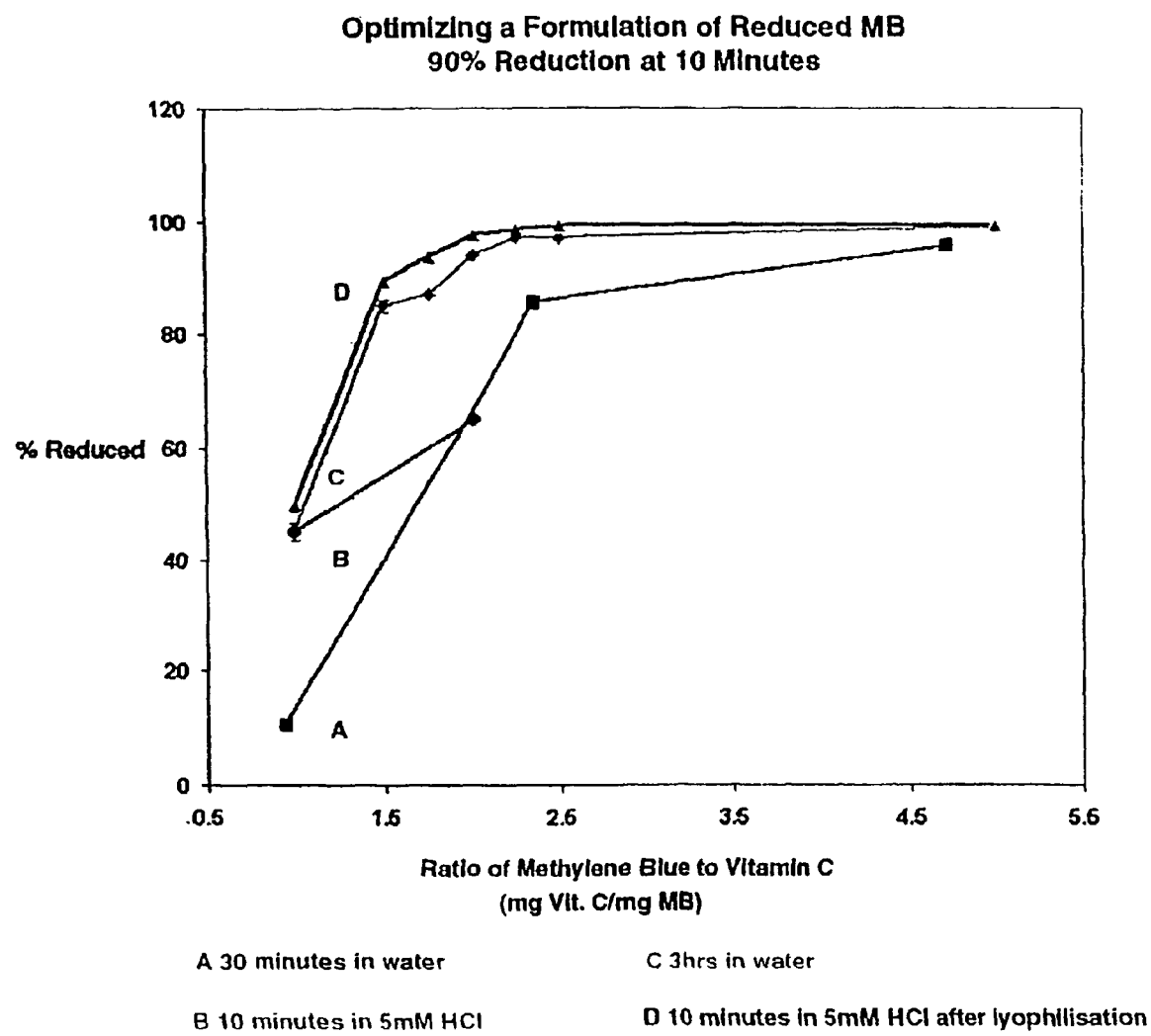

FIG. 18 shows the percentage reduction of MB plotted against the ratio of MB:Vitamin C.

Figure 19A:
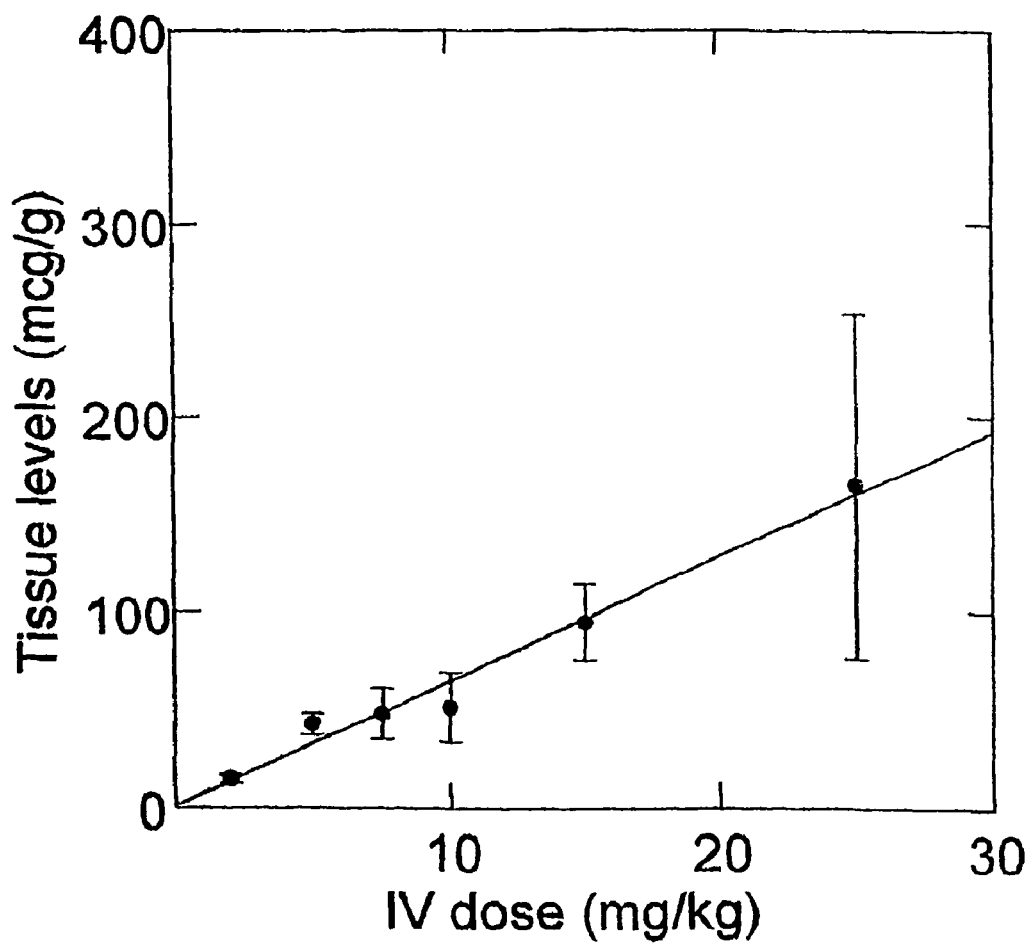

FIG. 19(a) shows that by assuming a target tissue concentration of 4 μM (i.e. 1.5 μg/g) it is possible to determine from the data of DiSanto and Wagner (1972) that tissue concentrations of this order would be achieved at an IV dosage of 0.11 mg/kg.

Figure 19B:
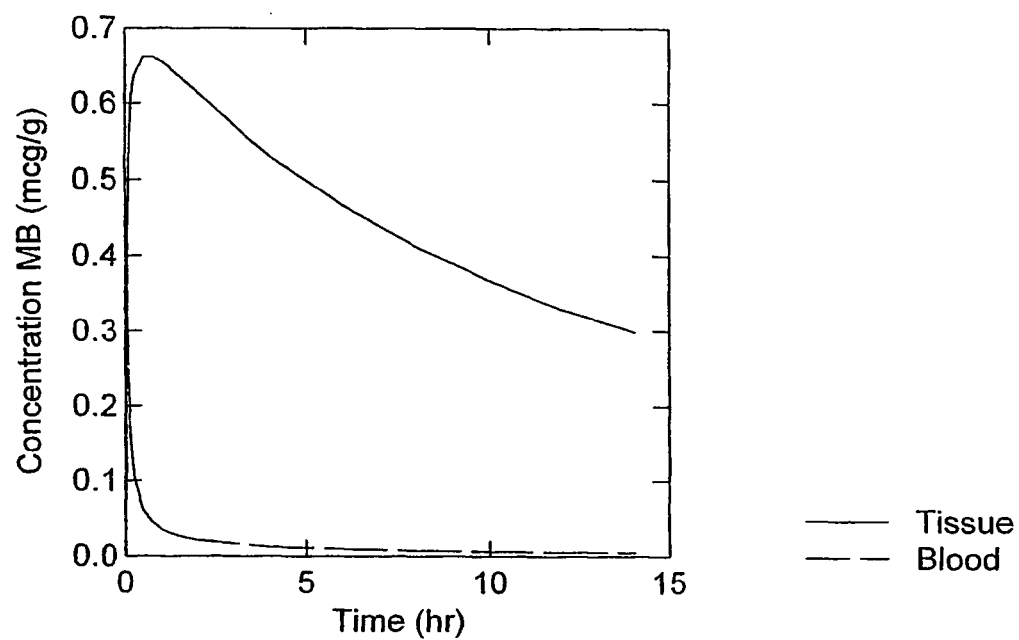

FIG. 19(b) shows a model for the distribution of MB following a single 100 mg dose in a 70 kg subject, assuming instantaneous absorbtion.

FIG. 20 summarises the results for the transient expression of tau fragments in 3T3 and COS-7 cells based upon data from both microscopical and biochemical experiments.

Expression of recombinant tau fragments in eukaryotic cells was performed as follows. Eight tau constructs, transiently expressed in 3T3 cells and COS-7 cells were examined by immunocytochemistry and immunoblots. The extent of expression in each cell type was given semi-quantitatively on the basis of both sets of results: −, no detectable expression; ±, very weak immunoreactivity; + to ++++, increasing levels of positive immunoreactivity. In all cases, mAb 7.51 was used with each construct to obtain the results. In addition the specificity was confirmed for each construct by using a panel of antibodies against different domains of tau protein (mAbs 499, T14, Tau1, 342, 7.51, 423 and T46). Kozak sequences were absent in the first six contructs, but were present in the cDNA constructs 7 and 8.

Figure 21:
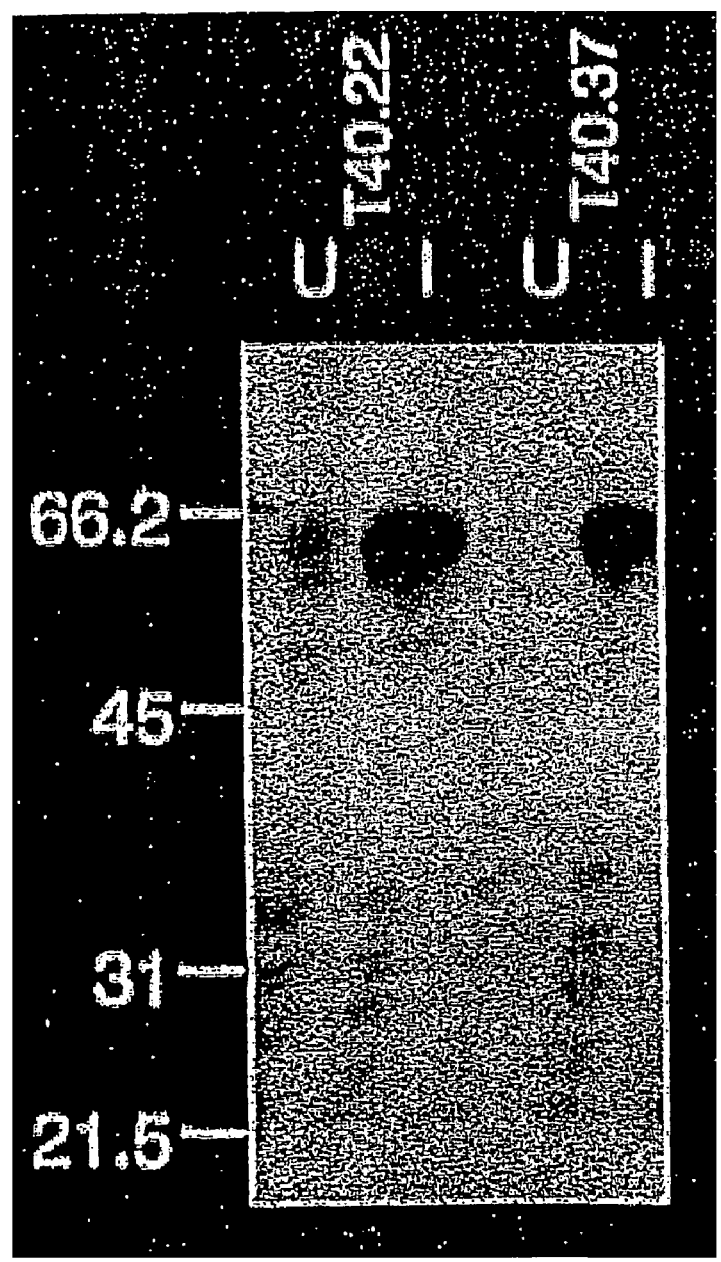

FIG. 21 illustrates the inducible expression of full-length human tau in 3T6 fibroblasts in two cell lines. T40.22 shows low level background leakage of full length tau in the uninduced state ("U"), and high levels of expression after addition of IPTG (i.e. induced, "I"). T40.37 shows the same, but lower levels of expression without induction.

Figure 22:
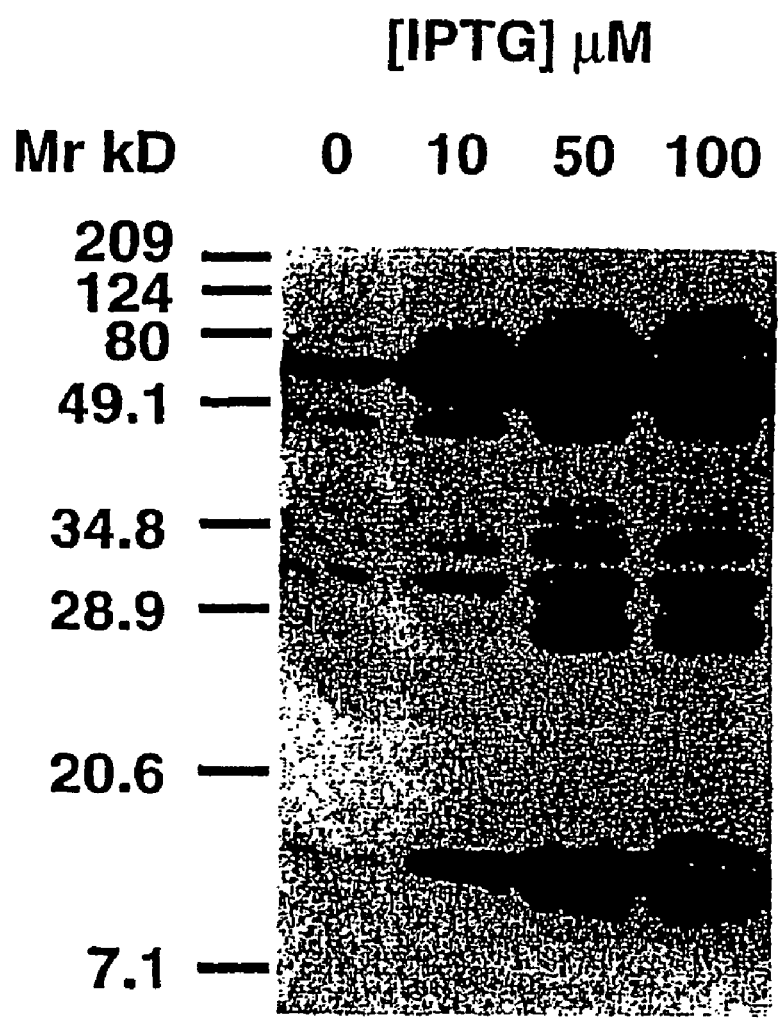

FIG. 22 shows a result of a triple vector system. A vector permitting very low level constitutive expression of the 12 kD fragment was introduced into cells lines in which inducible expression of full length tau had already been achieved (in fact cell line T40.22 shown in FIG. 21 above). Low levels of IPTG are introduced to induce expression of full-length tau. At 0 μM IPTG, there is very low level expression of the 12 kD band, and low "background leakage" expression of full-length tau. As progressively more full-length tau is induced by introducing higher levels of IPTG, more of the full-length tau is converted to the 12 kD species.

Figure 23:
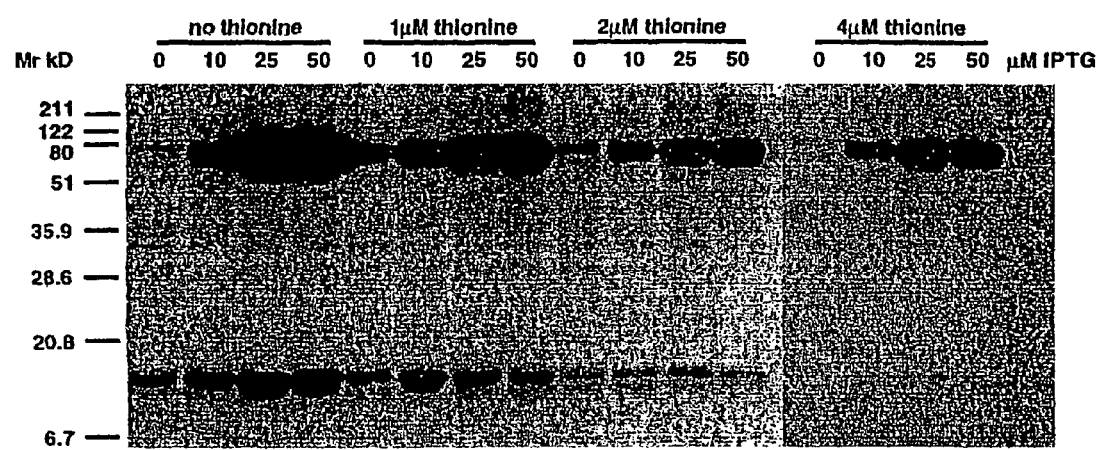

FIG. 23 shows the inhibitory effects of reduced thionine. In each set of lanes, there is inducible production of the 12 kD band in the presence of increasing concentrations of IPTG inducing higher levels of T40. As the thionine concentration is increased, the production of the 12 kD band from T40 is suppressed.

Figure 24:
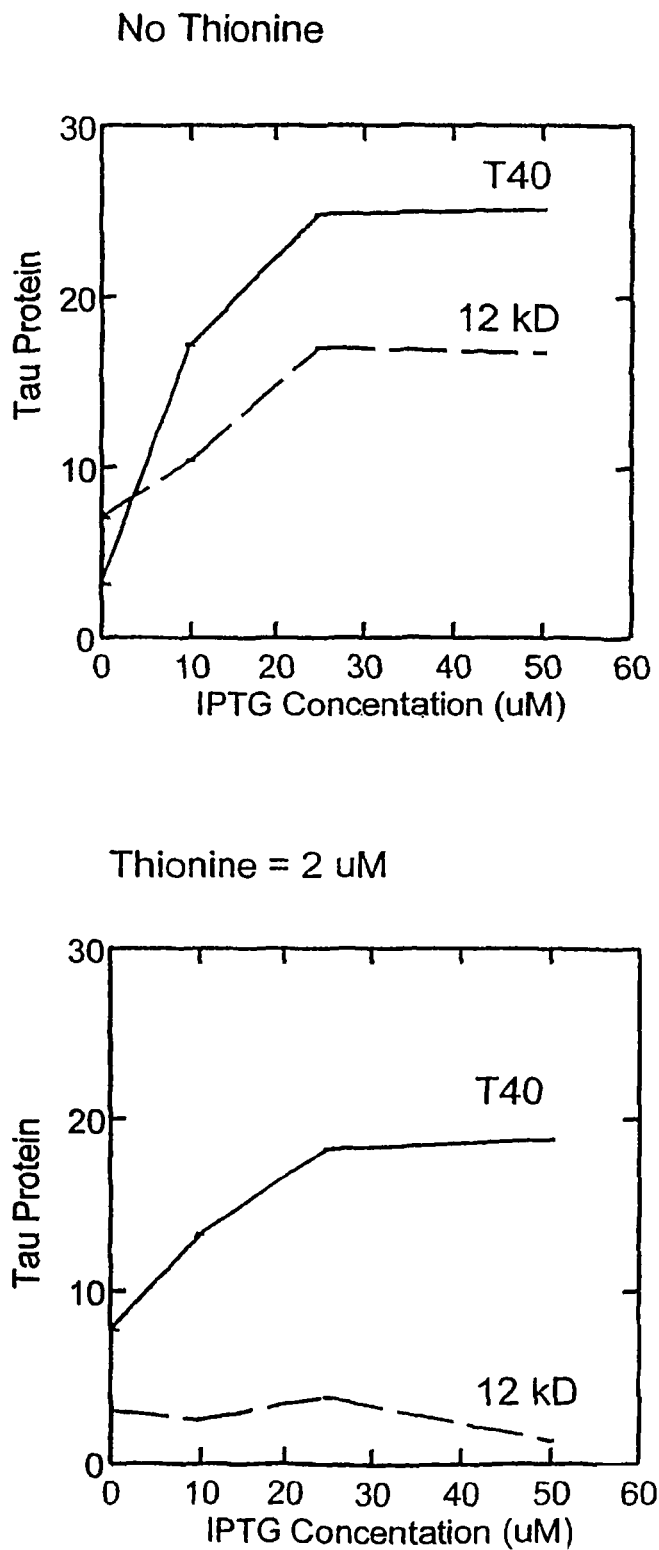

FIG. 24 shows quantitatively the results of FIG. 23. In the absence of thionine, induction of T40 at increasing concentrations of IPTG leads to a corresponding increased production of the 12 kD fragment. In the presence of 2 μM thionine, there is still induction of T40, but it is not converted into the 12 kD fragment.

FIG. 25 shows comparative in vitro KI values for various compounds, in nM. The KI values relate to the particular assay conditions used (500:1 DTT:compound, 120 minutes—see FIG. 17).

Figure 26:
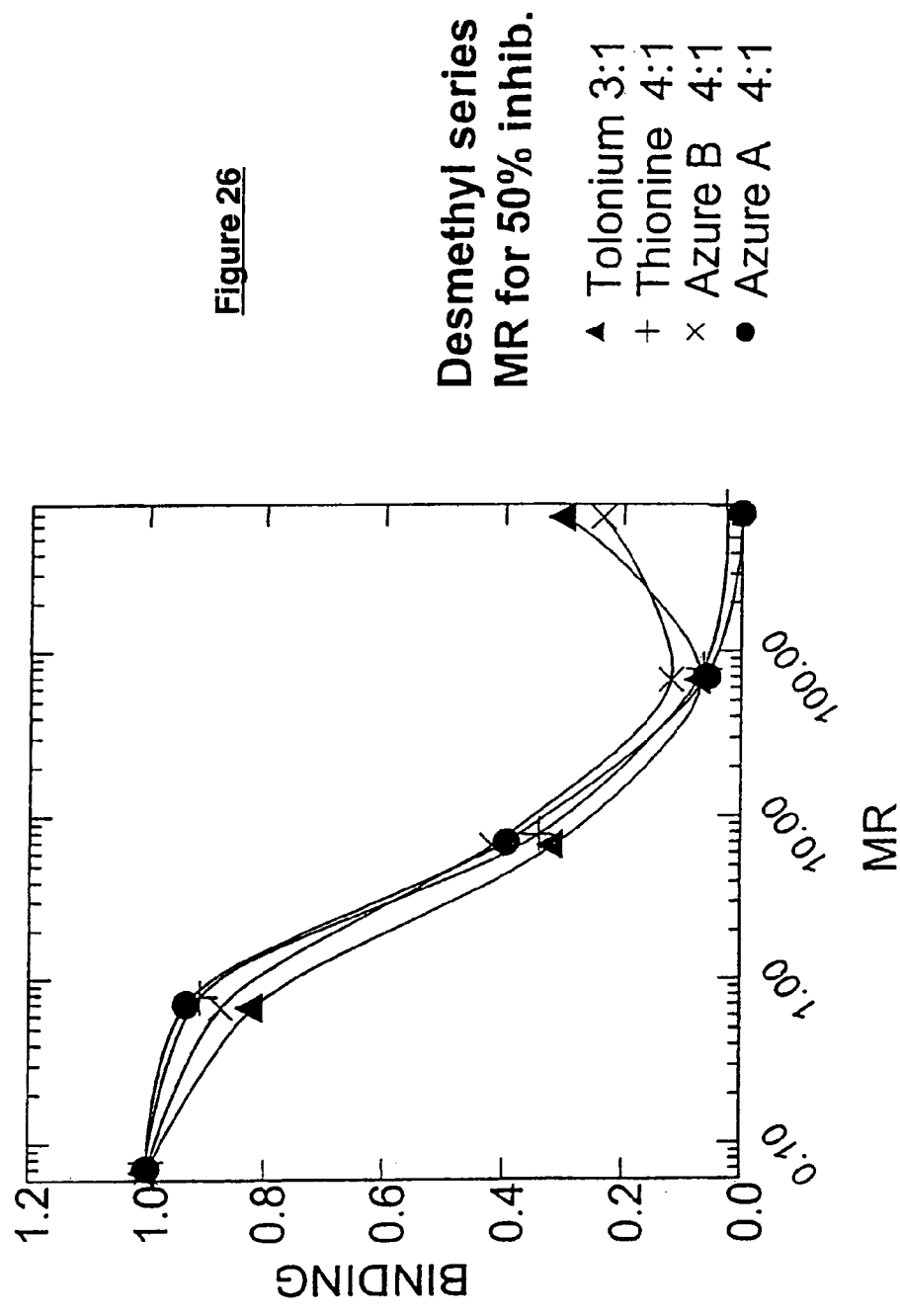
Figure 27:
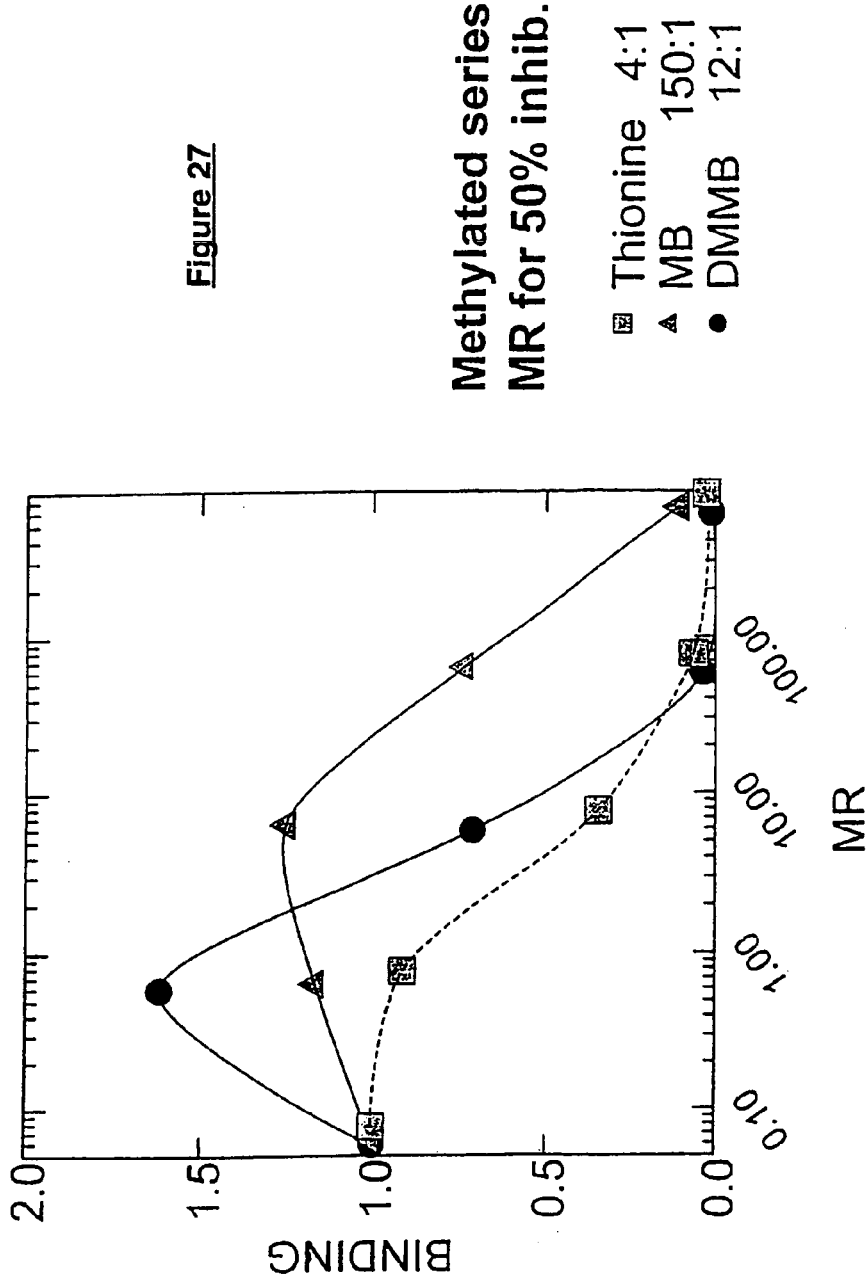

FIGS. 26 and 27 show the inhibitory effect on tau-tau binding of phenothiazines having 0, 2, 3 or 0, 4, 6 methyl groups, respectively.

Figure 28:
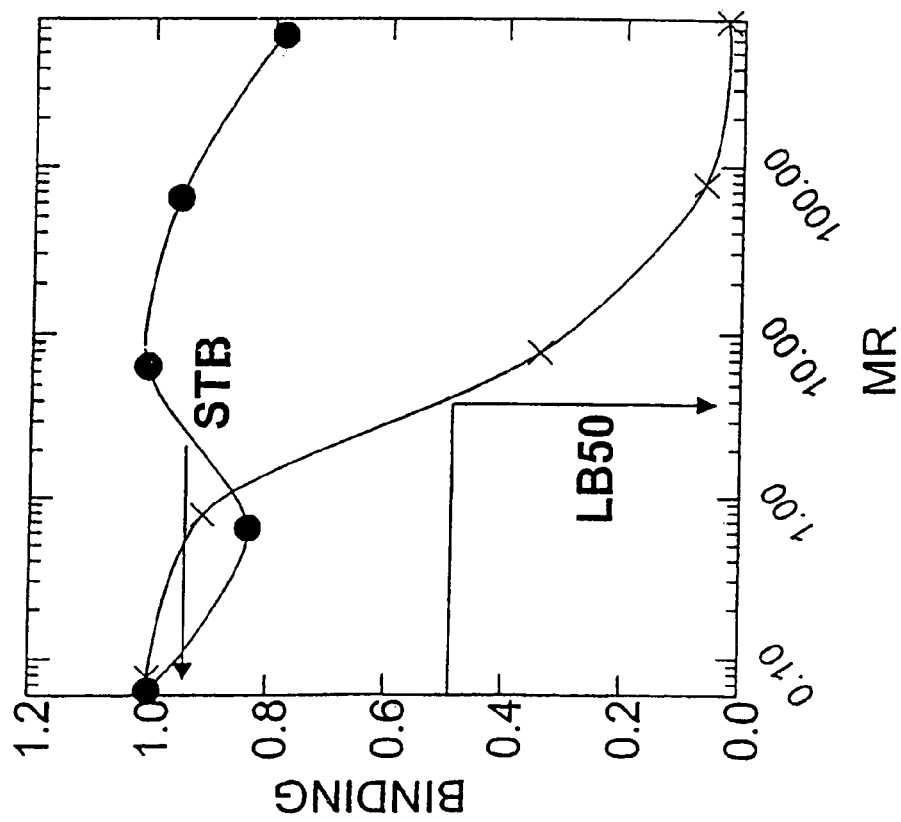

FIG. 28 shows the derivation of two parameters useful for measuring the inhibition of tau-tau association by test compounds. STB is the standardised binding relative to that seen in the absence of compound, taken as the mean observed at 1 and 10 μg/ml. As described in WO 96/30766, an STB value of 1.0 represents binding equivalent to that observed in the absence of compound, whereas a value of 0.2 indicates that the binding was reduced to a mean of 20% at test compound concentrations of 1 and 10 μg/ml. LB50 is log 10 molar ratio of compound:tau producing 50% tau-tau binding compared with that seen in the absence of compound (B50).

Figure 29:
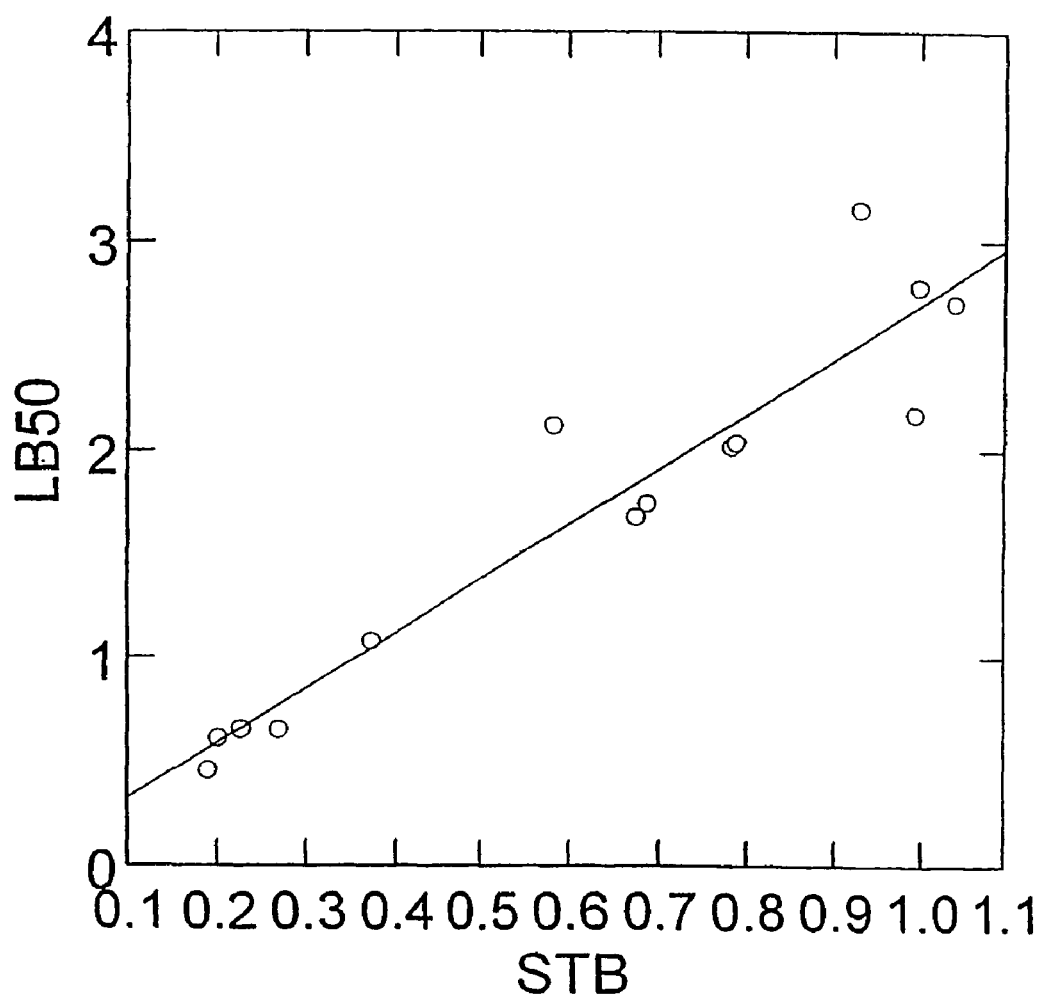

FIG. 29 shows the relationship between STB and LB50 parameters. STB can be shown to be a linear function of the LB50.

STB is a logarithmic function of the molar ratio of compound:tau at which tau-tau binding is reduced by 50%.

LB50 is the log of the molar ratio of compound with respect to tau at which tau-tau binding is 50% of that observed in the absence of compound $$LB50 = 0.05 + (2.65 \times STB) \quad r = 0.95$$

The determination of in vitro B50 requires that there be some degree of inhibition of tau-tau binding, and a 50% value is obtained by extrapolation. Determination of STB requires no such extrapolation procedure.

FIG. 30 shows compounds for which both STB and B50 values have been determined. Assuming that the total tau concentration in cells is approximately 500 nM (i.e. the concentration of tau used in the assay), the B50 values provide an approximation in the in vitro assay to the concentration (i.e. [500×B50] nM) at which the activity might be expected in cell systems.

Figure 31:
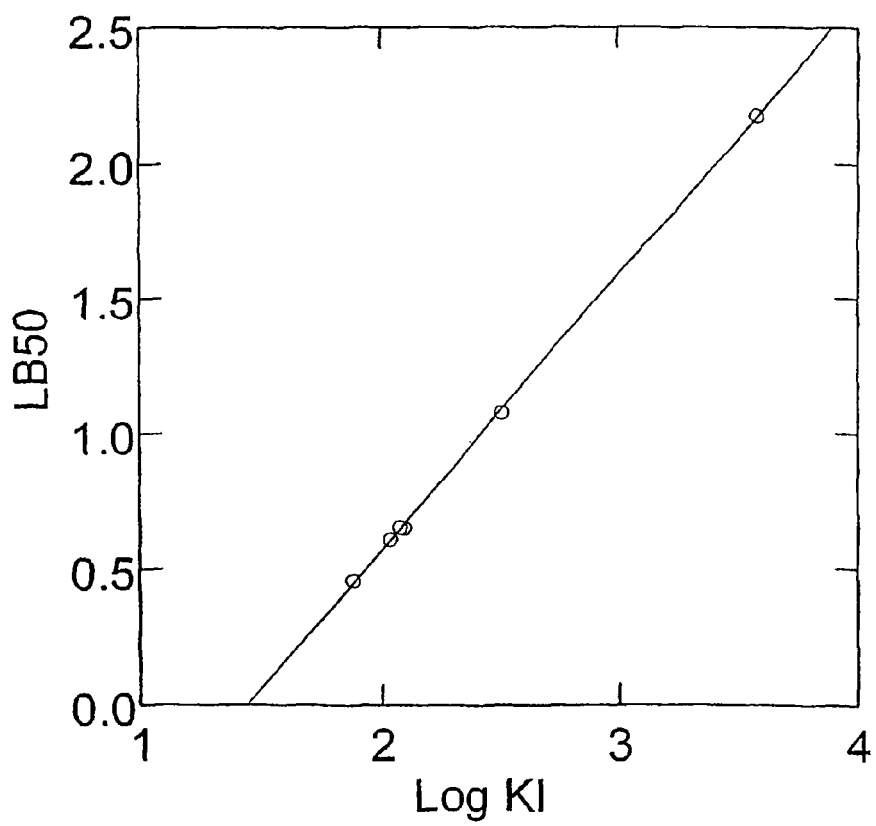

FIG. 31 shows the formal relationship between the in vitro LB50 value and the log KI value for the diaminophenothiazine series.

Figure 32:
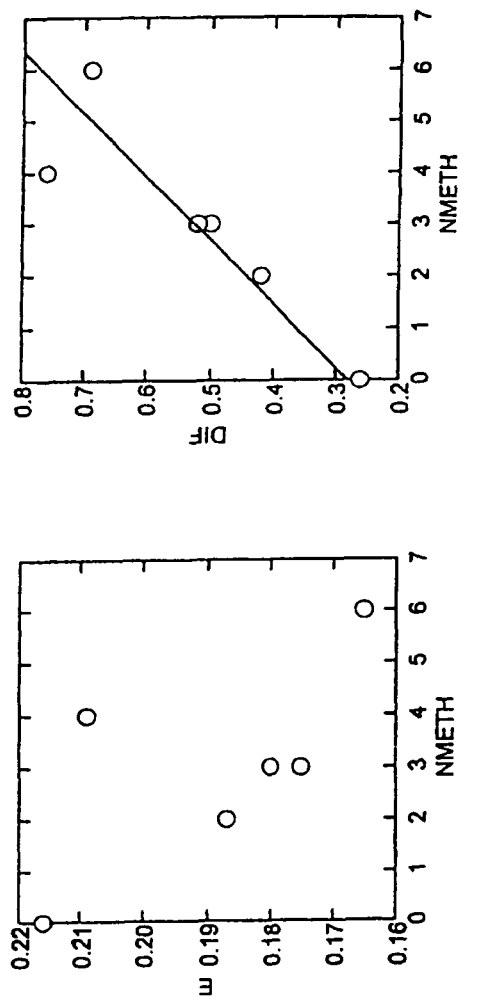

FIG. 32 shows the relationship between the number of methyl groups in a diaminophenothiazine (NMETH) and the redox potential (E) and diffusion coefficient (DIF). Italicised figures indicate correlation coefficients (R) and p values after exclusion of MB.

Figure 33:
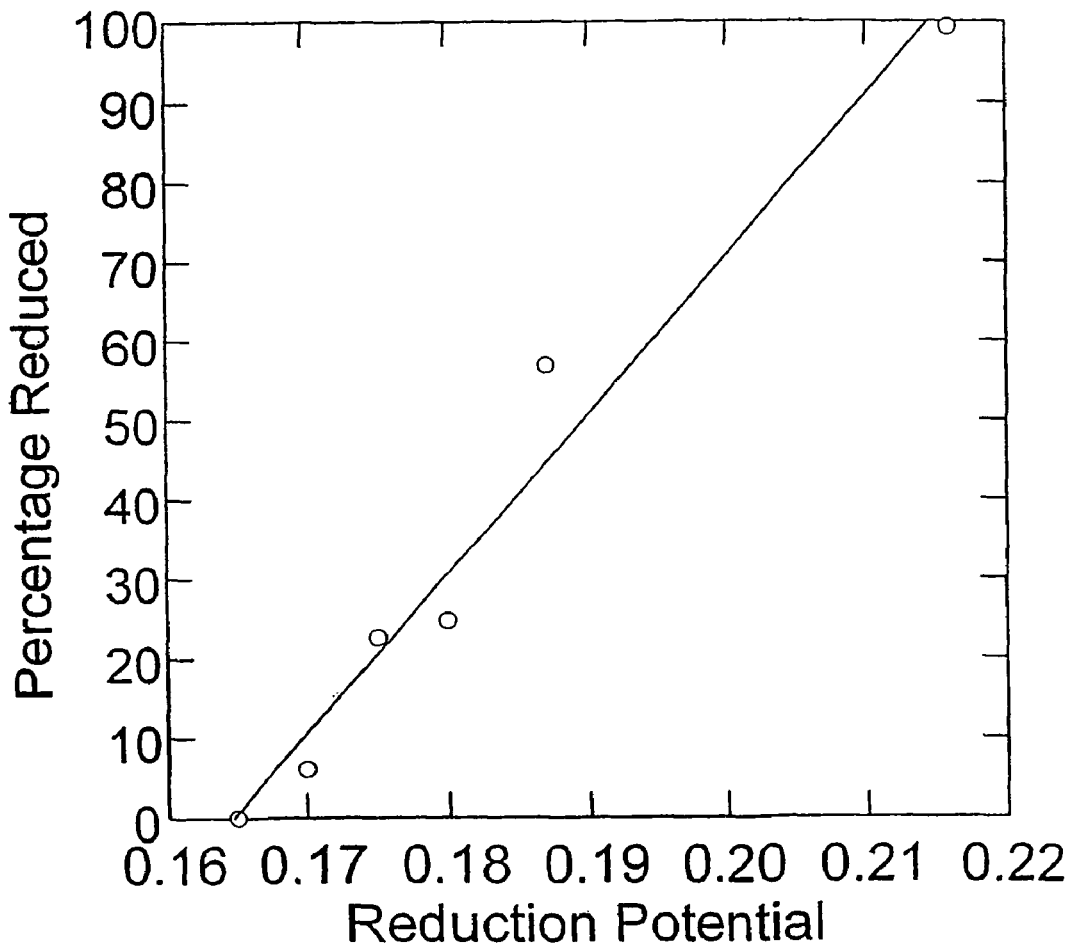

FIG. 33 shows the relationship between the percentage of compound that is reduced, as determined experimentally, and the known reduction potential of the compound. The reduction potential predicts the observed extent of reduction of the diaminophenothiazines.

Figure 34A:
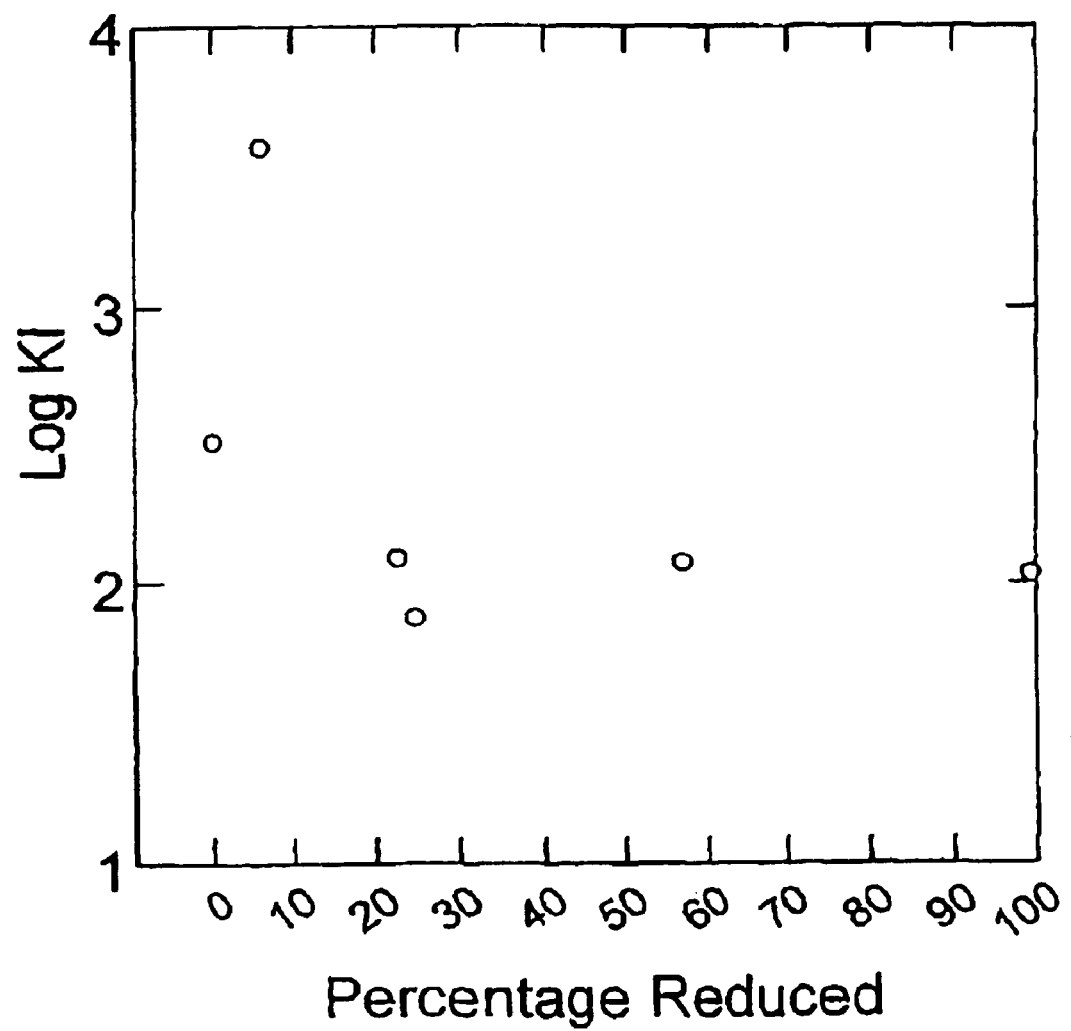
Figure 34B:
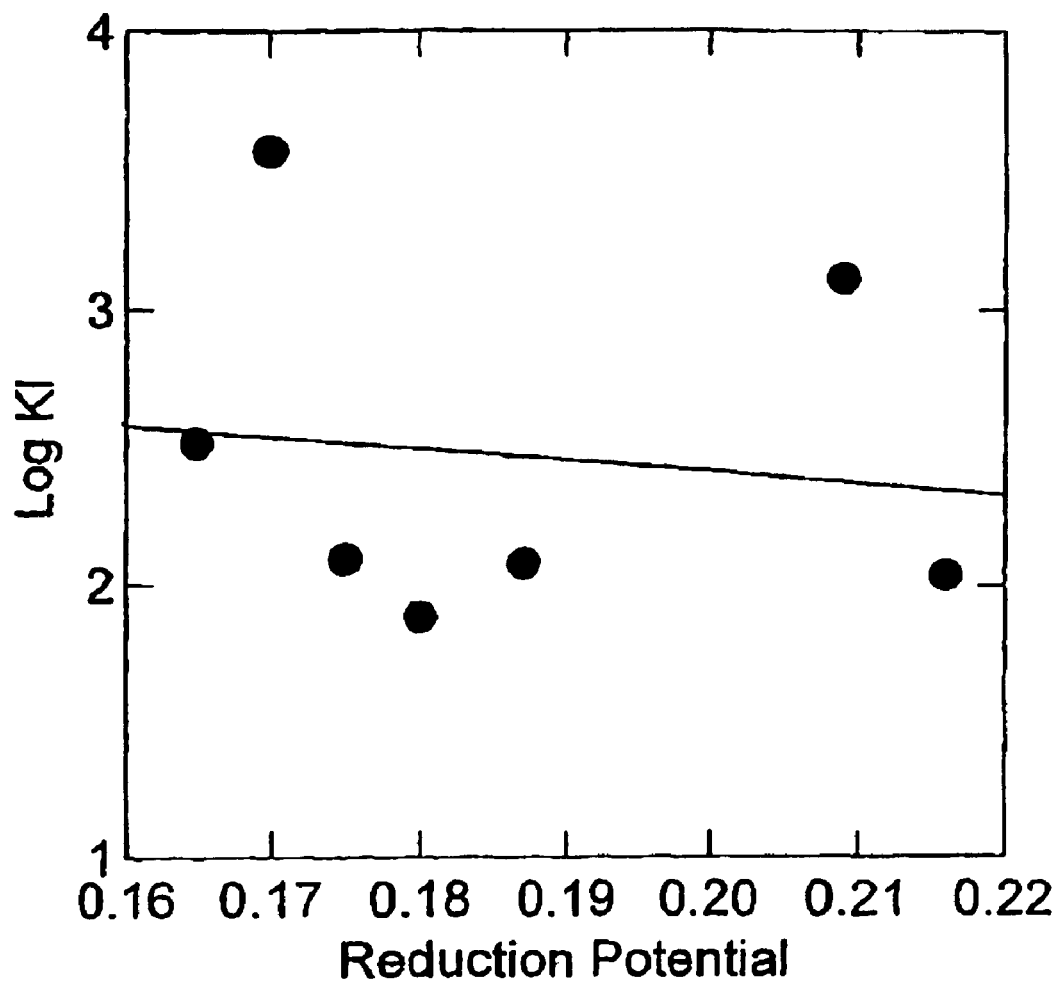

FIG. 34a shows that there is no clear relationship between inhibitory potency and the extent of reduction of compounds. FIG. 34b shows that inhibitory potency is not determined simply by reduction potential.

Figure 35:
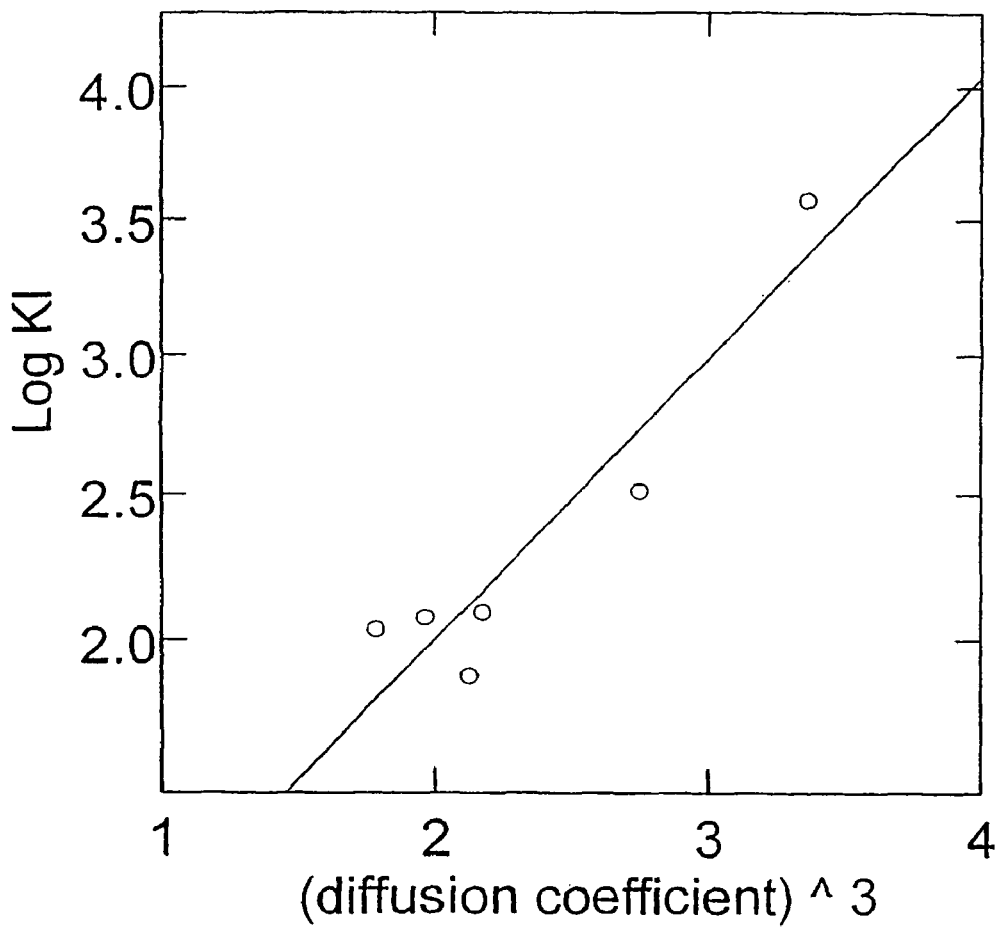

FIG. 35 shows that the inhibitory potency can be related directly to the diffusion coefficient (which is a measure of the tendency of the reduced form to stack and aggregate).

Figure 36:
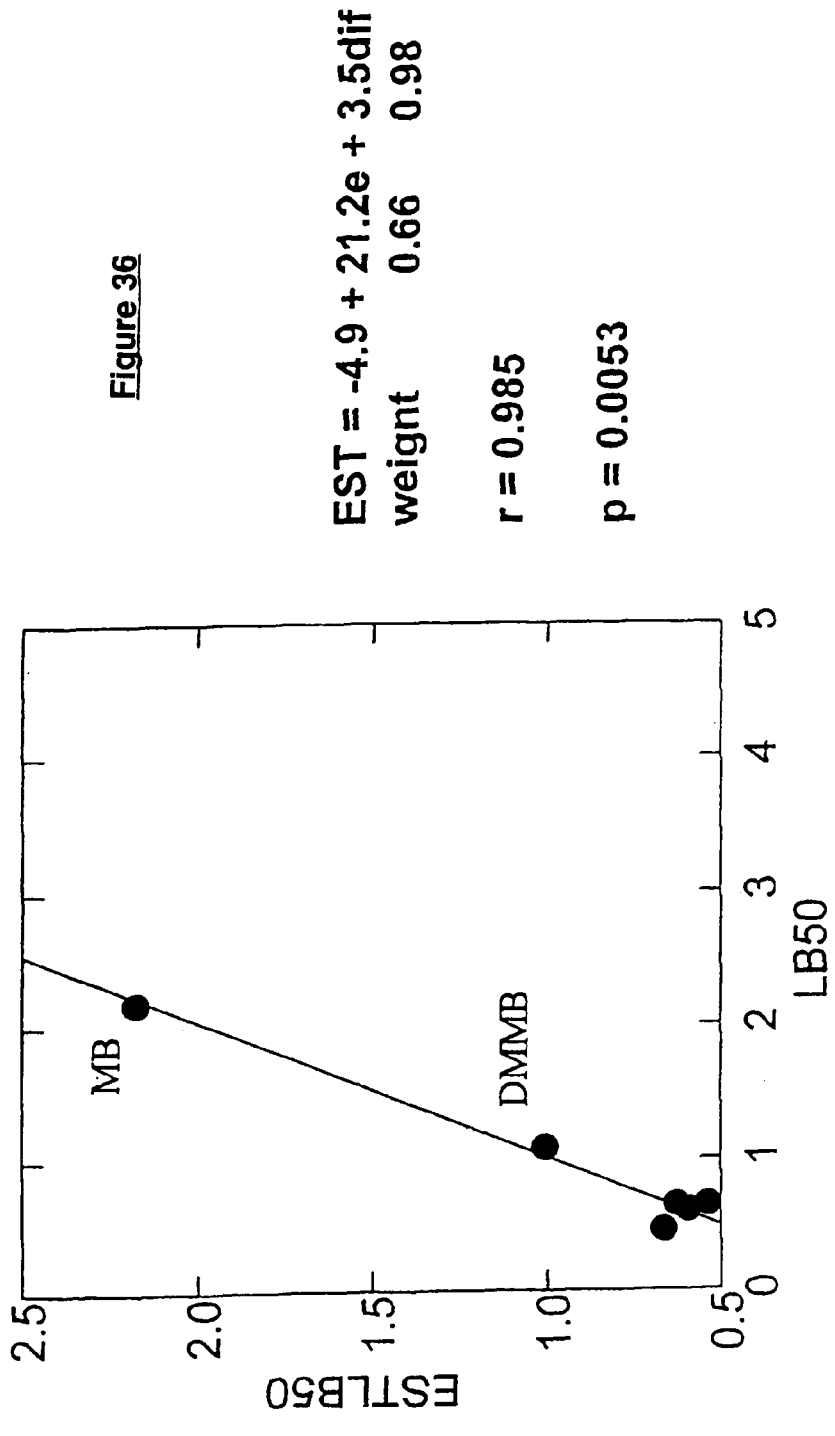
Figure 37:
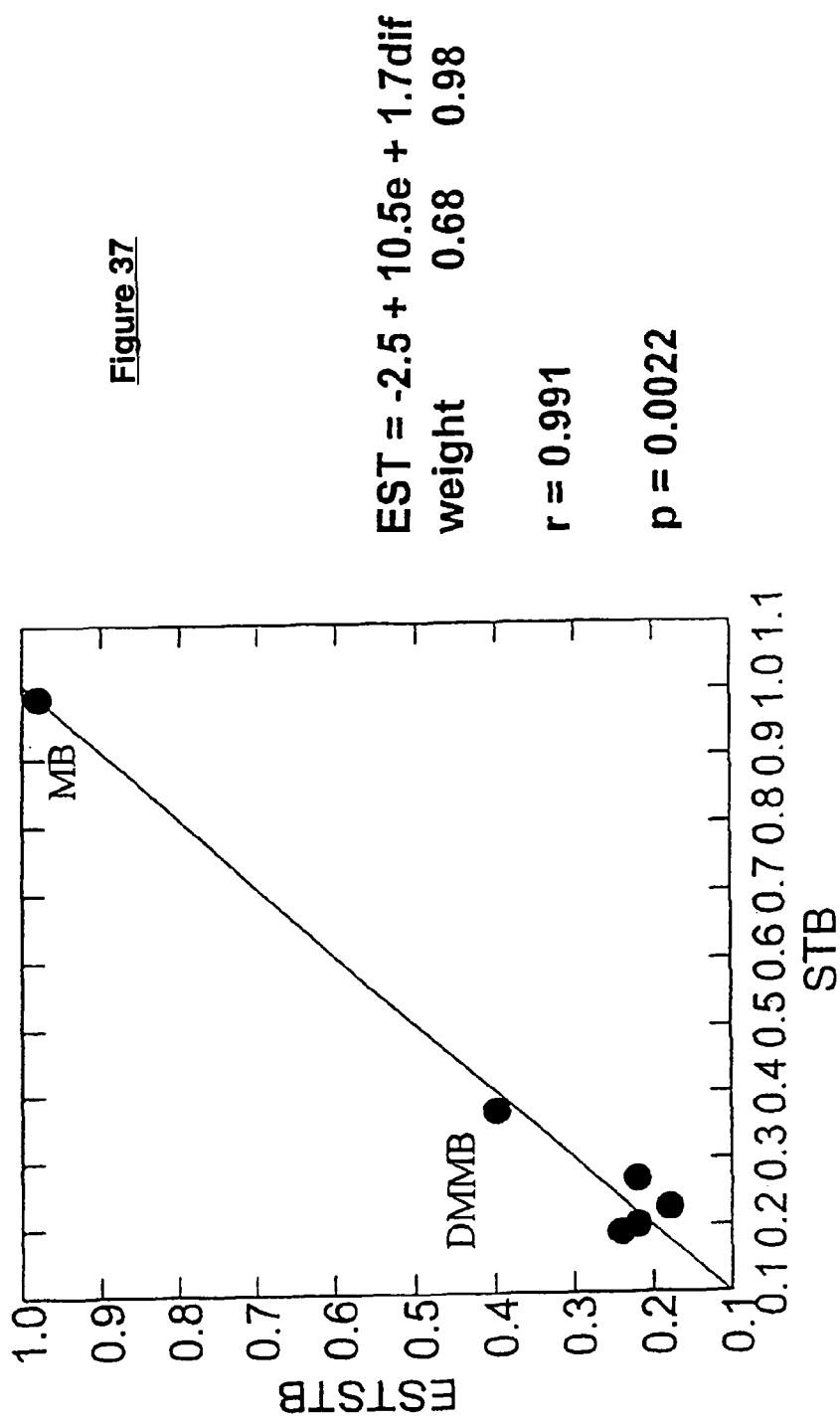

FIGS. 36 and 37 show the predicted relationships between estimated LB50 ("ESTLB50") and STB ("ESTSTB") values, respectively, and reduction potential and diffusion coefficient, in which the diffusion coefficient is given the greater weighting.

Figure 38:
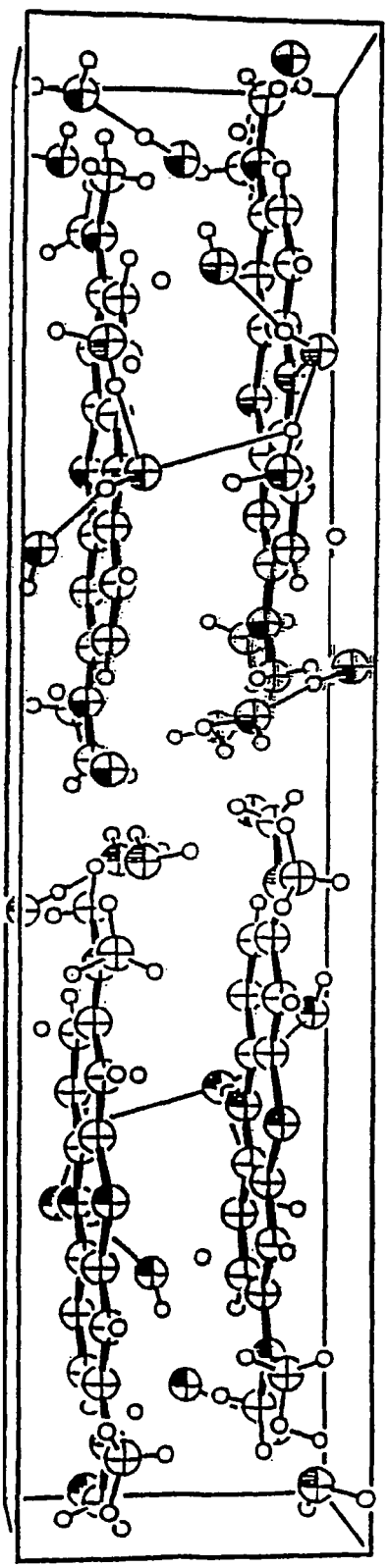

FIG. 38 shows the crystalline structure of Methylene Blue.

Figure 39:
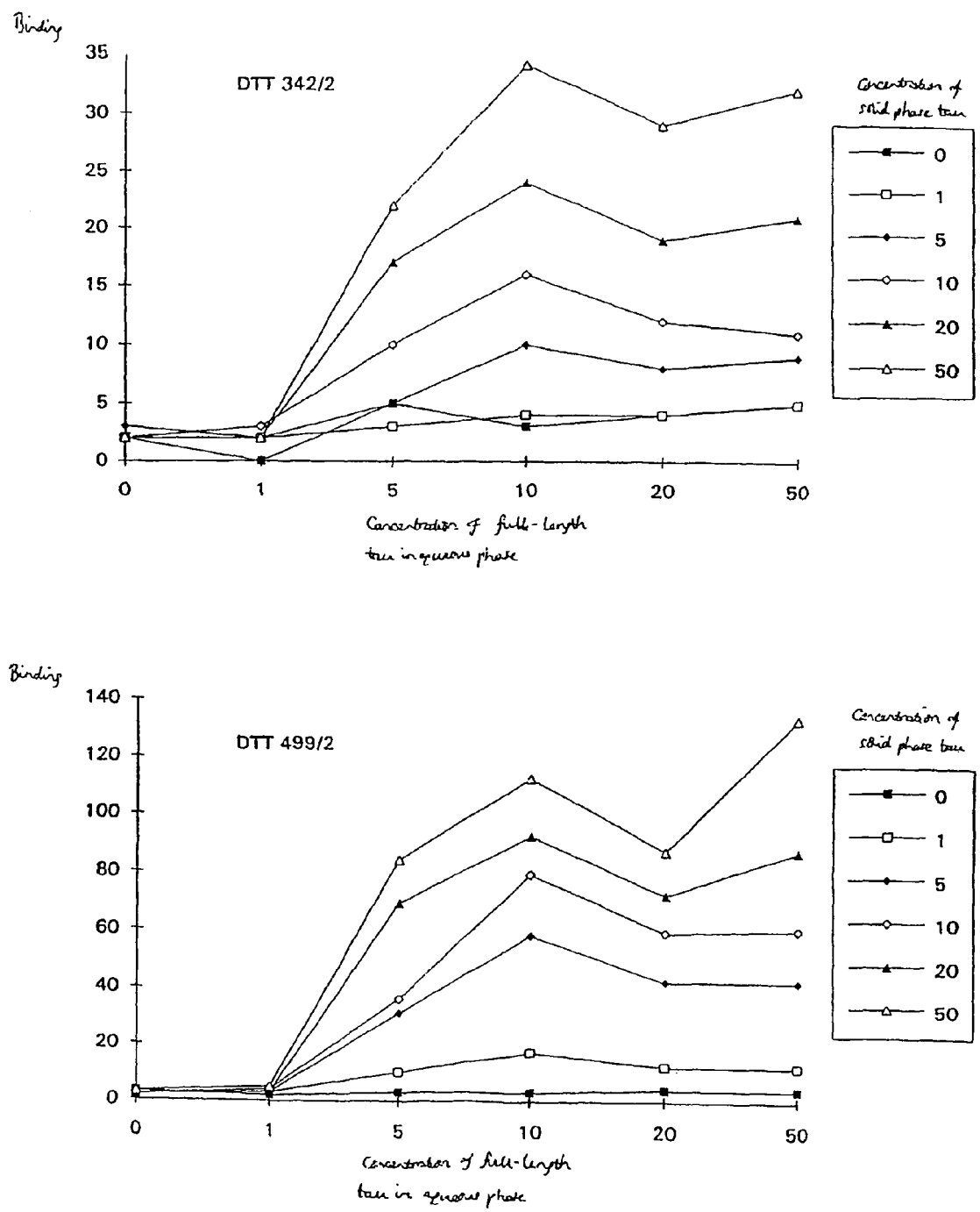

FIG. 39 shows tau-tau binding in the presence of 1 mM DTT, as measured in the solid phase assay of WO 96/30766. Two different antibodies were used to detect tau-tau binding, namely mAb 342 (top) and 499 (bottom). The vertical axis represents tau-tau binding, the horizontal axis shows the concentration of full-length tau in the aqueous phase, and the key shows varying concentrations of solid-phase tau. As can be seen, tau-tau binding still occurs in the presence of DTT.

Figure 40:
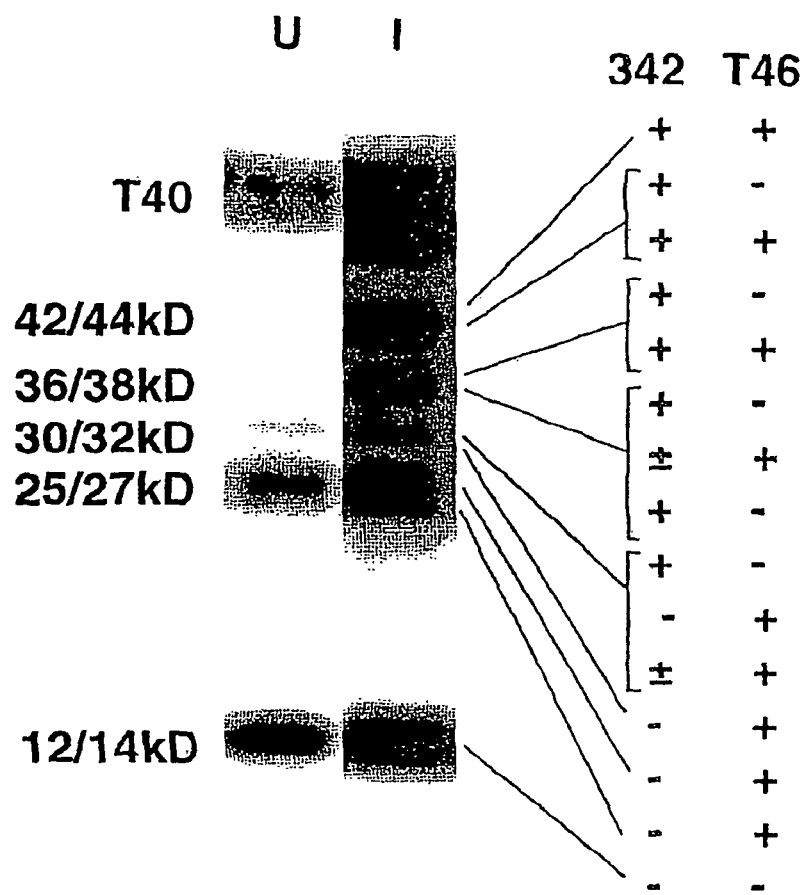

FIG. 40 shows various species of tau fragments and doublets which are present without induction ("U") and following induction ("I") in a cell line of the present invention. These include species with mobilities equivalent to 12/14 kD, ~25/27 kD, ~30/32 kD, ~36/38 kD and ~42/44 kD (see Example 3).

FIG. 41(a) shows how the 12 kD fragment arises via template-induced proteolytic processing of full-length tau molecules at the approximate positions shown by the arrowheads.

FIG. 41(b) shows how the 25/27 kD species arises via template-induced proteolytic processing of full-length tau molecules at the approximate positions shown by the arrowheads.

Figure 41:
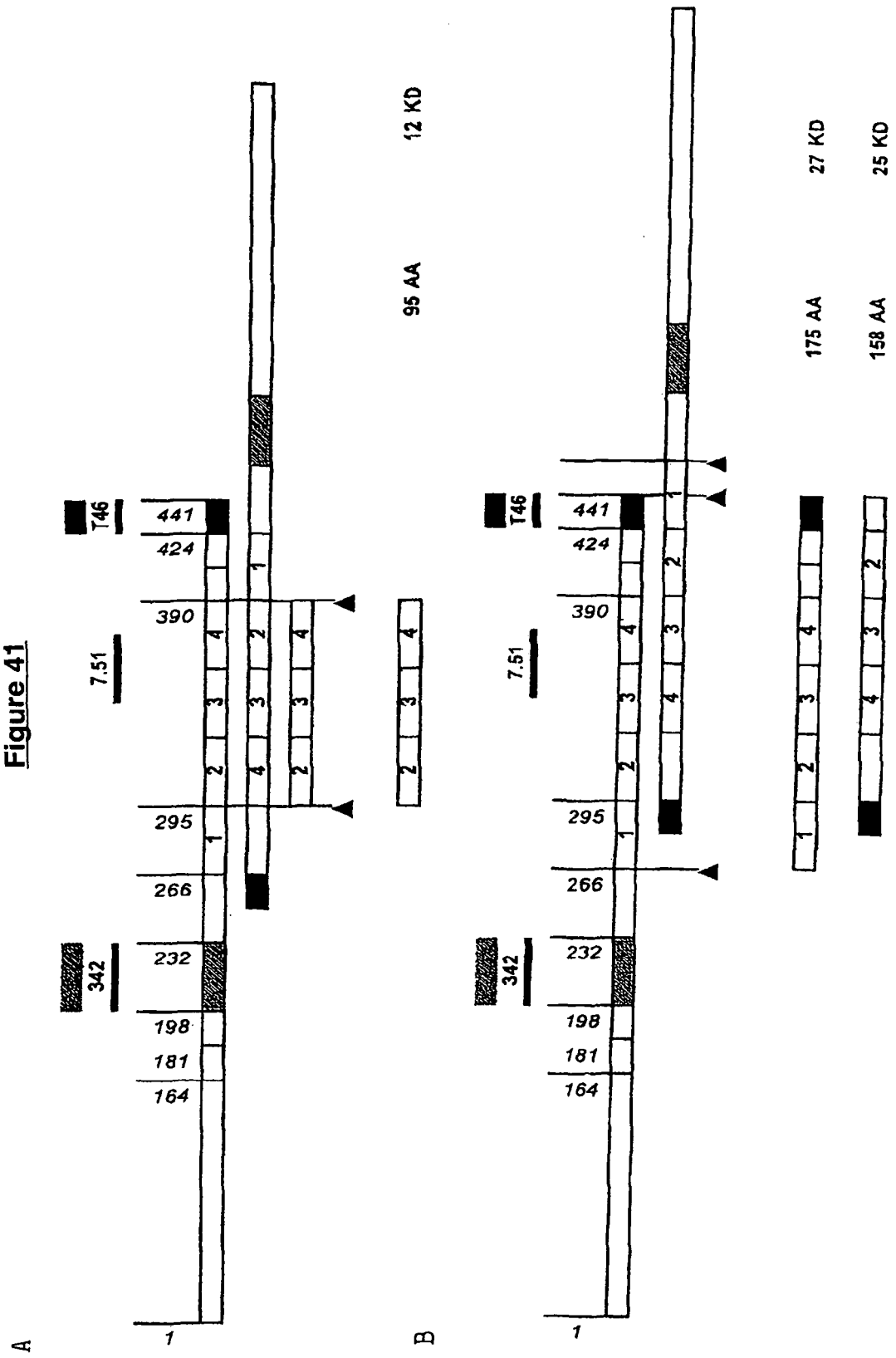
Figure 42:
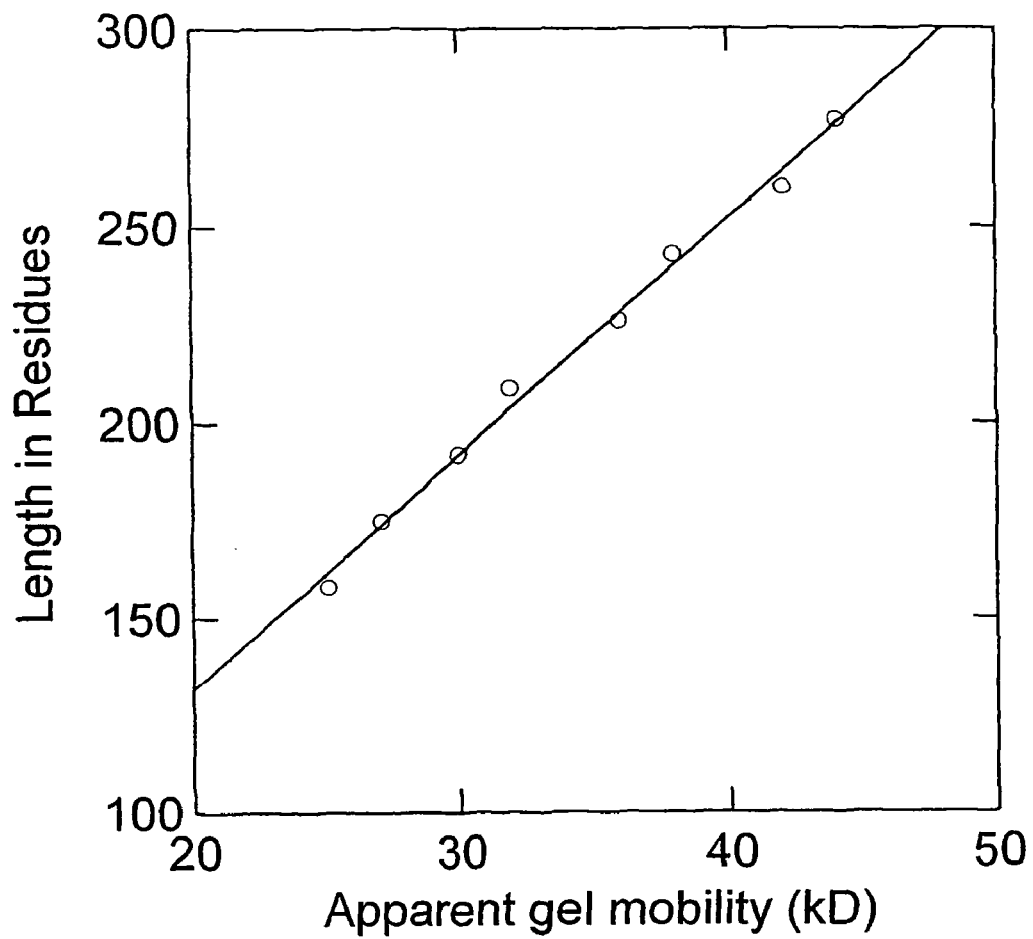

FIG. 42 shows a plot of the apparent gel mobilities of the species of FIGS. 40-41 and their lengths in amino-acid residues.

Figure 43:
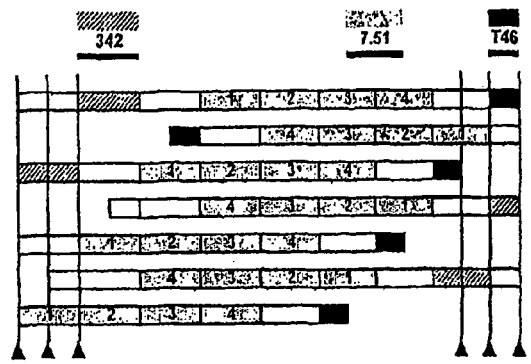

FIG. 43 shows the fragments of FIGS. 40-42 are at intervals of either ~34 residues or ~17 residues which is the equivalent of a single tau repeat, or half of it. All of the fragments may be generated from a basic heptameric aggregate as a simple set of proteolytic cleavages occurring at the positions indicated by the arrowheads.

FIG. 44 shows these same fragments in descending order of length and increasing gel mobility.

Figure 45:
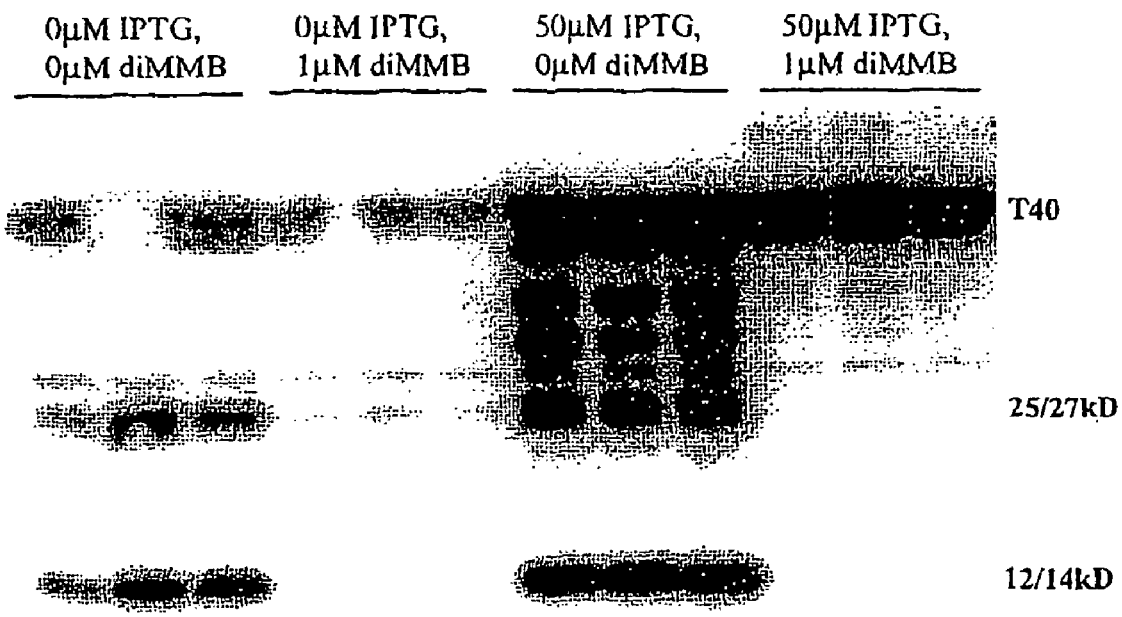

FIG. 45 shows that DMMB is surprisingly potent in the cell model. Its inhibitory activity could be seen both in the absence of IPTG induction and following induction (see Example 4).

Figure 46:
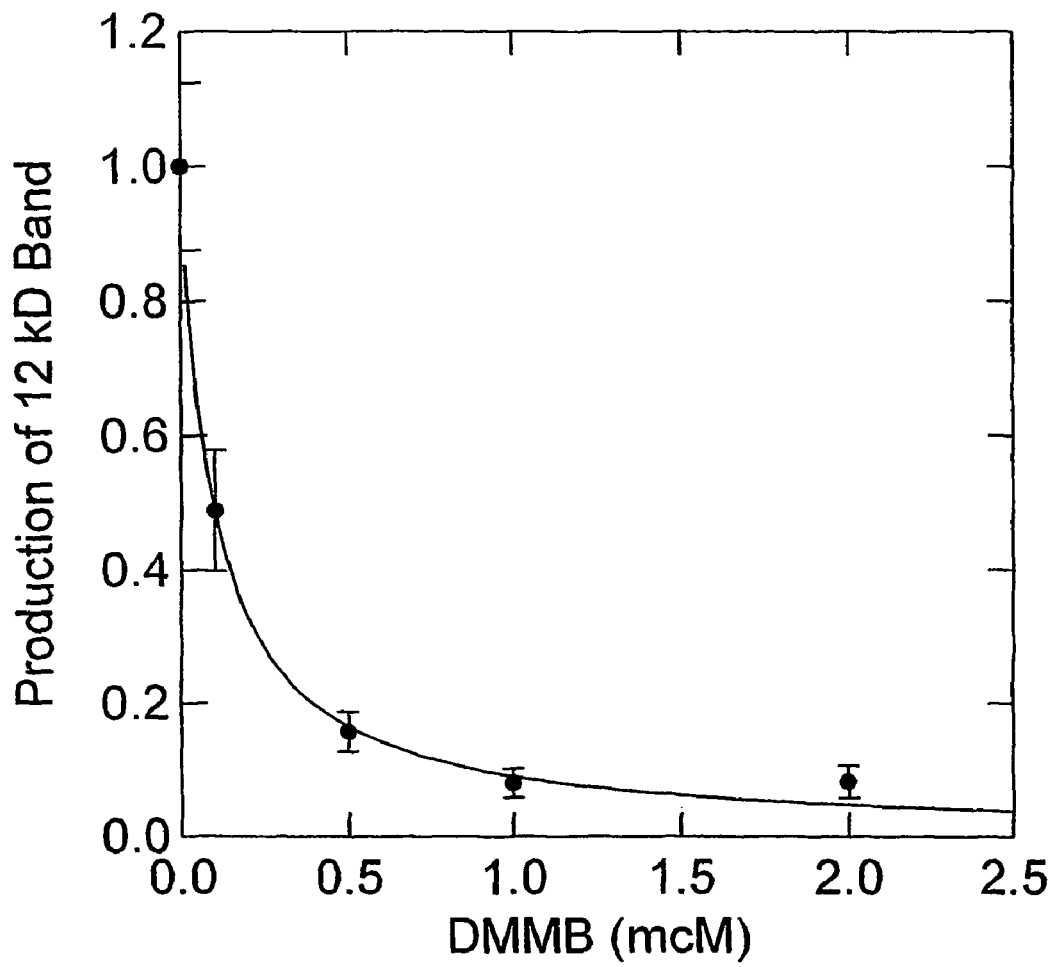

FIG. 46 shows the activity of DMMB on base-line expression of the 12/14 kD species, using the same set of assumptions regarding intracellular tau concentration and in vitro tau-tau binding affinity used in FIGS. 10-16.

insert. The use of a single restriction site for the cloning means that T40 can insert into the vector in either orientation. The orientation of the inserts was determined so as to select colonies with the vector containing T40 in the correct orientation for expression.

```
Primers used
5'-3' T40-Not I (SEQ ID NO: 3)
                                      start
5'-gtc gac tct aga ggc ggc cgc ATG GCT GAG CCC CGG CAG GAG-3'
                         Not I 3'-5' T40-Not I (SEQ ID NO: 4)
                                      stop
5'-act ctt aag ggt c
gc ggc cgc TCA CAA CAA ACC CTG CTT GGC CAG -3'
            Not I
```

Cellular activity is predicted via standard inhibition model:

activity=[tau]/([tau]$Kd^*$(1+[DMMB]/$Ki$))

DMMB has an apparent KI within the cell of 4.4 nM, and the cellular B50 value is ~100 nM.

EXAMPLES

General Materials and Methods

Production of 3T6H Cell Lines

3T6 cells were ECACC No: 86120801 Mouse Swiss Albino Embryo Fibroblasts.

For the inducible system, the experiments employed Lac Switch™ from Stratagene using the p3'SS vector to express the Lac repressor protein and pOPRSVICAT to express the full-length tau under the control of the Lac repressor. Expression is induced by the addition of IPTG.

Initially 3T6 cells were transfected, by electroporation, with the p3'SS plasmid and colonies selected by hygromycin resistance. 5 clones that were expressing varying levels of the Lac repressor protein (determined by immunocytochemistry) were picked, and also the non-cloned cells were retained for comparison.

Production of pOPRSVT40 Vector

The T40 insert for cloning into the pOPRSVICAT vector was prepared by PCR with Vent polymerase (NEB) using primers (shown below) that included a Not I site and a start or stop codon as appropriate. The PCR product and pOPRS-VICAT vector were cut with Not I and purified. The vector was dephosphorylated to prevent re-ligation, and the insert ligated into the vector using standard protocols.

The resulting ligation mix was transfected into competent E. coli cells and the cells plated out on amp plates. Colonies were picked and gridded out on a new amp plate. Colony lifts were taken to Hybond-N 0.45 μm nylon membrane (Amersham) and possible positives selected by colony hybridisation using dGA labelled with ($\alpha$-$^{32}$P) dCTP (Amersham) (using an oligolabelling kit (Pharmacia Biotech) and purified on a Nap-10 column (Pharmacia Biotech)). Hybridisation was carried out at 65° C. overnight in Church buffer followed by 2×20 mins washes in Church wash. Positive colonies, labeled with radioactive probe, were detected by exposing the blots to x-ray film overnight at −70° C.

Positive colonies were selected and grown, then checked by PCR and restriction digest to confirm the presence of the insert.

Sequence complementary to T40 sequence is shown in capitals, the start and stop codons are marked. The Not I site to be added is shown underlined. The remaining sequence shown in lower case is a 13 base pair overhang to allow the Not I enzyme to cut efficiently. This was complementary to sequence in the hTau40 plasmid vector to allow efficient binding of the primers.

Determination of Insert Orientation

Orientation was determined using a restriction enzyme that cuts the insert once and the vector at most a few times, and that gives a differing restriction digest pattern for each orientation. Hind III fits these criteria for pOPRSVT40. If the insert is absent two restriction bands are produced. If the insert is present three bands are produced and the size of the bands depends on the orientation of the insert as shown below.

| Forward (correct) Orientation | 5385 bp | 1030 bp | 381 bp |
| Reverse Orientation | 6101 bp | 381 bp | 314 bp |

Production of Cells Expressing T40 Under the Control of an Inducible Promoter

The pOPRSVT40 plasmid was produced and purified by CsCl gradient centrifugation. This was transfected (by electroporation) into 3T6H cells (expressing the Lac repressor protein) produced as described above. Positive cells were selected for by resistance to G418 (at 500 μg/ml). Resistant colonies were picked and grown on. The level of expression of full-length T40 with and without the addition of IPTG was determined with anti-tau antibodies by both immunocytochemistry and Western blot.

Production of pZeo295-391

The plasmid pZeo295-391 was designed to express protein corresponding to the truncated fragment of tau (residues 295-391; see below). A constitutive system (pcDNA3.1 from InVitrogen, Netherlands) was used—the plasmid imparts resistance to the antibiotic zeocin. The cDNA for this region was amplified by polymerase chain reaction (PCR), using specific oligonucleotide primers (sense and antisense; see below). The sense primer contained an EcoRI site and the antisense, a BamHI site. The fragments were subcloned into pcDNA3.1 (−)zeo (Invitrogen, Netherlands) that had been digested with EcoRI and BamHI. The inserted DNA is downstream from a cytomegalovirus promoter sequence and upstream of a polyadenylation signal. The plasmid contains the DNA sequence for the expression of ampicillin and zeocin resistance for selection in bacteria and eukaryotic cells, respectively. The authenticity of the inserted DNA was confirmed by full-length sequencing of both strands.

Nucleotide and Amino Acid Sequence for Truncated Tau Fragment 295-391

(SEQ ID NO: 5)
```
gataatatcaaacacgtcccgggaggcg-
gcagtgtgcaaatagtctacaaaccagttgacctgagca
aggtgacctccaagtgtggctcattaggcaa catccatcataaaccaggaggtggccag-
gtggaagtaaaatctgagaagcttgacttcaaggacaga
gtccagtcgaagattgggtccctggacaatat cacccacgtccctggcggag-
gaaataaaaagattgaaacccacaagctgaccttccgcgagaacgcc
aaagccaagacagaccacggggcggag
```

(SEQ ID NO: 6)
```
DNIKHVPGGGSVQIVYKPVDL-
SKVTSKCGSLGNIHHKPGGGQVEVKSEKLDFKDRVQSKIGSLDNIT
HVPGGGNKKIETHKLTFRENAKAKTDHGAE
```

295 sense primer (SEQ ID NO: 7)
```
                    met asp295
5' - CGG AAT TCC ACC ATG GAT AAT ATC AAA CAC GTC CCG - 3'
        EcoRI
```

391 antisense primer (SEQ ID NO: 8)
```
                    stop glu391
5' - C GCG GGA TCC TCA CTC CGC CCC GTG GTC TGT CTT GGC - 3'
            BamHI
```

The start and stop codons are in bold and the EcoRI and BamHI restriction sites to be added are underlined.

Tissue Culture of Cells for Assay

The medium used was DMEM (with Glutamax I, pyruvate, 4.5 g/l glucose) from Life Technologies, Scotland. This was supplemented with 10% FCS (Helena BioSciences), 50 U/ml penicillin, 50 µg/ml streptomycin, plsu further antibiotic as appropriate for the selection and maintenance of the relevant plasmid. Antibiotic concentrations were 200 µg/ml hygromycin (p3'SS selection and maintenance), 500 µg/ml G418 (pO-PRSVT40 selection and maintenance), 400 or 200 µg/ml zeocin (pZeo295-391 selection or maintenance).

Cells are grown at 37° C., in a humidified atmosphere of 5% $CO_2$. Cells are maintained in 10 cm dishes, and split when they approach confluency. Medium is removed, cells washed with PBS and cells released by trypsinisation with 1 ml of trypsin/EDTA solution/10 cm dish. Cells are resuspended in fresh medium at 1:10 dilution, or optionally in a range of dilutions from 1:5 to 1:20 (approximately 5000 to 20000 cells/$cm^2$).

For the testing of drugs, cells are plated in 6 well or 24 well plates at an initial density that will allow them to grow to 50-80% confluency within 24 hours. Drugs are added to the well at various concentrations, expression of full-length tau is induced by the addition of IPTG at 0-50 µM. Cells are grown for a further 24 hours and then collected for analysis by SDS PAGE/Western blotting.

Preparation of Tau Protein

Recombinant tau (clone htau40) and perchloric acid-soluble tau extracted from rat and human brain were prepared as described previously (Goedert, M. & Jakes, R. (1990) *EMBO J.* 9:4225; Goedert, M. et al (1993) *Proc. Natl. Acad. Sci. USA* 90:5066).

Gel Electrophoresis and Blotting

Cells grown as outlined above are washed once with PBS then lysed in 50 µl (24 well plates) or 100 µl (6 well plates) laemli buffer. Samples are stored at −20° C., boiled for 4 mins prior to running on 15% acrylamide gels using the BioRad miniProtean III mini gel system. Protein is transferred to PVDF membrane by Western blotting using the CAPs buffer system. The membranes are incubated in block buffer (5% non-fat milk powder (Marvel), 0.1% Tween 20 in PBS) for 1 hr to overnight. Tau protein is detected by incubating the membranes with mAb 7.51 diluted 1:5 with block buffer for 1-3 hrs or overnight, washing well with PBS/0.1% Tween20, incubating with anti-mouse HRP 1:5000 dilution in block buffer for 1 hr, and washing well with PBS/0.1% Tween20. Bound antibody is detected by ECL reaction detected on ECL hyperfilm (Amersham).

Blots are scanned into a computer on a Hewlett Packard Scanjet 6100C flatbed scanner at 600 dpi and saved as tiff files. Densitometry of the T40 and dGAE bands is performed with the Scananalysis program on an Apple Power Mac G3.

Drug Preparation

Thionine, methylene blue, DMMB, and tolonium chloride are all prepared as a 1 mM stock in ddH2O. Prior to use a 100 µM dilute stock is prepared in HBSS which is added directly to the medium on cells.

For oxidised drug this is prepared simply by diluting the 1 mM stock in HBSS and filter sterilising.

For reduced drug the 1 mM is treated with ascorbic acid and DTT to yield 0.5 mM drug, 50 mM ascorbic acid 50 mM DTT, this is allowed to stand for 15 mins (turns blue to colourless) before making the dilute stock. This is diluted in HBSS to yield 100 µM drug, 10 mM ascorbic acid, 10 mM DTT and filter sterilised. Cells are treated with the drug at various concentrations, but for the reduced drug the ascorbic acid and DTT concentrations are maintained at 400 µM throughout by using appropriate quantities of 100 μM reduced stock, 100 μM oxidised stock and 10 mM ascorbic acid/DTT stock.

SDS Gel Electrophoresis and Immunoblotting

Standard electrophoresis and immunoblotting procedures were used as described previously (Wischik, C. M. et al. (1988) *Proc. Natl. Acad. Sci. USA* 85:4506; Novak, M., et al. (1993) *EMBO J.* 12:365; Jakes, R. et al. (1991) *EMBO J.* 10:2725). Immunoblots were developed with the ABC kit (Vector Laboratories). The monoclonal antibodies (mAbs) 7.51, 21.D10, 499 and 342 were used as undiluted hybridoma culture supernatant fluids. mAb AT8 (Innogenetics, Belgium) was used at 1/1000 dilution. Anti-tau mAbs 7.51 (which recognises an epitope in the last repeat; see Novak, M. et al. (1991) *Proc. Natl. Acad. Sci. USA* 88: 5837), 423 (which recognises tau C-terminally truncated at residue Glu-391; see Wischik, C. M. et al. (1988) *Proc. Natl. Acad. Sci. USA* 85:4506; Novak, M. et al. (1993) *EMBO J.* 12:365), 499 (which recognises a human-specific tau segment between residues Gly-14 and Gln-26; see Wischik, C. M. et al. (1996) *Proc. Natl. Acad. Sci. USA* 93:11213), and 342 (which recognises a segment between residues Ser-208 and Pro-251). mAb 21.D10 was raised against the A68-tau brain extract (Lee, V. M.-Y. et al. (1991) *Science* 251: 675).

Tau Binding Assay

This was carried out basically as described in Wischik, C. M., et al. (1996) *Proc. Natl. Acad. Sci. USA* 93:11213. Solid phase tau (0-20 μg/ml) was coated on 96-well poly(vinyl chloride) microtitre plates in 50 mM carbonate buffer at 37° C. for 1 h. The plate was washed twice with 0.05% Tween 20, then blocked with 2% Marvel in PBST for 1 h at 37° C. After washing again, the plate was incubated for 1 h at 37° C. with aqueous phase tau (0-300 μg/ml in PBST containing 1% gelatin). In the present application, 1 mM DTT was also added.

The plate was washed twice and incubated for 1 h at 37° C. with mAb 499 or 342, diluted with an equal volume of 2% Marvel in PBST. After washing, horseradish peroxidase-conjugated goat-anti-mouse antibody (1/1000 in PBST) was incubated for 1 h at 37° C. The plate was washed and incubated with substrate solution containing tetramethylbenzidine and $H_2O_2$ and the rate of change of absorbance measured using a $V_{max}$ plate reader (Molecular Diagnostics, California) as described previously (Harrington, C. R. et al. (1990) *J. Immunol. Meth.* 134:261). Each experiment was performed in triplicate and included controls in which both solid phase and aqueous phase tau were absent, and also with either one of the two absent.

Data Analysis

This was performed as described in Wischik et al. (supra) and curves were fitted according to the Langmuir equation with the Kaleidagraph (Synergy, Philadelphia) or Systat (SPSS Inc., Chicago) programs using quasi-Newton approximation. Curve-fitting correlation coefficients are given in the Figures.

Example 1

Constitutive Expression of Full-Length, Truncated and Mutated Tau

Expression of tau in eukaryotic cell lines was sought to generate a cellular model of tau aggregation under physiological conditions which did not suffer from the limitations of lipofectin-based approaches. This involves the expression of full-length tau and truncated tau fragments for both normal tau and tau carrying pathogenic mutations.

Full Length Tau

When normal full-length tau (T40) was transfected into cells (3T3 and NIE-115) it was expressed and involved in the assembly of the microtubule network within the cells.

Truncated Tau

Initially the cDNA for truncated tau fragment from the core of the PHF, corresponding to fragment 297-391, was transfected into non-neuronal 3T3 fibroblasts: this truncated tau was selected since it is: (i) present in the PHF-core; (ii) detected as deposits in AD brain tissue during the early stages of the disease; (iii) capable of supporting the catalytic capture and propagation of tau capture in vitro. Subsequently, a series of transfections was performed in which the extent of truncation at either N- or C-termini was varied, based partly on the immunochemical properties of the tau molecule. Six constructs were created with truncation at the N-terminus (186-441; 297-441) at the C- and N-termini (186-391; 297-391) and at the C-terminus (1-391). The pattern of immunoreactivity for the six constructs with a limited panel of antibodies was capable of discriminating all of the tau fragments generated in this way.

The constructs were expressed in eukaryotic cells both transiently (using pSG5 as the vector) and stably (using pIF2 and pZeo as vectors). Stable transfectants are selected on the basis of resistance to the antibiotics geneticin and zeocin for pIF2 and pZeo, respectively. Epitope analysis was performed on bacterially expressed proteins using pRK172 as the vector. FIG. 20 summarises the results for various fragments in 3T3 and COS-7 cells. Further results showed that the expression of two forms of tau in the same cell can affect the pattern of immunoreactivity. For example, stable expression of 1-391 and 295-391 results in the appearance of abnormal bundles within the cells. However, maintaining such cells in a stable and reproducible state proved elusive.

Mutated Tau

Mutagenesis of full-length tau was used to generate known clinical mutations. These were subcloned into pIF2 and stable transfectants generated in 3T3 and NIE cells for a number of mutations including those which affect microtubule assembly properties of tau (G272V, V337M, P301 S, R406W) and S305N, which affects the alternative splicing of the tau gene in vivo. In general, cells expressing full-length tau carrying mutations exhibited labelling of the microtubular network and was indistinguishable from cells transfected with wild-type tau. Cell lines expressing certain truncated tau fragments including mutations proved unstable.

Conclusion

In summary, the constitutive expression of truncated tau within eukaryotic cells proved difficult to achieve. Although transient transfection systems permitted the optimisation of expression of tau by manipulating the Kozak consensus surrounding the initiation codon for 297-tau, the expression of e.g. 297-391 was still modest, suggesting some inherent toxic properties of the fragment. Stable transfections reiterated this conclusion. This latter system demonstrated that truncation at either N- or C-termini resulted in a slightly greater propensity for the tau to assemble in amorphous deposits rather than in a microtubular network. Stable expression of combinations of tau fragments also generated aggregates within the cytoplasm of cells, but this system was not readily reproducible.

Example 2

Inducible Expression of Truncated Tau

In a further attempt to create a stable, reproducible system, without the toxicity associated with constitutive expression, inducible expression of the core-tau fragment of the PHF (i.e. 297-391—which is 12 kD) was attempted.

Several inducible systems for expression of proteins in eukaryotic cells were tried, although the preferred system was the "lac switch" system. In this system, two vectors are incorporated into cells, typically 3T3 or 3T6 fibroblasts which do not express any endogenous tau protein. The first, the p3'SS vector codes for constitutive expression of the lac I gene, and expressors are selected on the basis of hygromycin resistance. The second, pOPRSVICAT incorporates the DNA coding for the tau protein fragment under the control of a strong RSV promoter which contains operator sequences from the Lac operon. Cells which incorporate this vector are selected on the basis of neomycin resistance. Cells which have incorporated both vectors have the property that constitutive expression of lac I prevents expression of the incorporated protein (i.e. tau) controlled by the Lac operon. The addition of the sugar IPTG competes for the binding of lac I to the Lac operon, and so permits expression of tau protein.

Inducible expression of the 12 kD fragment was carried out in two cell lines. These did not show appreciable levels of tau protein expression until after 3 days treatment with IPTG at which stage high levels of 12 kD suddenly appeared, forming intracellular aggregates which promptly killed the cell. The process of aggregation was, as expected, non-linear progressing from low level expression to sudden accumulation of toxic aggregates without any clear gradation, making the aggregation and toxicity impossible to control. This non-linear progression prevented a proper control of the system.

Example 3

Expression of Tau in Stable Cell Lines According to Invention

In view of the results above, a further system was used as follows. Tissue culture cell line DH 19.4.1.4 and clones thereof were based on 3T6 cells (ECACC No: 86120801 Mouse Swiss Albino Embryo Fibroblasts) expressing full-length, four repeat human tau under the control of an inducible promoter and truncated human tau (295-391) under the control of a constitutive promoter.

Cells expressing T40 under the control of an inducible promoter, T40.22.10, were transfected (by lipofection) with the pZeo295-391 plasmid. Positive cells were selected for by resistance to zeocin at 400 µg/ml. Expression of truncated tau on a background of inducible expression of full-length tau was confirmed by Western blot analysis with Mab 7.51.

FIG. 21 illustrates the inducible expression of full-length human tau only in 3T6 fibroblasts in two cell lines. T40.22 shows low level background leakage of full length tau in the uninduced state ("U"), and high levels of expression after addition of IPTG (i.e. induced, "I"). T40.37 shows the same, but lower levels of expression without induction. FIG. 22 shows the results of a triple vector system. A vector permitting very low level constitutive expression of the 12 kD fragment was introduced into cell lines in which inducible expression of full length tau had already been achieved (T40.22 shown in FIG. 21). FIG. 22 shows what happens when low levels of IPTG are introduced to induce expression of full-length tau. At 0 µM IPTG, there is very low level expression of the 12 kD band, and low "background leakage" expression of full-length tau. As progressively more full-length tau is induced by introducing higher levels of IPTG, more of the full-length tau is converted to the 12 kD species, and more of the intermediate higher molecular weight fragments (described in more detail in FIGS. 43 and 44) are produced.

Examination of the original T40-inducible cell line (T40.22.10) which did not contain the vector for constitutive expression of the 12 kD fragment shows that the 12 kD species is not produced as a truncation by-product of full-length tau induction. Enhanced expression of the 12 kD band following induction of T40 was seen only in cells with low level prior expression of the 12 kD fragment (DH19.4.1.4.6). That is, pre-existing 12 kD provides a template for production of more 12 kD following the induction of full-length tau. An additional doublet may also appear with apparent gel mobility of ~25/27 kD when the cells are in the uninduced state (e.g. in the cell line designated DH 19.4.1.4A.B2). Following induction with IPTG, a further series of doublets may appear, with gel mobilities ~30/32 kD, ~36/38 kD and ~42/44 kD.

These species are shown in FIG. 40 both without induction ("U") and following induction ("I"). Also shown are the patterns of immunoreactivity of these fragments seen with mAb 342 and a C-terminal polyclonal antibody T46 which recognises epitopes located between residues Ser422 and Leu441.

The derivation of the fragments seen in the uninduced state (i.e. 12/14 kD and 25/27 kD) may be explained by reference to FIG. 41.

FIG. 41(a) shows how the 12 kD fragment arises via template-induced proteolytic processing of full-length tau molecules at the approximate positions shown by the arrowheads.

In the case of the 25/27 kD species, these fragments cannot represent dimers of the 12/14 kD species, as these fragments are immunoreactive with T46. Therefore, a further proteolytic product of the full-length aggregating tau protein must arise via cleavages occurring at the approximate positions shown by the arrowheads in FIG. 41(b).

Following induction (FIG. 40, I), the further series of doublets is seen. The derivation of these further fragments can be better understood with reference to FIGS. 42-44.

FIG. 42 shows a plot of the apparent gel mobilities of these fragments and their lengths in amino-acid residues, indicating that the apparent gel mobilities can be understood in terms of a characteristic set of fragment lengths.

As illustrated in FIG. 43, all of these fragments are at intervals of either ~34 residues or ~17 residues which is the equivalent of a single tau repeat, or half of it. All of the fragments generated can therefore be understood as arising from a simple set of proteolytic cleavages occurring at the positions indicated by the arrowheads in FIG. 43 from a basic heptameric aggregate, formed as shown in the figure. In this scheme the fragments arise as the full combinatorial set of the proposed cleavages occurring at the 3 possible approximate positions shown by the arrowheads at either end of the aggregate. The corresponding predicted immunoreactivity patterns seen with mAb 342 and T46 associated with these fragments are also tabulated.

FIG. 44 shows these same fragments in descending order of length and increasing gel mobility. Although the heptameric aggregate is shown for convenience as arising entirely from full-length tau molecules, it will be appreciated that the 12/14 kD fragment could be interposed within the proposed aggregate, replacing some of the binding partners, and that the precise pattern of inclusion of these short fragments in the aggregate will determine which precise fragments from the full set predominate in a given instance. Therefore, the production of this family of proteolytic fragments is better understood as a possible repertoire which can be instantiated in various ways within the cell.

Example 4

Inhibitory Effects of Compounds on Production of Proteolytic Fragment

Having achieved a stable cell system in which production of the 12 kD fragment (and others) could be controlled, the model was used to test the inhibitory effects of reduced thionine. This is shown in FIG. 23. In each set of lanes, there is inducible production of the 12 kD band in the presence of increasing concentrations of IPTG inducing higher levels of T40. As the thionine concentration is increased, the production of the 12 kD band from T40 is suppressed. This is shown quantitatively in FIG. 24. In the absence of thionine, induction of T40 at increasing concentrations of IPTG leads to a corresponding increased production of the 12 kD fragment. In the presence of 2 µM thionine, there is still induction of T40, but it is not converted into to the 12 kD fragment.

As reduced thionine is itself toxic, it is necessary to control for reduction in the levels of T40 induced by corresponding does of IPTG at higher levels of thionine. This can be achieved by determining the ratio of 12 kD:T40, which permits averaging the data across IPTG levels and shows a dose-dependent reduction in the level of the 12 kD relative to full-length tau.

The activities of various compounds in the T40/12 kD assay are shown in FIGS. 9 to 16.

Results are expressed in terms of the ratio of 12 kD:T40 following induction of full-length tau (T40) by treatment cells with IPTG (0, 10, 25, 50 µM) in the presence of thionine or tolonium chloride introduced at the concentrations shown in the presence of reducing agents (200 µM DTT/ascorbate), or chlorpromazine or tacrine introduced without reducing agents. As can be seen, thionine and tolonium chloride produce essentially identical inhibition, whereas chlorpromazine and tacrine are non-inhibitory in the same concentration range. The effect of the reducing agents alone was tested in control experiments which showed no significant difference was seen in the 12 kD:T40 ratio in the presence of reducing agents alone.

The properties of the cell line producing higher molecular weight degradation products were also examined with MB and DMMB (dimethyl-methylene blue).

As can be seen in FIG. 45, DMMB proved to be surprisingly potent in the cell model. Its inhibitory activity could be seen both in the absence of IPTG induction and following induction. Treatment with 1 µM DMMB effectively abolished all degradation products within the cell. Further experience with MB and DMMB has shown that even apparent base-line production of the 12/14 kD species is largely determined by aggregation. That is, the constitutive production of the 295-391 fragment is itself either below the level of detection by immunoblot or else it is stabilised by spontaneous aggregation so as to reach levels within the cell which can be detected by immunoblot. Alternatively, the apparent base-line levels of the 12/14 kD fragment seen without IPTG induction and in the absence of treatment with a tau-aggregation inhibitor may itself be dominated by templated aggregation-dependent production from the leakage levels of T40 produced in absence of induction. Whatever the combination of factors which determines the levels of the 12/14 kD fragment in the base-line condition, its apparent expression can be essentially eliminated, along with higher molecular weight aggregation products, by a potent aggregation inhibitor such as DMMB. These results further confirm that production of the higher molecular weight proteolytic fragments (ie 30/32, 36/38, 42/44 kD) is also dependent on critical tau-tau binding interactions occurring through the repeat domain, as shown in FIGS. 41, 43 and 44.

FIG. 46 shows the activity of DMMB on base-line expression of the 12/14 kD species, using the same set of assumptions regarding intracellular tau concentration and in vitro tau-tau binding affinity used in FIGS. 10-16. In this case DMMB is found to have an apparent KI within the cell of 4.4 nM, and the cellular B50 value is ~100 nM. This indicates that DMMB is highly potent within the cellular milieu.

Example 5

Comparison of Inhibitory Effects of Reduced and Oxidised Compounds

The mathematical model used for the in vitro data was used to analyse the effects of test substances in the T40:12 kD cell assay. Using the known values for Kd and KI from in vitro data, the expression indicated was used to solve for the intracellular concentration of full-length tau (see e.g. FIG. 10).

This was found to be about 500 nM, which is in the range expected from studies of tau in brain and in cell systems. A good fit to the experimental data was obtained implying that for some compounds the inhibition of production of truncated tau within the cell can be predicted from the approximate Kd and KI values determined experimentally in vitro.

Example 6

Examination of Inhibitory Properties of Diaminophenothiazines

In in vitro studies, the most active inhibitors of tau-tau binding identified were the reduced forms of diaminophenothiazines having 0, 2 or 3 methyl groups. FIG. 25 shows the reduced forms of such compounds. The corresponding tau-tau binding curves are shown as a function of molar ratio with respect to tau in FIGS. 26 and 27. As shown, compounds of the "desmethyl series" (0, 2 or 3 methyl groups) produce approximately 50% inhibition of tau-tau binding (shown on the vertical axis) at molar ratios of 3:1-4:1 of compound:tau 'AMR' shown on log scale on horizontal axis). The mean molar ratio for 50% inhibition of tau-tau binding for this group of compounds is 4:1.

Diaminophenothiazines having 4 or 6 methyl groups (the "methylated group") have a biphasic action, with enhancement of tau-tau binding at lower concentration, and inhibition of tau-tau binding at high concentrations (FIG. 27). These compounds thus require much higher molar ratios to effect 50% inhibition of tau-tau binding.

Examination of other features of the diaminophenothiazine compound was also carried out. Substitution of the heterocyclic nitrogen or sulphur atoms was found to severely interfere with inhibitory potency of the compounds. Likewise, removal of the diamino groups was found to be detrimental to the inhibitory activity. It thus appeared that the diamino and heterocyclic NB and S-structures are important for activity of the molecules in the inhibition of tau-tau binding.

For comparison, two methods were used to determine inhibitory activity in the tau-tau assay: STB is the mean tau-tau binding observed at 1 and 10 μg/ml of compound at standard tau concentrations of 488 nM; LB50 is log10 molar ratio of compound:tau producing 50% inhibition of tau-tau binding (FIG. 28). As shown in FIG. 29, there is a strong correlation between the STB and LB50 values for a range of compounds, with chlorpromazine and riboflavin being two outliers (see also FIGS. 30 and 31).

Example 7

Inhibitory Activity and Diffusion Potential

FIG. 32 indicates that there is a correlation between the number of methyl groups (NMETH) in a test compound and both the reduction potential (E) and diffusion coefficient (DIF). In all comparisons, the Spearman rank correlation was used. As shown in FIG. 32, a strong inverse relationship between the number of methyl groups (NMETH) and the reduction potential can be seen only if methylene blue is excluded (normal type: correlation values including methylene blue; italic type: correlation values excluding methylene blue).

This indicates that methylene blue has a disproportionately high reduction potential relative to number of methyl groups (NMETH) in this series. There is also a strong positive correlation between the number of methyl groups and the diffusion coefficient (DIF, FIG. 32).

As well as there being no observed correlation between the number of methyl groups and reduction potential (FIG. 33), it was surprisingly found that there was no observed correlation between reduction potential and inhibitory potential (FIG. 34b), although the extent of reduction of the diaminophenothiazines in the conditions of the assay is highly correlated with reduction potential (FIG. 33). And indeed, there is no correlation between the extent of reduction of these compounds and inhibitory potency (FIG. 34a). On the other hand, there is a strong inverse correlation between the inhibitory potency of a compound and its diffusion coefficient, and it is possible to predict estimated LB50 and STB values as linear functions of reduction coefficient and diffusion coefficient when greater weighting is given to the diffusion coefficient (FIGS. 35, 36 and 37). Both the LB50 and STB values are found to be uniformly low for NMETH values up to and including 3, but for higher NMETH values (in particular methylene blue, NMETH=4) there is a disproportionately low inhibitory potency relative to the number of methyl groups. This may relate to the symmetric placement of the methyl groups which interferes with the stacking ability of the molecules, as measured by the diffusion coefficient. This can be seen, for example, in the crystalline structure of methylene blue (see FIG. 38). The diaminophenothiazine molecule is essentially flat and forms stacking arrays. The presence of charge in the molecule, as in the oxidised form, prevents the formation of such stacking arrays, and it appears to be the propensity of the reduced form of this compound to form such stacking relationships that determines the inhibitory potency of the series.

The experiments carried out by the present inventors examined the binding of full-length tau in the aqueous-phase to the truncated repeat domain fragment of tau in the solid-phase, as described in further detail in WO96/30766. Binding was detected with either mAb 342 or mAb 499. As shown in FIG. 39, there is typical tau concentration-dependent tau-tau binding in the presence of a large excess of the standard reducing agent dithiothreitol (DTT, 1 mM). However, the inhibitory activity of phenothiazines is also demonstrated in the presence of DTT (1 mM) in the standard configuration of the assay described above (i.e. the data for STB and LB50). The present inventors thus conclude that the inhibitory activity cannot be attributed to DTT per se, but rather to the presence of the phenothiazines in their reduced form, due to an excess of DTT.

In summary, the present inventors provide herein a potential, significantly improved, system for the treatment and prophylaxis of diseases such as Alzheimer's Disease in which proteins undergo induced conformational polymerisation, e.g. as illustrated in the case of Alzheimer's disease by pathological tau-tau binding. The important teachings of this application, viz that the diffusion coefficient of a compound may important in determining its inhibitory potency towards this induced conformational protein polymerisation, are potentially of great benefit in advancing our understanding of, and ability to provide therapy for, diseases such as Alzheimer's Disease. Finally, by combining the findings on the preferality of the reduced form of MB, and demonstration of its activity in the cell-based assay at concentrations substantially below those predicted solely on the basis of in vitro data, the inventors have shown that this compound, and others like it, could be used an appropriate reducing formulation for the prophylaxis or treatment of AD and related disorders.

REFERENCES

Abrahamson, M., Jonsdottir, S., Olafsson, I. & Grubb, A. (1992) Hereditary cystatin C amyloid angiopathy identification of the disease-causing mutation and specific diagnosis by polymerase chain reaction based analysis. *Human Genetics* 89, 377-380.

Booth, D. R., Sunde, M., Bellotti, V., Robinson, C. V., Hutchinson, W. L., Fraser, P. E., Hawkins, P. N., Dobson, C. M., Radford, S. E., Blake, C. C. F. & Pepys, M. B. (1997) Instability, unfolding and aggregation of human lysozyme variants underlying amyloid fibrillogenesis. *Nature* 385, 787-793.

Carrell, R. W. & Gooptu, B. (1998) Conformational changes and disease—serpins, prions and Alzheimer's. *Current Opinion in Structural Biology* 8, 799-809.

Chiti, F., Webster, P., Taddei, N., Clark, A., Stafani, M., Ramponi, G. & Dobson, C. (1999) Designing conditions for in vitro formation of amyloid protofilaments and fibrils. *Proceedings of the National Academy of Sciences, USA* 96, 3590-3594.

Czech, C., Tremp, G. & Pradier, L. (2000) Presenilins and Alzheimer's disease: biological functions and pathogenic mechanisms. *Progress in Neurobiology* 60, 363-384.

Davis, R. L., Shrimpton, A. E., Holohan, P. D., Bradshaw, C., Feiglin, D., Collins, G. H., Sonderegger, P., Kinter, J., Becker, L. M., Lacbawan, F., Krasnewich, D., Muenke, M., Lawrence, D. A., Yerby, M. S., Shaw, C.-M., Gooptu, B., Elliott, P. R., Finch, J. T., Carrell, R. W. & Lomas, D. A. (1999) Familial dementia caused by polymerization of mutant neuroserpin. *Nature* 401, 376-379.

DiFiglia, M., Sapp, E., Chase, K. O., Davies, S. W., Bates, G. P., Vonsattel, J. P. & Aronin, N. (1997) Aggregation of huntingtin in neuronal intranuclear inclusions and dystrophic neurites in brain. *Science* 277, 1990-1993.

Dische, F. E., Wernstedt, C., Westermark, G. T., Westermark, P., Pepys, M. B., Rennie, J. A., Gilbey, S. G. & Watkins, P. J. (1988) Insulin as an amyloid-fibril protein at sites of repeated insulin injections in a diabetic patient. *Diabetologia* 31, 158-161.

Gasset, M., Bladwin, M. A., Lloyd, D. H., abriel, J.-M., Holtzman, D. M., Cohen, F. E., Fletterick, R. & Prusiner, S. B. (1992) Predicted a-helical region of the prion protein when synthesized as peptides form amyloid. *Proceedings of the National Academy of Sciences, USA* 89, 10940-10944.

Glenner, G. G. & Wong, C. W. (1984) Alzheimer's disease: initial report of the purification and characterisation of a novel cerebrovascular amyloid protein. *Biochemical and Biophysical Research Communications* 120, 885-890.

Goate, A., Chartier-Harlin, M.-C., Mullan, M., Brown, J., Crawford, F., Fidani, L., Giuffra, L., Haynes, A., Irving, N., James, L., Mant, R., Newton, P., Rooke, K., Roques, P., Talbot, C., Pericak-Vance, M., Roses, A., Williamson, R., Rossor, M., Owen, M. & Hardy, J. (1991) Segregation of a missense mutation in the amyloid precursor protein gene with familial Alzheimer's disease. *Nature* 349, 704-706.

Gorevic, P. D., Casey, T. T., Stone, W. J., DiRaimondo, C. R., Prelli, F. C. & Frangione, B. (1985) b-2 Microglobulin is an amyloidogenic protein in man. *Journal of Clinical Investigation* 76, 2425-2429.

Gustavsson, A., Engström, U. & Westermark, P. (1991) Normal transthyretin and synthetic transthyretin fragments form amyloid-like fibrils in vitro. *Biochemical and Biophysical Research Communications* 175, 1159-1164.

Hutton, M., Lendon, C., Rizzu, P., Baker, M., Froelich, S., Houlden, H., Pickering-Brown, S., Chakraverty, S., Isaacs, A., Grover, A., Hackett, J., Adamson, J., Lincoln, S., Dickson, D., Davies, P., Petersen, R. C., Stevens, M., de Graaf, E., Wauters, E., van Baren, J., Hillebrand, M., Joosse, M., Kwon, J. M., Nowotny, P., Che, L. K., Norton, J., Morris, J. C., Reed, L. A., Trojanowski, J. Q., Basun, H., Lannfelt, L., Neystat, M., Fahn, S., Dark, F., Tannenberg, T., Dodd, P. R., Hayward, N., Kwok, J. B. J., Schofield, P. R., Andreadis, A., Snowden, J., Craufurd, D., Neary, D., Owen, F., Oostra, B. A., Hardy, J., Goate, A., van Swieten, J., Mann, D., Lynch, T. & Heutink, P. (1998) Association of missense and 5'-splice-site mutations in tau with the inherited dementia FTDP-17. *Nature* 393, 702-705.

Johansson, B., Wernstedt, C. & Westermark, P. (1987) Atrial natriuretic peptide deposited as atrial amyloid fibrils. *Biochemical and Biophysical Research Communications* 148, 1087-1092.

Lomas, D. A., Evans, D. L., Finch, J. T. & Carrell, R. W. (1992) The mechanism of Z a1-antitrypsin accumulation in the liver. *Nature* 357, 605-607.

Maury, C. P. & Baumann, M. (1990) Isolation and characterization of cardiac amyloid in familial amyloid polyneuropathy type IV (Finnish): relation of the amyloid protein to variant gelsolin. *Biochimica et Biophysica Acta* 1096, 84-86.

Paulson, H. L. (1999) Human genetics '99: trinucleotide repeats. *American Journal of Human Genetics* 64, 339-345.

Pepys, M. B., Hawkins, P. N., Booth, D. R., Vigushin, D. M., Tennent, G. A., Soutar, A. K., Totty, N., Nguyen, O., Blake, C. C. F., Terry, C. J., Feest, T. G., Zalin, A. M. & Hsuan, J. J. (1993) Human lysozyme gene mutations cause hereditary systemic amyloidosis. *Nature* 362, 553-557.

Polymeropoulos, M. H., Lavedan, C., Leroy, E., Ide, S. E., Dehejia, A., Dutra, A., Pike, B., Root, H., Rubenstein, J., Boyer, R., Stenroos, E. S., Chandrasekharappa, S., Athanassiadou, A., Papaetropoulos, T., Johnson, W. G., Lazzarini, A. M., Duvoisin, R. C., Di Iorio, G., Golbe, L. I. & Nussbaum, R. L. (1997) Mutation in the a-synuclein gene identified in families with Parkinson's disease. *Science* 276, 2045-2047.

Prusiner, S. B., Scott, M. R., DeArmond, S. J. & Cohen, F. E. (1998) Prion protein biology. *Cell* 93, 337-348.

Shibata, N., Hirano, A., Kobayashi, M., Siddique, T., Deng, H. X., Hung, W. Y., Kato, T. & Asayama, K. (1996) Intense superoxide dismutase-1 immunoreactivity in intracytoplasmic hyaline inclusions of familial amyotrophic lateral sclerosis with posterior column involvement. *Journal of Neuropathology and Experimental Neurology* 55, 481-490.

Sletten, K., Westermark, P. & Natvig, J. B. (1976) Characterization of amyloid fibril proteins from medullary carcinoma of the thyroid. *Journal of Experimental Medicine* 143, 993-998.

Spillantini, M. G., Crowther, R. A., Jakes, R., Hasegawa, M. & Goedert, M. (1998) a-Synuclein in filamentous inclusions of Lewy bodies from Parkinson's disease and dementia with Lewy bodies. *Proceedings of the National Academy of Sciences, USA* 95, 6469-6473.

Uemichi, T., Liuepnicks, J. j. & Benson, M. D. (1994) Hereditary renal amyloidosis with a novel variant fibrinogen. *Journal of Clinical Investigation* 93, 731-736.

Westermark, P., Engstrom, U., Johnson, K. H., Westermark, G. T. & Betsholtz, C. (1990) Islet amyloid polypeptide: pinpointing amino acid residues linked to amyloid fibril formation. *Proceedings of the National Academy of Sciences, USA* 87, 5036-5040.

Westermark, P., Johnson, K. H., O'Brien, T. D. & Betsholtz, C. (1992) Islet amyloid polypeptide—a novel controversy in diabetes research. *Diabetologia* 35, 297-303.

Westermark, P., Johnson, K. H. & Pitkanen, P. (1985) Systemic amyloidosis: A review with emphasis on pathogenesis. *Applied Physiology* 3, 55-68.

Wischik, C. M., Novak, M., Thøgersen, H. C., Edwards, P. C., Runswick, M. J., Jakes, R., Walker, J. E., Milstein, C., M., R. & Klug, A. (1988) Isolation of a fragment of tau derived from the core of the paired helical filament of Alzheimer's disease. *Proceedings of the National Academy of Sciences, USA* 85, 4506-4510.

The invention claimed is:

1. A method for the treatment of Alzheimer's Disease, which method comprises administering to a subject in need thereof a medicament composition comprising a diaminophenothiazine, wherein the diaminophenothiazine has been pre-reduced such that it is present in at least 80, 90, 95 or 99% reduced (leuco-) form,
   wherein the diaminophenothiazine is pre-reduced by addition of an exogenous reducing agent,
   and wherein the reduced form is lyophilised,
   wherein the pre-reduced diaminophenothiazine has the formula:

(I)

wherein $R_1$, $R_3$, $R_4$, $R_6$, $R_7$ and $R_9$ are independently selected from hydrogen, halogen, hydroxy, carboxy, substituted or unsubstituted alkyl, haloalkyl or alkoxy;
$R_5$ is hydrogen; and
each $R_{10}$ and $R_{11}$ is independently selected from hydrogen, hydroxy, carboxy, substituted or unsubstituted alkyl, haloalkyl or alkoxy;
or is a pharmaceutically acceptable salt thereof.

2. A method as claimed in claim 1 wherein the reduced form is stabilized in the reduced state by addition of a stabilizing agent.

3. A method as claimed in claim 2 wherein the reduced form is lyophilized with the stabilizing agent.

4. A method as claimed in claim 1 wherein the medicament composition further comprises one or more additives selected from the group consisting of pharmaceutically-acceptable excipients, carriers and buffers.

5. A method as claimed in claim 4 wherein the medicament composition is a slow release formulation.

6. A method as claimed in claim 1 wherein $R_1$, $R_3$, $R_4$, $R_6$, $R_7$ and $R_9$ are independently selected from -hydrogen, —$CH_3$, —$C_2H_5$ or —$C_3H_7$; each $R_{10}$ and $R_{11}$ are independently selected from hydrogen, —$CH_3$, —$C_2H_5$ or —$C_3H_7$; and $R_5$ is hydrogen, —$CH_3$, —$C_2H_5$ or —$C_3H_7$.

7. A method as claimed in claim 1 wherein the diaminophenothiazine has 0, 2, 3 or 4 methyl groups around the diaminophenothiazine nucleus.

8. A method as claimed in claim 1 wherein the diaminophenothiazine is asymmetrically methylated.

9. A method as claimed in claim 8 wherein the diaminophenothiazine is selected from the group consisting of tolonium chloride, Azure A, Azure B and thionine.

10. A method as claimed in claim 8 wherein the diaminophenothiazine is selected from the group consisting of Methylene Blue, Toluidine Blue O and 1,9-Dimethylmethylene Blue.

11. A method as claimed in claim 3 wherein the stabilizing agent is ascorbic acid.

12. A method as claimed in claim 1 wherein the treatment comprises administering a therapeutically effective amount of the medicament composition to a patient in need thereof.

13. A method as claimed in claim 12 wherein the treatment comprises administering the medicament composition to a patient in need thereof three times a day, and wherein the medicament composition comprises 20 mg, 50 mg or 100 mg diaminophenothiazine combined with 2× mg ratio of ascorbic acid such that more than 90% diaminophenothiazine is reduced prior to ingestion.

14. A method as claimed in claim 12 wherein the treatment comprises administering to a patient in need thereof a diaminophenothiazine which is thionine in a daily dosage of between 1 and 1000 mg optionally divided into 1 to 8 unit doses.

15. A method as claimed in claim 12 wherein the treatment comprises administering to a patient in need thereof a diaminophenothiazine which is methylene blue in a daily dosage of from about 3.2 to about 3.5 mg/kg body weight.

* * * * *